United States Patent
Purohit et al.

(10) Patent No.: US 9,388,125 B2
(45) Date of Patent: Jul. 12, 2016

(54) COMPOSITIONS, METHODS, AND SYSTEMS FOR THE SYNTHESIS AND USE OF IMAGING AGENTS

(75) Inventors: Ajay Purohit, Sudbury, MA (US); Pedro Benites, Watertown, MA (US); Edward H. Cheesman, Lunenburg, MA (US); Joel Lazewatsky, Auburndale, MA (US); L. Veronica Lee, Carlisle, MA (US); Richard R. Cesati, Pepperell, MA (US); Richard J. Looby, Reading, MA (US); Heike S. Radeke, South Grafton, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 263 days.

(21) Appl. No.: 13/697,287

(22) PCT Filed: May 11, 2011

(86) PCT No.: PCT/US2011/036142
§ 371 (c)(1),
(2), (4) Date: Feb. 27, 2013

(87) PCT Pub. No.: WO2011/143360
PCT Pub. Date: Nov. 17, 2011

(65) Prior Publication Data
US 2013/0149244 A1 Jun. 13, 2013

Related U.S. Application Data

(60) Provisional application No. 61/333,618, filed on May 11, 2010, provisional application No. 61/405,524, filed on Oct. 21, 2010, provisional application No. 61/405,571, filed on Oct. 21, 2010.

(51) Int. Cl.
| | | |
|---|---|---|
| A61K 51/00 | (2006.01) |
| A61M 36/14 | (2006.01) |
| C07C 277/08 | (2006.01) |
| A61K 51/04 | (2006.01) |
| C07B 59/00 | (2006.01) |
| C07C 53/06 | (2006.01) |
| C07C 217/58 | (2006.01) |
| C07C 255/54 | (2006.01) |
| C07C 279/10 | (2006.01) |
| C07C 279/24 | (2006.01) |
| C07C 309/65 | (2006.01) |
| C07C 309/66 | (2006.01) |
| C07C 309/73 | (2006.01) |
| C07C 53/10 | (2006.01) |
| C07C 53/18 | (2006.01) |
| C07C 63/08 | (2006.01) |
| C07C 213/02 | (2006.01) |
| C07C 303/28 | (2006.01) |
| C07C 303/30 | (2006.01) |
| C07C 309/04 | (2006.01) |
| C07C 309/30 | (2006.01) |
| C07C 277/00 | (2006.01) |

(52) U.S. Cl.
CPC ............. *C07C 277/08* (2013.01); *A61K 51/04* (2013.01); *A61K 51/0406* (2013.01); *C07B 59/001* (2013.01); *C07C 53/06* (2013.01); *C07C 53/10* (2013.01); *C07C 53/18* (2013.01); *C07C 63/08* (2013.01); *C07C 213/02* (2013.01); *C07C 217/58* (2013.01); *C07C 255/54* (2013.01); *C07C 279/10* (2013.01); *C07C 279/24* (2013.01); *C07C 303/28* (2013.01); *C07C 303/30* (2013.01); *C07C 309/04* (2013.01); *C07C 309/30* (2013.01); *C07C 309/65* (2013.01); *C07C 309/66* (2013.01); *C07C 309/73* (2013.01); *C07C 277/00* (2013.01)

(58) Field of Classification Search
USPC ........................................ 424/1.89
See application file for complete search history.

(56) References Cited

U.S. PATENT DOCUMENTS

| 4,094,881 A | 6/1978 | Berges |
| 4,270,537 A | 6/1981 | Romaine |
| 4,596,556 A | 6/1986 | Morrow et al. |

(Continued)

FOREIGN PATENT DOCUMENTS

| CN | 101555232 A | 10/2009 |
| CN | 101585816 A | 11/2009 |

(Continued)

OTHER PUBLICATIONS

Paixã al. (Acta. Crys. 1998, C54, 1484-1486).*

(Continued)

*Primary Examiner* — Michael G Hartley
*Assistant Examiner* — Melissa Perreira
(74) *Attorney, Agent, or Firm* — Wolf, Greenfield & Sacks, P.C.

(57) ABSTRACT

The present invention generally relates to novel synthetic methods, systems, kits, salts, and precursors useful in medical imaging. In some embodiments, the present invention provides compositions comprising an imaging agent precursor, which may be formed using the synthetic methods described herein. An imaging agent may be converted to an imaging agent using the methods described herein. In some cases, the imaging agent is enriched in $^{18}F$. In some cases, an imaging agent including salt forms (e.g., ascorbate salt) may be used to image an area of interest in a subject, including, but not limited to, the heart, cardiovascular system, cardiac vessels, brain, and other organs.

17 Claims, 12 Drawing Sheets

(56) References Cited

U.S. PATENT DOCUMENTS

| | | | |
|---|---|---|---|
| 4,622,217 | A | 11/1986 | Wieland |
| 4,790,824 | A | 12/1988 | Morrow et al. |
| 4,886,499 | A | 12/1989 | Cirelli et al. |
| 4,940,460 | A | 7/1990 | Casey et al. |
| 4,941,880 | A | 7/1990 | Burns |
| 5,015,235 | A | 5/1991 | Crossman |
| 5,064,413 | A | 11/1991 | McKinnon et al. |
| 5,141,496 | A | 8/1992 | Dalto et al. |
| 5,190,521 | A | 3/1993 | Hubbard et al. |
| 5,312,335 | A | 5/1994 | McKinnon et al. |
| 5,328,483 | A | 7/1994 | Jacoby |
| 5,334,144 | A | 8/1994 | Alchas et al. |
| 5,339,163 | A | 8/1994 | Homma et al. |
| 5,383,851 | A | 1/1995 | McKinnon, Jr. et al. |
| 5,417,662 | A | 5/1995 | Hjertman et al. |
| 5,466,220 | A | 11/1995 | Brenneman |
| 5,480,381 | A | 1/1996 | Weston |
| 5,503,627 | A | 4/1996 | McKinnon et al. |
| 5,520,639 | A | 5/1996 | Peterson et al. |
| 5,527,288 | A | 6/1996 | Gross et al. |
| 5,569,189 | A | 10/1996 | Parsons |
| 5,599,302 | A | 2/1997 | Lilley et al. |
| 5,649,912 | A | 7/1997 | Peterson |
| 5,704,911 | A | 1/1998 | Parsons |
| 5,874,573 | A | 2/1999 | Winchell et al. |
| 5,893,397 | A | 4/1999 | Peterson et al. |
| 5,993,412 | A | 11/1999 | Deily et al. |
| 6,511,648 | B2 | 1/2003 | Harris et al. |
| 8,491,868 | B2 | 7/2013 | Purohit et al. |
| 2004/0018162 | A1* | 1/2004 | Bimczok et al. ............. 424/70.2 |
| 2006/0127309 | A1 | 6/2006 | Raffel et al. |
| 2010/0221182 | A1 | 9/2010 | Purohit et al. |
| 2014/0030189 | A1 | 1/2014 | Purohit et al. |
| 2014/0328756 | A1 | 11/2014 | Cesati et al. |

FOREIGN PATENT DOCUMENTS

| | | | |
|---|---|---|---|
| EP | 1 749 815 A1 | 2/2007 | |
| FR | 2 343 732 A1 | 10/1977 | |
| GB | 672048 A * | 5/1952 | ............ C07C 277/06 |
| GB | 1215255 A * | 12/1970 | ........... A61K 31/155 |
| JP | 3-023203 A | 1/1991 | |
| WO | WO 97/13537 A1 | 4/1997 | |
| WO | WO 97/37705 A1 | 10/1997 | |
| WO | WO 99/18053 A1 | 4/1999 | |
| WO | WO 99/34850 A1 | 7/1999 | |
| WO | WO 99/52861 A1 | 10/1999 | |
| WO | WO 00/09115 A1 | 2/2000 | |
| WO | WO 01/060416 A2 | 8/2001 | |
| WO | WO 2005/009479 A1 | 2/2005 | |
| WO | WO 2005/053615 A2 | 6/2005 | |
| WO | WO 2005/079391 A2 | 9/2005 | |
| WO | WO 2005/095345 A2 | 10/2005 | |
| WO | WO 2005/115971 A1 | 12/2005 | |
| WO | WO 2006/032705 A2 | 3/2006 | |
| WO | WO 2006/044280 A1 | 4/2006 | |
| WO | WO 2006/136846 A1 | 12/2006 | |
| WO | WO 2008/071574 A1 | 6/2008 | |
| WO | WO 2008/075040 A2 | 6/2008 | |
| WO | WO 2008/082305 A1 | 7/2008 | |
| WO | WO 2008/083056 A2 | 7/2008 | |
| WO | WO 2008/115593 A1 | 9/2008 | |
| WO | WO 2008/124651 A2 | 10/2008 | |
| WO | WO 2010/015387 A1 | 2/2010 | |
| WO | WO 2010/115881 A1 | 10/2010 | |
| WO | WO 2010/120368 A2 | 10/2010 | |
| WO | WO 2011/005322 A2 | 1/2011 | |
| WO | WO 2011/097649 A2 | 8/2011 | |
| WO | WO 2011/143360 A2 | 11/2011 | |
| WO | WO 2013/036869 A2 | 3/2013 | |

OTHER PUBLICATIONS

International Preliminary Report on Patentability for PCT/US2012/054309 mailed Mar. 20, 2014.

Gaertner et al., Preclinical evaluation of 18F-LMI1195 for in vivo imaging of pheochromocytoma in the MENX tumor model. J Nucl Med. Dec. 2013;54(12):2111-7. doi: 10.2967/jnumed.113.119966. Epub Oct. 17, 2013.

Higuchi et al., Assessment of the 18F-labeled PET tracer LMI1195 for imaging norepinephrine handling in rat hearts. J Nucl Med. Jul. 2013;54(7):1142-6. doi: 10.2967/jnumed.112.104232. Epub May 13, 2013.

Lamoy et al., Cardiac imaging and uptake mechanism of 18F LMI1195, a novel PET cardiac neuronal imaging agent. J Nucl Med 51 (S2) 2010. Abstract 262.

Liu et al., Quantification of normal pattern of regional myocardial uptake of 18F LMI1195, a novel tracer for imaging myocardial sympathetic function: First-in-human study. J Nucl Med. 2010; 51 (S2): 1317.

Mistry et al., Dosimetry in nonhuman primates of [18F]LMI1195, a novel PET tracer for imaging the cardiac sympathetic nervous system. J Nucl Med 51 (S2)2010. Abstract 1447.

Radeke et al., Synthesis of Fluorinated Benzylguanidine Derivatives as Substrates for the cardiac Norepinephrine Transporter: Discovery of LMI1195. Proceedings of the 2011 World Molecular Imaging Congress. Sep. 10, 2011, Presentation No. T180.

Rouzet et al., La tomographie par emission de positons en cardiologie, Medecine Nucleaire. 2012;36:438-44.

Sahul et al., Targeted imaging of the spatial and temporal variation of matrix metalloproteinase activity in a porcine model of postinfarct remodeling: relationship to myocardial dysfunction. Circ Cardiovasc Imaging. Jul. 2011;4(4):381-91. doi: 10.1161/CIRCIMAGING.110.961854. Epub Apr. 19, 2011.

Su et al., Noninvasive targeted imaging of matrix metalloproteinase activation in a murine model of postinfarction remodeling. Circulation. Nov. 15, 2005;112(20):3157-67. Epub Nov. 7, 2005.

Tavakoli et al., Matrix metalloproteinase activation predicts amelioration of remodeling after dietary modification in injured arteries. Arterioscler Thromb Vasc Biol. Jan. 2011;31(1):102-9. doi: 10.1161/ATVBAHA.110.216036. Epub Oct. 14, 2010.

Tekabe et al., Noninvasive monitoring the biology of atherosclerotic plaque development with radiolabeled annexin V and matrix metalloproteinase inhibitor in spontaneous atherosclerotic mice. J Nucl Cardiol. Dec. 2010;17(6):1073-81. doi: 10.1007/s12350-010-9276-5. Epub Aug. 11, 2010.

Yu et al., Cardiac retention of PET neuronal imaging agent LMI1195 in different species: impact of norepinephrine uptake-1 and -2 transporters. Nucl Med Biol. Jul. 2013;40(5):682-8. doi: 10.1016/j.nucmedbio.2013.03.003. Epub Apr. 17, 2013.

Yu et al., LMI1195 PET imaging in evaluation of regional cardiac sympathetic denervation and its potential role in antiarrhythmic drug treatment. Eur J Nucl Med Mol Imaging. Dec. 2012;39(12):1910-9. doi: 10.1007/s00259-012-2204-y. Epub Aug. 4, 2012.

Yu et al., LMI1195: A New 18F Benzylguanidine Analog for PET Cardiac Sympathetic Neuronal Imaging. ACC.10. Georgia World Congress Center. Mar. 15, 2010. Abstract Only.

Extended European Search Report for EP 12152815.2 mailed on Jun. 20, 2012.

Extended European Search Report for EP 12152816.0 mailed on Jun. 20, 2012.

Extended European Search Report for EP 12152817.8 mailed on Jun. 22, 2012.

Extended European Search Report for EP 12152818.6 mailed on Jun. 22, 2012.

Invitation to Pay Additional Fees for PCT/US2007/088500 mailed Dec. 19, 2008.

International Search Report and Written Opinion for PCT/US2007/088500 mailed Mar. 13, 2009.

International Preliminary Report on Patentability for PCT/US2007/088500 mailed Jul. 9, 2009.

International Search Report and Written Opinion for PCT/US2011/036142 mailed Dec. 22, 2011.

International Preliminary Report on Patentability for PCT/ US2011/036142 mailed Nov. 22, 2012.

International Search Report and Written Opinion for PCT/US2012/054309 mailed Feb. 27, 2013.

[No Author Listed] Hejishu. 1985:9;31-2.

(56) References Cited

OTHER PUBLICATIONS

[No Author Listed] Zonghua Heyixue Zazhi Chinese J Nucl Med. 1984 4(3) 157-9.
Adams et al., Nucleophilic routes to selectively fluorinated aromatics. Chem Soc Rev. 1999;28:225-31.
Adams et al., the formation of 4,4'-difluorobenzophenone from 4,4'-dinitrodiphenylmethane. J Fluorine Chem. 1998;92:127-129.
Akgun et al., N1'-(p-[18F]Fluorobenzyl)naltrindole (p-[18F]BNTI) as a potential PET imaging agent for DOP receptors. J Labelled Comp Radiopharm. 2006;49:857-866.
Amartey et al., An efficient batch preparation of high specific activity. Appl Radiat Isot. May 2001;54(5):711-4.
Anbarasan et al., Efficient synthesis of aryl fluorides. Angew Chem Int Ed Engl. Mar. 15, 2010;49(12):2219-22.
Angelini et al., Nucleophilic aromatic substitution of activated cationic groups by 18F-labeled Fluoride. A useful route to no-carrier-added (NCA) 18F-labeled aryl fluorides.. J Fluorine Chem. 1985;27:177-91.
Armour, Myocardial ischaemia and the cardiac nervous system. Cardiovasc Res. 1998;41:41-54.
Badiang et al., One-Step Conversion of Aldehydes to Oxazolines and 5,6-Dihydro-4 H-1,3-oxazines Using 1,2- and 1,3-Azido Alcohols. J Org Chem. 1996;61:2484-87.
Barlin et al., Useful preparations involving the reactions of nucleophiles with some trimethylammonio-derivatives of nitrogen heterocycles.. J Chem Soc., Perkin Trans 1. 1972:1269-72.
Bax et al., $^{123}$ I-mIBG scintigraphy to predict inducibility of ventricular arrhythmias on cardiac electrophysiology testing: a prospective multicenter pilot study. Circ Cardiovasc Imaging. Sep. 2008;1(2): 131-40. Epub Jul. 30, 2008.
Beletskaya et al., Catalytic sandmeyer bromination. Synthesis. 2007; (No. 16):2534-38.
Bengel et al., Assessment of cardiac sympathetic neuronal function using PET imaging. J Nucl Cardiol. Sep.-Oct. 2004;11(5):603-16.
Berge et al., Pharmaceutical salts. J Pharm Sci. Jan. 1977;66(1):1-19.
Beringer et al., Diaryliodonium Salts. II. The Phenylation of Organic and Inorganic Bases. J. Am. Chem. Soc. 1953;75(11):2708-2712.
Berry et al., Para-[18F]fluorobenzylguanidine kinetics in a canine coronary artery occlusion model. J Nucl Cardiol. Mar.-Apr. 1996;3(2):119-29.
Berry et al., Uptake and retention kinetics of para-fluorine-18-fluorobenzylguanidine in isolated rat heart. J Nucl Med. Dec. 1996;37(12):2011-6.
Böhm et al., Evidence for reduction of norepinephrine uptake sites in the failing human heart. J Am Coll Cardiol. Jan. 1995;25(1):146-53.
Bolster et al., Synthesis of DL[1-11C]methionine. Int J Rad Appl Instrum A. 1986;37(10):1069-70.
Boogers et al., Cardiac sympathetic denervation assessed with 123-iodine metaiodobenzylguanidine imaging predicts ventricular arrhythmias in implantable cardioverter-defibrillator patients. J Am Coll Cardiol. Jun. 15, 2010;55(24):2769-77.
Bozek et al., 18F PET imaging of cardiac sympathetic denervation with LMI1195, a new neuronal imaging agent. J Nucl Med. 2010;51(S2):1701.
Bozek et al., Abstract 570: Heart Failure Imaging in the Rat with LMI1195: A New PET Cardiac Neuronal Imaging Agent. AHA Scientific Session 2009. Orlando, FL. Nov. 15-17, 2009. Circulation. 2009;120:S362.
Bryce et al., Electrophilic fluorination of aryltrialkyltin derivatives with caesium fluoroxysulphate. J Chem Soc., Chem Commun. 1986:1623-4.
Buck et al., Specific uptake of m-[125I]iodobenzylguanidine in the human neuroblastoma cell line SK-N-SH. Cancer Res. Dec. 1985;45(12 Pt 1):6366-70.
Calkins et al., Correlation between scintigraphic evidence of regional sympathetic neuronal dysfunction and ventricular refractoriness in the human heart. Circulation. Jul. 1993;88(1):172-9.
Carrío, Cardiac neurotransmission imaging. J Nucl Med. Jul. 2001;42(7):1062-76.
Castanet et al., Mild and regioselective iodination of electron-rich aromatics with N-iodosuccinimide and catalytic trifluoroacetic acid. Tetrahedron Lett. 2002;43:5047-48.
Cazorla et al., Metal-free electrophilic fluorination of alkyl trifluoroborates and boronic acids. Tetrahedron Lett. 2009;50:3936-8.
Chen et al., New perspectives on the role of autonomic nervous system in the genesis of arrhythmias. J Cardiovasc Electrophysiol. Jan. 2007;18(1):123-7. Epub Aug. 14, 2006.
Comar et al., Labelling and metabolism of methionine-methyl-11 C. Eur J Nucl Med. 1976;1(1):11-4.
Dae et al., Heterogeneous sympathetic innervation in German shepherd dogs with inherited ventricular arrhythmia and sudden cardiac death. Circulation. Aug. 19, 1997;96(4):1337-42.
Dahmen et al., A novel solid-phase synthesis of highly diverse guanidines: reactions of primary amines attached to the T2 linker. Org Lett. Nov. 16, 2000;2(23):3563-5.
Daly et al., The chemorelease of norepinephrine from mouse hearts. Structure-activity relationships. I. Sympathomimetic and related amines. J Med Chem. May 1966;9(3):273-80.
Degrado et al., Myocardial kinetics of carbon-11-meta-hydroxyephedrine: retention mechanisms and effects of norepinephrine. J Nucl Med. Aug. 1993;34(8):1287-93.
Degrado et al., Uptake mechanisms of meta-[123I]iodobenzylguanidine in isolated rat heart. Nucl Med Biol. Jan. 1995;22(1):1-12.
Ding et al., Synthesis of high specific activity (+)- and (−)-6-[18F]fluoronorepinephrine via the nucleophilic aromatic substitution reaction. J Med Chem. Feb. 1991;34(2):767-71.
Ding et al., Synthesis of high specific activity 6-[18F]fluorodopamine for positron emission tomography studies of sympathetic nervous tissue. J Med Chem. Feb. 1991;34(2):861-3.
Ermert et al., Comparison of pathways to the versatile synthon of no-carrier-added 1-bromo-4-[18F]fluorobenzene. J Labelled Comp Radiopharm. 2004;47:429-41.
Esler et al., The 2009 Carl Ludwig Lecture: Pathophysiology of the human sympathetic nervous system in cardiovascular diseases: the transition from mechanisms to medical management. J Appl Physiol. Feb. 2010;108(2):227-37. Epub Nov. 25, 2009.
Ewing, Diabetic autonomic neuropathy and the heart. Diabetes Res Clin Pract. Feb. 1996;30 Suppl:S31-6.
Farde et al., Positron emission tomography shows high specific uptake of racemic carbon-11 labelled norepinephrine in the primate heart. Eur J Nucl Med. Apr. 1994;21(4):345-7.
Filimonov et al., Unusually stable, versatile, and pure arenediazonium tosylates: their preparation, structures, and synthetic applicability. Org Lett. Sep. 18, 2008;10(18):3961-4. Epub Aug. 23, 2008.
Fowler et al., Radiopharmaceuticals. 12. A new rapid synthesis of carbon-11 labeled norepinephrine hydrochloride. J Med Chem. Feb. 1974;17(2):246-8.
Fowler et al., Synthesis and preliminary evaluation in animals of carrier-free 11C-1-dopamine hydrochloride: X. J Nucl Med. Nov. 1973;14(11):867-9.
Furuya et al., Carbon-Fluorine Bond Formation for the Synthesis of Aryl Fluorides. Synthesis (Stuttg). Jun. 1, 2010;2010(11):1804-1821.
Furuya et al., Fluorination of boronic acids mediated by silver(I) triflate. Org Lett. Jul. 2, 2009;11(13):2860-3.
Furuya et al., Palladium-mediated fluorination of arylboronic acids. Angew Chem Int Ed Engl. 2008;47(32):5993-6.
Furuya et al., Silver-mediated fluorination of functionalized aryl stannanes. J Am Chem Soc. Feb. 11, 2009;131(5):1662-3.
Galea et al., Synthesis of [$^{76}$Br]RPR 104632 for in Vivo Studies of the NMDA Receptor Channel Complex. J Labelled Comp Radiopharm. 1997;40:608-610. BIOSIS Abstract Accession No. PREV199800109838.
Ganguly et al., Ecofriendly iodination of activated aromatics and coumarins using potassium iodide and ammonium peroxodisulfate.. Synthesis. 2010;(9):1467-72.
Ganguly et al., Mild regioselective monobromination of activated aromatics and heteroaromatics with N-bromosuccinimide in tetrabutylammonium bromide.. Synthesis. 2005;(7):1103-08.

(56) References Cited

OTHER PUBLICATIONS

Garg et al., Synthesis and preliminary evaluation of para- and meta-[18F]fluorobenzylguanidine. Nucl Med Biol. Jan. 1994;21(1):97-103.
Glowniak et al., Evaluation of metaiodobenzylguanidine heart and lung extraction fraction by first-pass analysis in pigs. J Nucl Med. May 1992;33(5):716-23.
Grushin et al., Fluorination of Nonactivated Haloarenes via Arynes under Mild Conditions, Resulting from Further Studies toward Ar—F Reductive Elimination from Palladium(II). Organometallics. 2008;27(19):4825-4828.
Hanson et al., Radioiodinated 1-carboxamidino-4-phenylpiperazine: a potential adrenal and myocardial imaging radiopharmaceutical. Int J Appl Radiat Isot. Aug. 1982;33(8):629-32.
Henneman et al., Cardiac neuronal imaging: application in the evaluation of cardiac disease. J Nucl Cardiol. May-Jun. 2008;15(3):442-55. Epub Apr. 16, 2008.
Hilliard et al., Multiple Mechanisms of Action for Inhibitors of Histidine Protein Kinases from Bacterial Two-Component Systems. Antimicrob Agents Chemother. 1999;43:1693-99.
Högberg et al., Bioisosteric modification of PETT-HIV-1 RT-inhibitors: synthesis and biological evaluation. Bioorg Med Chem Lett. Feb. 7, 2000;10(3):265-8.
Horwitz et al., Some 6-substituted uracils. J Org Chem. 1961;26:3392-5.
Hubbard et al., Halo- and azidodediazoniation of arenediazonium tetrafluoroborates with trimethylsilyl halides and trimethylsilyl azide and sandmeyer-type bromodediazoniation with Cu(I)Br in [BMIM][PF6] ionic liquid. J Org Chem. Jan. 4, 2008;73(1):316-9. Epub Dec. 8, 2007.
Iskra et al., Nonmetal-catalyzed iodination of arenes with iodide and hydrogen peroxide. Synthesis. 2004;(11):1869-73.
Jacobson et al., Myocardial iodine-123 meta-iodobenzylguanidine imaging and cardiac events in heart failure. Results of the prospective ADMIRE-HF (AdreView Myocardial Imaging for Risk Evaluation in Heart Failure) study. J Am Coll Cardiol. May 18, 2010;55(20):2212-21. Epub Feb. 25, 2010.
Kabalka et al., Synthesis of organic bromides via organotrifluoroborates. Organometallics. 2004;23:4519-21.
Keen et al., In vivo cerebral protein synthesis rates with leucyl-transfer RNA used as a precursor pool: determination of biochemical parameters to structure tracer kinetic models for positron emission tomography. J Cereb Blood Flow Metab. Aug. 1989;9(4):429-45.
Kim et al., Evaluation of m-([18F]fluoropropyflbenzylguanidine ([18F]FPBG) for myocardial imaging in rat. J Nucl Med. 2009; 50 (Supplement 2):1940.
Kim et al., Expanding the substrate scope for C—H amination reactions: oxidative cyclization of urea and guanidine derivatives. Org Lett. Mar. 1, 2006;8(6):1073-6.
Klapars et al., Copper-catalyzed halogen exchange in aryl halides: an aromatic Finkelstein reaction. J Am Chem Soc. Dec. 18, 2002;124(50):14844-5.
Ko et al., Effects of anesthetic agents on cellular 123I-MIBG transport and in vivo 123I-MIBG biodistribution. Eur J Nucl Med Mol Imaging. Mar. 2008;35(3):554-61. Epub Oct. 13, 2007.
Krasikova et al., Asymmetric synthesis of 6-[18F]Fluoro-L-DOPA using a chiral nickel complex of the Schiff base of (S)-o-[(N-benzylprolyl)-amino]benzophenone and glycine. J Labelled Comp Radiopharm. 1999;42:S102-S104.
Krasnokutskaya et al., A new, one-step, effective protocol for the iodination of aromatic and heterocyclic compounds via aprotic diazotization of amines. Synthesis. 2007;(1):81-84.
Kraszkiewicz et al., Oxidative iodination of deactivated arenes in concentrated sulfuric acid with I2/NaIO4 Iodinating Systems. Synthesis. 2006;(7):1195-99.
Kumar et al., Bromination of aromatic compounds using ammonium bromide and ozone. Synthesis. 2010;(10):1629-32.
Langer et al., High specific radioactivity (1R,2S)-4-[(18)F]fluorometaraminol: a PET radiotracer for mapping sympathetic nerves of the heart. Nucl Med Biol. Apr. 2000;27(3):233-8.

Langer et al., PET and SPET tracers for mapping the cardiac nervous system. Eur J Nucl Med Mol Imaging. Mar. 2002;29(3):416-34.
Lazewatsky et al., Radiation dosimetry of LMI1195, first-in-human study of a novel F-18 labeled tracer for imaging myocardial innervation.. J Nucl Med. 2010;51(52):1432.
Lee et al., New potential and practical MIBG analogs for PET: meta-(3-(18F)fluoroalkyl)benzylguanidines. J Labelled Comp Radiopharm. 2001;44:S404-S406.
Lee et al., Potential and practical adrenomedullary PET radiopharmaceuticals as an alternative to m-iodobenzylguanidine: m-(omega-[18F]fluoroalkyl)benzylguanidines. Bioconjug Chem. Jan.-Feb. 2004;15(1):104-11.
Lee, Syntheses and Development of Novel PET and SPECT Radiotracers for Adrenomedullar, Fatty acid metabolism, and Tumor Imaging. Thesis. Dspace at INHA University. College of Natural Science. 2004. 109 pages.
Lenz et al., Dofetilide, a new class III antiarrhythmic agent. Pharmacotherapy. Jul. 2000;20(7):776-86.
Lepore et al., Recent advances in heterolytic nucleofugal leaving groups. Tetrahedron. Jun. 11, 2007;63(24):5103-5122.
Liang et al., Decreased adrenergic neuronal uptake activity in experimental right heart failure. A chamber-specific contributor to beta-adrenoceptor downregulation. J Clin Invest. Oct. 1989;84(4):1267-75.
Loc'H et al., Preparation and pharmacological characterization of [76Br]-meta-bromobenzylguanidine ([76Br]MBBG). Nucl Med Biol. Jan. 1994;21(1):49-55.
Lothian et al., Rapid fluorodesilylation of aryltrimethylsilanes using xenon difluoride: an efficient new route to aromatic fluorides. Synlett. Oct 1993:753-5.
Lulinski et al., Eco-friendly oxidative iodination of various arenes with a urea-hydrogen peroxide adduct (UHP) as the oxidant. Synthesis. 2004; (3):441-45.
Maddahi et al., Phase I, first-in-human study of BMS747158, a novel 18F-labeled tracer for myocardial perfusion PET: dosimetry, biodistribution, safety, and imaging characteristics after a single injection at rest. J Nucl Med. Sep. 2011;52(9):1490-8. Epub Aug. 17, 2011.
Martinez-Barrasa et al., Pyridinium N-(2'-Azinyl)Aminides: Regioselective Synthesis of 2-Alkylaminoazines. Tetrahedron. 2000;56:2481-90.
Matsunari et al., Iodine-123 metaiodobenzylguanidine imaging and carbon-11 hydroxyephedrine positron emission tomography compared in patients with left ventricular dysfunction. Circ Cardiovasc Imaging. Sep. 2010;3(5):595-603. Epub Jun. 9, 2010.
Matsunari et al., Phantom studies for estimation of defect size on cardiac (18)F SPECT and PET: implications for myocardial viability assessment. J Nucl Med. Oct. 2001;42(10):1579-85.
Menzel et al., An improved method for the bromination of metalated haloarenes via lithium, zinc transmetalation: a convenient synthesis of 1,2-dibromoarenes. J Org Chem. Mar. 3, 2006;71(5):2188-91.
Minardo et al., Scintigraphic and electrophysiological evidence of canine myocardial sympathetic denervation and reinnervation produced by myocardial infarction or phenol application. Circulation. Oct. 1988;78(4):1008-19.
Mitani et al., $^{123}$I-MIBG myocardial imaging in hypertensive patients: abnormality progresses with left ventricular hypertrophy. Ann Nucl Med. Aug. 1996;10(3):315-21.
Mitrani et al., Regional cardiac sympathetic denervation in patients with ventricular tachycardia in the absence of coronary artery disease. J Am Coll Cardiol. Nov. 1, 1993;22(5):1344-53.
Münch et al., Cardiac overexpression of the norepinephrine transporter uptake-1 results in marked improvement of heart failure. Circ Res. Oct. 28, 2005;97(9):928-36. Epub Sep. 15, 2005.
Münch et al., Evaluation of sympathetic nerve terminals with [(11)C]epinephrine and [(11)C]hydroxyephedrine and positron emission tomography. Circulation. Feb. 8, 2000;101(5):516-23.
Murphy et al., Meta halogenation of 1,3-disubstituted arenes via iridium-catalyzed arene borylation. J Am Chem Soc. Dec. 19, 2007;129(50):15434-5. Epub Nov. 21, 2007.
Nakajo et al., Iodine-131 metaiodobenzylguanidine intra- and extravesicular accumulation in the rat heart. J Nucl Med. Jan. 1986;27(1):84-9.

(56) References Cited

OTHER PUBLICATIONS

Namavari et al., Regioselective radiofluorodestannylation with [$^{18}$F]F$_2$ and [$^{18}$F]CH$_3$COOF: a high yield synthesis of 6-[$^{18}$F]Fluoro-L-dopa. Int J Rad Appl Instrum A. Aug. 1992;43(8):989-96.

Nattel, The molecular and ionic specificity of antiarrhythmic drug actions. J Cardiovasc Electrophysiol. Feb. 1999;10(2):272-82.

Nekolla et al., Evaluation of the novel myocardial perfusion positron-emission tomography tracer 18F-BMS-747158-02: comparison to 13N-ammonia and validation with microspheres in a pig model. Circulation. May 5, 2009;119(17):2333-42. Epub Apr. 20, 2009.

Netscher, Sulfonate leaving groups for nucleophilic substitution reactions—improved structures and procedures. Recent Res Dev Org Chem. 2003;7:71-83.

Odaka et al., Reappearance of cardiac presynaptic sympathetic nerve terminals in the transplanted heart: correlation between PET using (11)C-hydroxyephedrine and invasively measured norepinephrine release. J Nucl Med. Jul. 2001;42(7):1011-6.

Ozawa et al., Pharmacological properties of heterocyclic amidine derivatives. II. Pharmacological studies of phenylguanylpiperazine derivatives. Chem Pharm Bull (Tokyo). Dec. 1968;16(12):2482-7.

Packer, The neurohormonal hypothesis: a theory to explain the mechanism of disease progression in heart failure. J Am Coll Cardiol. Jul. 1992;20(1):248-54.

Paik et al., Validation of $^{18}$F Fluoropropyl-benzylguanidine as a novel positron emitting analogue of MIBG. J Nucl Med. 2002;43:363P. No. 1460.

Pauwels et al., Fluorine-18-radiolabeled pharmaceuticals for imaging with positron emission tomography, excluding [18F]-fluorodeoxyglucose. Drugs of the Future. 2002;27:655-67.

Pietilä et al., Reduced myocardial carbon-11 hydroxyephedrine retention is associated with poor prognosis in chronic heart failure. Eur J Nucl Med. Mar. 2001;28(3):373-6.

Pike et al., Reactions of cyclotron-produced [18F]fluoride with diaryliodonium salts—a novel single-step route to no-carrier-added [18] fluoroarenes. J Chem Soc., Chem Commun. 1995:2215-6.

Podrid et al., Role of the sympathetic nervous system in the genesis of ventricular arrhythmia. Circulation. Aug. 1990;82(2 Suppl):I103-13.

Prakash et al., N-halosuccinimide/BF3—H2O, efficient electrophilic halogenating systems for aromatics. J Am Chem Soc. Dec. 8, 2004;126(48):15770-6.

Qin et al., Iodine-Mediated Guanidine Formation through Arylsulfonyl-Activated Thioureas. Synlett. 2009. Advanced Online Publication. 4 pages.

Raffel et al., Assessment of cardiac sympathetic nerve integrity with positron emission tomography. Nucl Med Biol. Jul. 2001;28(5):541-59.

Raffel et al., Influence of Vesicular Storage and Monoamine Oxidase Activity on [$^{11}$C]Phenylephrine Kinetics: Studies in Isolated Rat Heart. J Nucl Med. 1990;40:323-30.

Raffel et al., Radiolabeled phenethylguanidines: novel imaging agents for cardiac sympathetic neurons and adrenergic tumors. J Med Chem. May 3, 2007;50(9):2078-88. Epub Apr. 10, 2007.

Rajesh et al., Bromination of deactivated aromatics: a simple and efficient method. J Org Chem. Jul. 20, 2007;72(15):5867-9. Epub Jun. 23, 2007.

Reifenrath et al., Synthesis and biological activity of fluoroalkylamine derivatives of narcotic analgesics. J Med Chem. Sep. 1980;23(9):985-90.

Rimoldi et al., Basal and hyperaemic myocardial blood flow in regionally denervated canine hearts: an in vivo study with positron emission tomography. Eur J Nucl Med Mol Imaging. Feb. 2007;34(2):197-205. Epub Sep. 2, 2006.

Rise et al., Sodium 2-Mercaptoethanesulfonate in Reversible Adduct Formation and Water Solubilization. Acta Chemica Scandinavica. 1989;43:489-92.

Ross et al., Nucleophilic 18F-fluorination of heteroaromatic iodonium salts with no-carrier-added [18F]fluoride. J Am Chem Soc. Jun. 27, 2007;129(25):8018-25. Epub May 31, 2007.

Rundqvist et al., Increased cardiac adrenergic drive precedes generalized sympathetic activation in human heart failure. Circulation. Jan. 7, 1997;95(1):169-75.

Sakata et al., Cardiac sympathetic nervous system in early essential hypertension assessed by $^{123}$I-MIBG. J Nucl Med. Jan. 1999;40(1):6-11.

Sasano et al., Abnormal sympathetic innervation of viable myocardium and the substrate of ventricular tachycardia after myocardial infarction. J Am Coll Cardiol. Jun. 10, 2008;51(23):2266-75.

Scholte et al., Cardiac autonomic neuropathy in patients with diabetes and no. symptoms of coronary artery disease: comparison of 123I-metaiodobenzylguanidine myocardial scintigraphy and heart rate variability. Eur J Nucl Med Mol Imaging. Aug. 2010;37(9):1698-705. Epub Apr. 22, 2010.

Schwartz, The autonomic nervous system and sudden death. Eur Heart J. Jun. 1998;19 Suppl F:F72-80.

Shah et al., The synthesis of [18F]fluoroarenes from the reaction of cyclotron-produced [18F]fluoride ion with diaryliodonium salts. J Chem Socs, Perkin Trans 1. 1998;2043-6.

Sherif et al., Evaluation of a novel (18)F-labeled positron-emission tomography perfusion tracer for the assessment of myocardial infarct size in rats. Circ Cardiovasc Imaging. Mar. 2009;2(2):77-84. Epub Jan. 26, 2009.

Schoster et al., Contributions to the coordination chemistry of technetium. J Radioanalytical Nuclear Chem. 1996;211(2):403-24.

Simões et al., Presence of sympathetically denervated but viable myocardium and its electrophysiologic correlates after early revascularised, acute myocardial infarction. Eur Heart J. Apr. 2004;25(7):551-7.

Smith et al., Autonomic tone attenuates drug-induced QT prolongation. J Cardiovasc Electrophysiol. Sep. 2007;18(9):960-4. Epub Jul. 30, 2007.

Stevens et al., Cardiac sympathetic dysinnervation in diabetes: implications for enhanced cardiovascular risk. Circulation. Sep. 8, 1998;98(10):961-8.

Stoll et al., Application of n.c.a. 4[$^{18}$F]fluorophenol in diaryl ether syntheses of 2-(4-[$^{18}$F]fluorophenoxy)-benzylamines. J Labelled Comp Radiopharm. 2004;47:443-55.

Sun et al., Room-temperature nucleophilic aromatic fluorination: experimental and theoretical studies. Angew Chem Int Ed Engl. Apr. 21, 2006;45(17):2720-5.

Thiebes et al., Mild preparation of haloarenes by ipso-substitution of arylboronic acids with N-halosuccinimides. Synlett. Feb. 1998:141-42.

Thompson et al., The conversion of phenols to the corresponding aryl halides under mild conditions. Synthesis. 2005; (4)547-50.

Tius et al., Synthetic communications: an international journal for rapid communication of synthetic organic chemistry. Synth Commun. 1992;22(10):1461-71.

Travin, Cardiac neuronal imaging at the edge of clinical application. Cardiol Clin. May 2009;27(2):311-27.

Vaidyanathan et al., (4-[18F]fluoro-3-iodobenzyl)guanidine, a potential MIBG analogue for positron emission tomography. J Med Chem. Oct. 14, 1994;37(21):3655-62.

Vaidyanathan et al., No-carrier-added iodine-131-FIBG: evaluation of an MIBG analog. J Nucl Med. Feb. 1997;38(2):330-4.

Vaidyanathan et al., No-carrier-added synthesis of a 4-methyl-substituted meta-iodobenzylguanidine analogue. Appl Radiat Isot. Mar. 2005;62(3):435-40.

Vaidyanathan et al., Biological evaluation of ring- and side-chain-substituted m-odobenzylguanidine analogues. Bioconjug Chem. Sep.-Oct. 2001;12(5):798-806.

Vaidyanathan et al., Validation of 4[fluorine-18]fluoro-3-iodobenzylguanidine as a positron-emitting analog of MIBG. J Nucl Med. Apr. 1995;36(4):644-50.

Valette et al., Bromine-76-metabromobenzylguanidine: a PET radiotracer for mapping sympathetic nerves of the heart. J Nucl Med. Oct. 1993;34(10):1739-44.

Watson et al., Formation of ArF from LPdAr(F): catalytic conversion of aryl triflates to aryl fluorides. Science. Sep. 25, 2009;325(5948):1661-4. Epub Aug. 13, 2009. Erratum: Jul. 2, 2010.

(56) References Cited

OTHER PUBLICATIONS

Wieland et al., Adrenal medulla 1,2,7,11 imaging agents: a structure-distribution relationship study of radiolabeled aralkylguanidines. J Medic Chem. Feb. 1, 1984;27(2):149-55.

Wiesel et al., The Transport of Tyrosine into the Human Brain as Determined with L-[1-11C]Tyrosine and PET. J Nucl Med. 1991;32:2043-49.

Wilen et al., Strategies in Optical Resolutions. Tetrahedron. 1977;33:2725-36.

Wilen, Tables of Resolving Agents and Optical Resolutions. E.L. Eliel, ed. Universtify of Notre Dame Press, Notre Dame, IN. 1972:268-98.

Yamada et al., Convenient electrophilic fluorination of functionalized aryl and heteroaryl magnesium reagents. Angew Chem Int Ed Engl. Mar. 15, 2010;49(12):2215-8.

Yu et al., BMS-747158-02: a novel PET myocardial perfusion imaging agent. J Nucl Cardiol. Nov.-Dec. 2007;14(6):789-98. Epub Oct. 22, 2007.

Yu et al., Cardiac imaging and safety evaluation of BMS747158, a novel PET myocardial perfusion imaging agent, in chronic myocardial compromised rabbits. J Nucl Cardiol. Aug. 2010;17(4):631-6. Epub Mar. 26, 2010.

Yu et al., Evaluation of LMI1195, a novel 18F-labeled cardiac neuronal PET imaging agent, in cells and animal models. Circ Cardiovasc Imaging. Jul. 2011;4(4):435-43. Epub May 9, 2011.

Yu et al., LMI1195: A New 18F Benzylguanidine Analog for PET Cardiac Sympathetic Neuronal Imaging. AHA Scientific Session 2009. Orlando, FL. Nov. 15-17, 2009. Abstract Only.

Yu et al., The next generation of cardiac positron emission tomography imaging agents: discovery of flurpiridaz F-18 for detection of coronary disease. Semin Nucl Med. Jul. 2011;41(4):305-13. doi: 10.1053/j.semnuclmed.2011.02.004.

Zhdankin et al., Chemistry of polyvalent iodine. Chem Rev. Dec. 2008;108(12):5299-358.

Zhou et al., An efficient and regioselective monobromination of electron-rich aromatic compounds using catalytic hypervalent iodine (III) reagent. Synthesis. 2011;(2):207-09.

Zipes, Cardiac Electrophysiology: From Cell to Bedside. Zipes et al., eds. W.B. Saunders, Philadelphia. 1995:441-53.

Remington's Pharmaceutical Science. 1995; 19th Edition. Volume 1. Gennaro, ed. Chapter 48: The Introduction of New Drugs: 795-808.

Bozek et al., Roles of Cardiac Norepinephrine Uptake 1 and 2 in Evaluation of LMI1195, a New Cardiac PET Neuronal Imaging Agent, in Rats, Rabbits and Nonhuman Primates. Nuc Med (Society of Nuclear Medicine Annual Meeting Abstracts). 2011;52(S1):1099.

Estep et al., Indole Resin: A Versatile New Support for the Solid-Phase Synthesis of Organic Molecules. J Org Chem. 1998;63(16):5300-1.

Gaertner et al., Preclinical In Vivo Imaging of Pheochromocytoma using the MIBG-Analog PET tracer [18F]LMI1195. Eur J Nuc Med Mol Imag. 2013;40:S152-3. OP253.

Higuchi et al., F-18 Labeled PET Tracer LMI1195 for Imaging Norepinephrine Handling in Rat Hearts. J Nuc Med (Society of Nuclear Medicine Annual Meeting Abstracts). 2012;53(S1):1771.

Higuchi et al., Myocardial Kinetics of Novel F-18 Sympathetic Nerve Tracer LMI1195 in the Isolated Working Rabbit Heart. J Nuc Med (Society of Nuclear Medicine Annual Meeting Abstracts). 2013;54(S2):130.

Kagan et al., LMI1195 and Flurpiridaz F 18 PET Imaging in Evaluation of Time-Course Changes in Mismatch of Cardiac Denervated and Perfusion Defect Areas Following Acute Myocardial Infarction. J Nuc Med (Society of Nuclear Medicine Annual Meeting Abstracts). 2012;53(S1):84.

Ramsay et al., Interaction of 1-methyl-4-phenylpyridinium ion (MPP+) and its analogs with the rotenone/piericidin binding site of NADH dehydrogenase. J Neurochem. Apr. 1991;56(4)1184-90.

Robinson, The Next Generation of PET Cardiac Imaging Agents: Discovery of Flurpiridaz F 18 for Detection of Coronary Artery Disease and LMI1195 for Sympathetic Neuronal Imaging. Drugs of the Future. 2010;35:29.

Sinusas et al., Biodistribution and radiation dosimetry of LMI1195: first-in-human study of a novel 18F-labeled tracer for imaging myocardial innervation. J Nucl Med. Sep. 2014;55(9):1445-51. doi:10.2967/jnumed.114.140137. Epub Jul. 3, 2014.

Ueno et al., Comparison of the inhibitory action of natural rotenone and its stereoisomers with various NADH-ubiquinone reductases. Eur J Biochem. Oct. 1, 1994;225(1):411-7.

Ueno et al., Structural factors of rotenone required for inhibition of various NADH-ubiquinone oxidoreductases. Biochim Biophys Acta. Sep. 30, 1996;1276(3):195-202.

Wu et al., Studies on Synthesis of the new Precursors of 18F Labelled Amino Acids Radiopharmaceuticals for Positron Emission Tomography. Chinese Doctoral Dissertations Full-text Database (Medicine and Health Sciences). 2009;7:E79-12, pp. 7-10.

Yu et al., LMI1195 PET Neuronal Imaging: Evaluation of Cardiac Denervation, Re-innervation and Associated Susceptibility to Arrhythmia. J Nuc Med (Society of Nuclear Medicine Annual Meeting Abstracts). 2011;52(S1):1103.

Yu et al., LMI1195: A New 18F Benzylguanidine Analog for PET Cardiac Sympathetic Neuronal Imaging. J Am Col Card. 2010;55(10):A88.

Breidenbach, No-carrier-added labelled 6-aminopurine derivatives as potential adensine A2A-receptorligands for positron-emission-tomography. Berichte des Forschungszentrums Juelich. 2004;4132:134 pages.

Broekema et al., Synthesis of leukotriene B4 antagonists labeled with In-111 or Tc-99m to image infectious and inflammatory foci. J Med Chem. Oct. 6, 2005;48(20):6442-53.

Chu et al., Synthesis and biodistribution of (99m)Tc-carbonyltechnetium-labeled fatty acids. Appl Radiat Isot. Jun. 2004;60(6):845-50.

Jang et al., 4-[18F]Fluoro-m-hydroxyphenethylguanidine: a radiopharmaceutical for quantifying regional cardiac sympathetic nerve density with positron emission tomography. J Med Chem. Sep. 26, 2013;56(18):7312-23. doi: 10.1021/jm400770g. Epub Sep. 5, 2013.

Koehler et al., Radiosynthesis and radiopharmacological evaluation of cyclin-dependent kinase 4 (Cdk4) inhibitors. Eur J Med Chem. Feb. 2010;45(2):727-37. doi: 10.1016/j.ejmech.2009.11.020. Epub Nov. 24, 2009.

March, Advanced Organic Chemistry. 1992; 4th Edition. John Wiley & Sons: p. 431.

Robins et al., Synthesis and in vitro evaluation of (18)F-labelled S-fluoroalkyl diarylguanidines: Novel high-affinity NMDA receptor antagonists for imaging with PET. Bioorg Med Chem Lett. Mar. 1, 2010;20(5):1749-51. doi: 10.1016/j.bmcl.2010.01.052. Epub Jan. 20, 2010.

Wang et al., Synthesis and preliminary biological evaluation of O6-[4-(2-[18F]fluoroethoxymethyl)benzyl]guanine as a novel potential PET probe for the DNA repair protein O6-alkylguanine-DNA alkyltransferase in cancer chemotherapy. Biorg Med Chem. Oct. 15, 2005;13(20):5779-86.

\* cited by examiner

COMPOSITIONS, METHODS, AND SYSTEMS FOR THE SYNTHESIS AND USE OF IMAGING AGENTS

RELATED APPLICATIONS

The present application is a national stage filing under 35 U.S.C. §371 of International Application No. PCT/US2011/036142, filed on May 5, 2011, entitled "Compositions, Methods, and Systems for the Synthesis and Use of Imaging Agents, which claims priority under 35 U.S.C. §119(e) to U.S. provisional application, U.S. Ser. No. 61/333,618, filed May 11, 2010, entitled "Compositions, Methods, and Systems For Imaging Heart Failure"; U.S. provisional application, U.S. Ser. No. 61/405,524, filed Oct. 21, 2010, entitled "Compositions, Methods, and Systems For Imaging Heart Failure"; and U.S. provisional application, U.S. Ser. No. 61/405,571, filed Oct. 21, 2010, entitled "Synthetic Methods, Salts, and Compositions for Imaging", each of which is incorporated herein by reference.

FIELD OF THE INVENTION

The present invention relates to systems, compositions, methods, and apparatuses for synthesizing imaging agents and precursors thereof.

BACKGROUND OF THE INVENTION

Heart failure (HF) is defined as the inability of the heart to supply peripheral organs with sufficient blood flow. It may be characterized by a hyperadrenergic state whereby increased systemic levels of norepinephrine (NE) and increased local spillover of catecholamines occurs. The condition afflicts increasingly more people each year and is a common end-stage of many cardiac diseases and conditions including myocardial infarction, pressure/volume overload, viral myocarditis, toxic cardiomyopathy, valve failure, and other abnormalities. The resultant myocardial damage, in conjunction with neurohormonal and cytokine activation, stimulates chamber remodeling which is the initial phase of HF development. The remodeling process results in decreased overall myocardial efficiency and eventual progression to clinical HF. To date, no cure for the condition exists, thus early diagnosis is a key factor in its management and long-term prognosis. An imaging agent that identifies subjects in early HF would thus enable treatment application and life-style improvements for patients living with the condition.

Accordingly, improved methods, systems, and apparatuses are needed for the synthesis and administration of imaging agents (e.g., for imaging the heart). In addition, while numerous synthetic methods exist for the preparation of PET-based imaging agents, they generally require multiple synthetic (e.g., labeling a compound with an imaging moiety) and/or purification steps, have low chemical fidelity, and/or have low chemical efficiency. Improved synthetic methods and compositions are thus needed for preparing such compounds.

SUMMARY OF THE INVENTION

The invention provides, in a broad sense, methods for synthesizing imaging agents and their precursors, compounds (including salt forms) that are imaging agent precursors or imaging agents, and methods of use thereof.

In one aspect, the invention provides compositions. In some embodiments, a composition comprises a compound comprising formula (II):

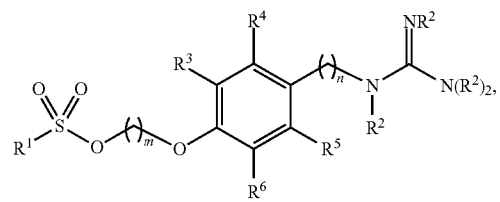

or a salt, free base, or combination thereof, wherein $R^1$ is alkyl, haloalkyl, alkynyl, alkenyl, heteroalkyl, cycloalkyl, aryl, heteroaryl, arylalkyl, heterocyclyl, or heteroarylalkyl, each optionally substituted; each $R^2$ can be the same or different and is hydrogen or a nitrogen-protecting group; $R^3$, $R^4$, $R^5$, and $R^6$ can be the same or different and are individually hydrogen, $C_1$-$C_6$ alkyl, heteroalkyl, halide, —$OR^7$, —$SR^7$, —$N(R^7)_2$, or —$C(=O)R^8$, each optionally substituted; each $R^7$ can be the same or different and is hydrogen, alkyl, heteroalkyl, cycloalkyl, heterocyclyl, haloalkyl, aryl, or heteroaryl, each optionally substituted; each $R^8$ can be the same or different and is hydrogen, alkyl, heteroalkyl, cycloalkyl, haloalkyl, heterocyclyl, aryl, heteroaryl, —OH, alkoxy, —$NH_2$, alkylamino, —SH, or alkylthiol, each optionally substituted; m is an integer between 1 and 12, inclusive; and n is an integer between 1 and 4, inclusive.

In some embodiments, a compound of formula (II) comprises the structure of formula (IV):

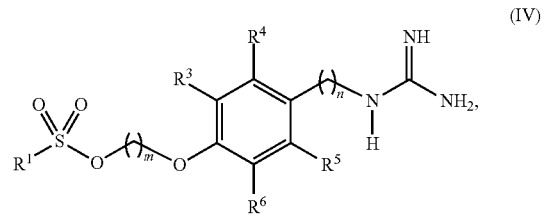

or a salt, free base, or combination thereof.

In some embodiments, a compound of formula (IV) comprises formula (III):

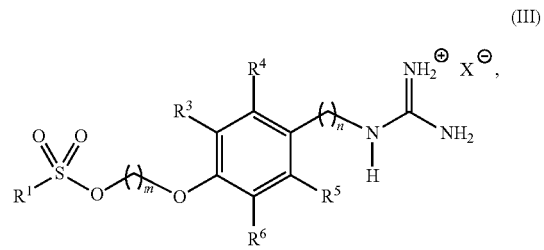

wherein $X^\ominus$ is a counter anion. In some embodiments, $X^\ominus$ is halide, phosphate, sulfate, trifluoroacetate, toluenesulfonate, acetate, formate, citric, ascorbate, mesylate (methanesulfonate), or benzoate.

In some embodiments, a compound of formula (II) comprises the formula:

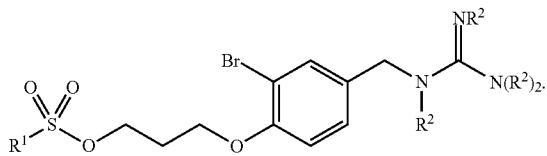

In some embodiments, for any of the composition described above, at least one $R^2$ is not hydrogen.

In some embodiments, a compound of formula (II) comprises the formula:

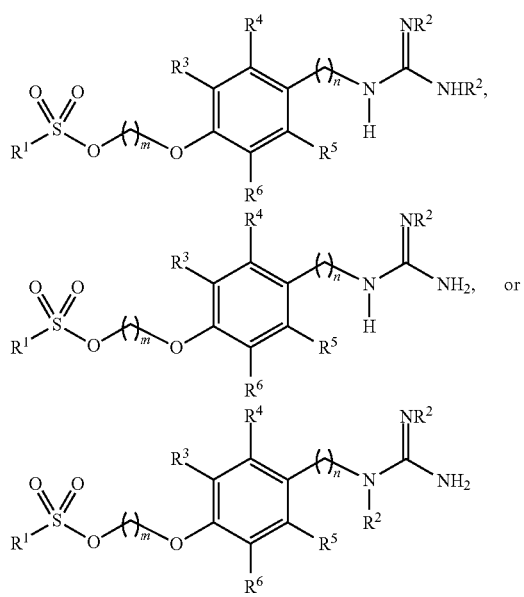

or a salt, free base, or combination thereof.

In some embodiments, a compound of formula (II) comprises the formula:

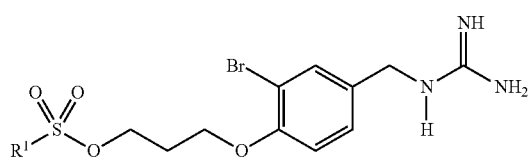

or a salt, free base, or combination thereof.

In some embodiments, m is 3. In some embodiments, n is 1. In some embodiments, $R^3$ is Br. In some embodiments, $R^1$ is $C_1$-$C_6$ alkyl, haloalkyl, or aryl. In some embodiments, $R^1$ is methyl, ethyl, n-propyl, i-propyl, n-butyl, i-butyl, t-butyl, pentyl, or hexyl. In some embodiments, $R^1$ is haloalkyl. In some embodiments, $R^1$ is $CF_3$. In some embodiments, $R^1$ is phenyl (Ph), optionally substituted. In some embodiments, $R^1$ is 4-$CH_3$Ph, 2,4,6-$(CH_3)_3C_6H_2$, or $C_6H_4X$, wherein X is halide. In some embodiments, m is an integer between 1 and 10, inclusive; or between 1 and 8, inclusive; or between 1 and 6, inclusive. In some embodiments, $R^4$, $R^5$, and $R^6$ are hydrogen; and $R^3$ is halide (e.g., Br). In some embodiments, the composition comprises a salt of the compound of formula (II). In some embodiments, the salt is a pharmaceutically acceptable salt. In some embodiments, at least one $R^2$ is t-butyloxycarbonyl.

In one aspect, the invention provides a compound comprising formula:

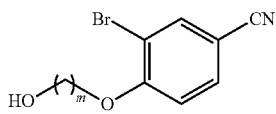

or a salt thereof, wherein m is an integer between 2 and 12, inclusive. In certain embodiments, m is an integer between 3 and 12, inclusive. In one embodiment, m is 3.

In one embodiment, the invention provides a compound having a structure of:

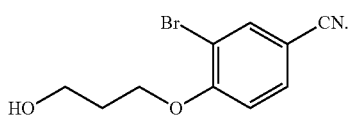 [SMILES: N#Cc1ccc(OCCCO)c(Br)c1]

In one aspect, the invention provides a compound comprising formula:

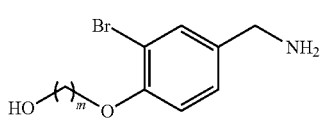

or a salt, free base, or combination thereof, wherein m is an integer between 2 and 12, inclusive. In certain embodiments, m is an integer between 3 and 12, inclusive. In one embodiment, m is 3.

In one embodiment, the invention provides a compound having a structure of

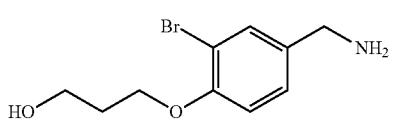 [SMILES: NCc1ccc(OCCCO)c(Br)c1]

or a free base, salt, or combination thereof.

In one aspect, the invention provides a compound comprising formula:

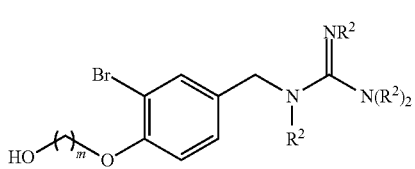

or a salt, free base, or combination thereof; wherein each $R^2$ can be the same or different and is hydrogen or a nitrogen-protecting group; and m is an integer between 2 and 12, inclusive. In certain embodiments, m is an integer between 3 and 12, inclusive. In one embodiment, m is 3.

In certain embodiments, the invention provides a compound comprising formula:

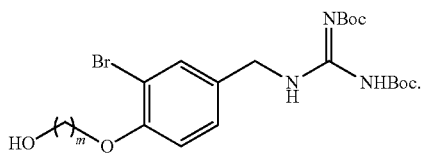

In certain embodiments, the invention provides a compound having a structure of

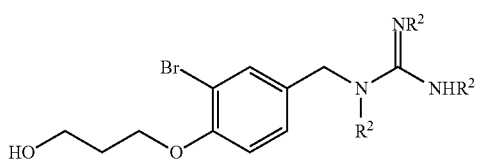

wherein R² can be the same or different and is hydrogen or a nitrogen-protecting group.

In one embodiment, the invention provides a compound having a structure of

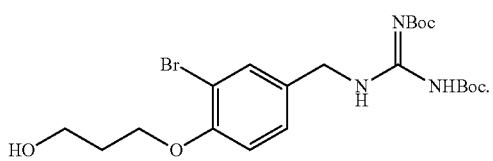

In one embodiment, the invention provides a compound having a structure of

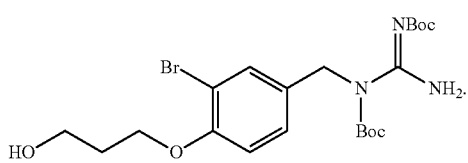

In one aspect, the invention provides a method comprising reducing a compound comprising formula:

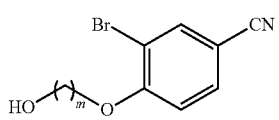

or a salt thereof, wherein m is an integer between 3 and 12, inclusive, with a reductant under suitable conditions to form a compound comprising:

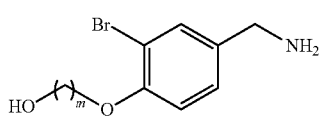

or a salt, free base, or combination thereof. In one embodiment, m is 3. In one embodiment, the reductant is BH₃.

In one aspect, the invention provides a method comprising reacting a compound comprising formula:

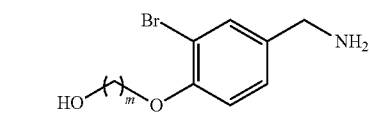

or a salt, free base, or combination thereof, wherein m is an integer between 2 and 12, inclusive; under conditions suitable to form a compound comprising formula:

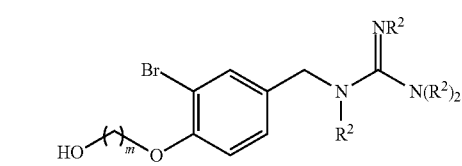

or a salt, free base, or combination thereof, wherein each R² can be the same or different and is hydrogen or a nitrogen-protecting group; and m is an integer between 2 and 12, inclusive. In certain embodiments, m is an integer between 3 and 12, inclusive. In one embodiment, m is 3. In one embodiment, the step of reacting comprises reacting a comprising formula:

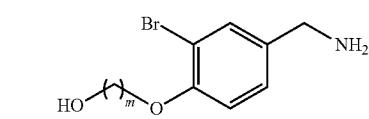

with a compound of formula:

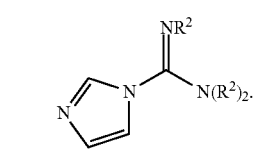

In one embodiment, the compound comprising formula:

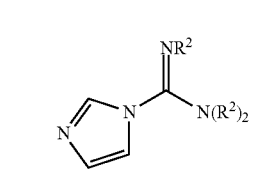

is of formula:

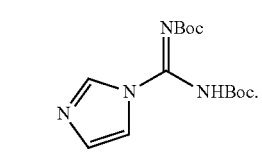

In one embodiment, the compound comprising formula:

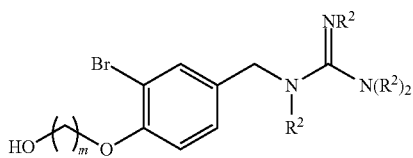

is of formula:

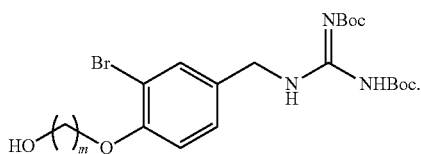

In other aspects, the invention provides compositions comprising one or more of any of the foregoing compounds, including free bases thereof, salts thereof, and combinations thereof.

In another aspect, the present invention provides methods for forming compounds. In a first embodiment, a method comprises reacting a compound comprising formula (II):

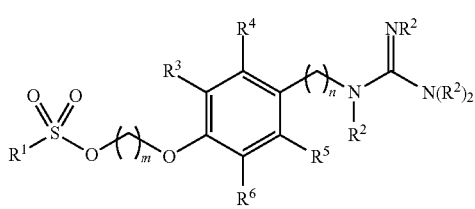

or a salt, free base, or combination thereof, under conditions suitable to form a compound comprising formula (IV):

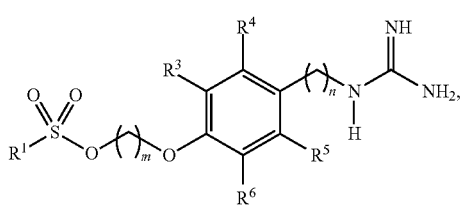

or a salt, free base, or combination thereof, wherein $R^1$ is alkyl, heteroalkyl, cycloalkyl, aryl, heteroaryl, arylalkyl, heteroarylalkyl, alkenyl, alkynyl, heterocyclyl, or haloalkyl, each optionally substituted; each $R^2$ can be the same or different and is hydrogen or a nitrogen-protecting group, provided at least one $R^2$ is not hydrogen; $R^3$, $R^4$, $R^5$, and $R^6$ can be the same or different and are individually hydrogen, $C_1$-$C_6$ alkyl, heteroalkyl, halide, —$OR^7$, —SR', —$N(R^7)_2$, or —C(=O)$R^8$, each optionally substituted; each $R^7$ can be the same or different and is hydrogen, alkyl, heteroalkyl, cycloalkyl, haloalkyl, aryl, heteroaryl, or heterocyclyl, each optionally substituted; each $R^8$ can be the same or different and is hydrogen, alkyl, heteroalkyl, cycloalkyl, haloalkyl, heterocyclyl, aryl, heteroaryl, —OH, alkoxy, —$NH_2$, alkylamino, —SH, or alkylthiol, each optionally substituted; m is an integer between 1 and 12, inclusive; and n is an integer between 1 and 4, inclusive.

In another embodiment, a method comprises reacting a compound comprising formula (II):

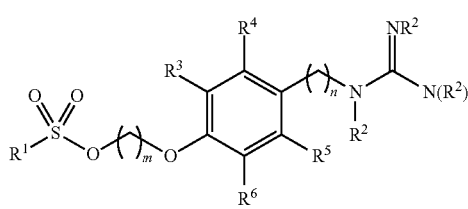

or a salt, free base, or combination thereof, under conditions suitable to form a compound comprising formula (I):

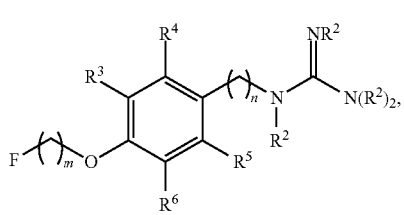

or a salt, free base, or combination thereof, wherein $R^1$ is alkyl, heteroalkyl, cycloalkyl, aryl, heteroaryl, arylalkyl, heterocyclyl, heteroarylalkyl, alkenyl, alkynyl, or haloalkyl, each optionally substituted; each $R^2$ can be the same or different and is hydrogen or a nitrogen-protecting group; $R^3$, $R^4$, $R^5$, and $R^6$ can be the same or different and are individually hydrogen, $C_1$-$C_6$ alkyl, heteroalkyl, halide, —$OR^7$, —$SR^7$, —$N(R^7)_2$, or —C(=O)$R^8$, each optionally substituted; each $R^7$ can be the same or different and is hydrogen, alkyl, heteroalkyl, cycloalkyl, haloalkyl, aryl, heteroaryl, or heterocyclyl, each optionally substituted; each $R^8$ can be the same or different and is hydrogen, alkyl heteroalkyl, cycloalkyl, haloalkyl, heterocyclyl, aryl, heteroaryl, —OH, alkoxy, —$NH_2$, alkylamino, —SH, or alkylthiol, each optionally substituted; m is an integer between 1 and 12, inclusive; and n is an integer between 1 and 4, inclusive.

In some embodiments, the method further comprises reacting the compound comprising formula (I):

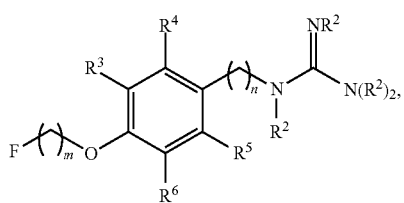

or a salt, free base, or combination thereof, provided at least one $R^2$ is not H, under conditions suitable to form a compound comprising formula (V):

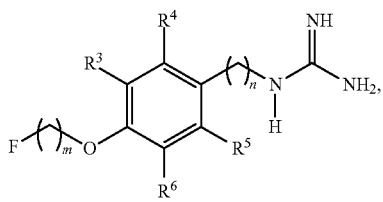

(V)

or a salt, free base, or combination thereof.

In yet another embodiment, a method comprises reacting a compound comprising formula (IV):

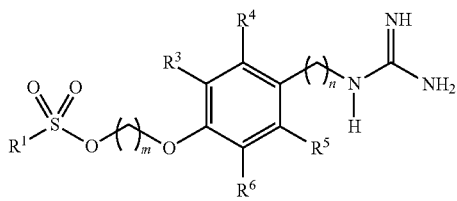

(IV)

or a salt, free base, or combination thereof, under conditions suitable to form a compound comprising formula (V):

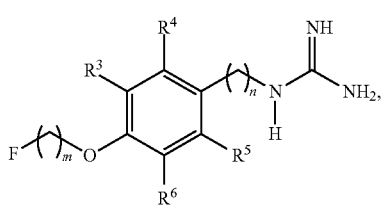

(V)

or a salt, free base, or combination thereof, wherein $R^1$ is alkyl, heteroalkyl, cycloalkyl, aryl, heteroaryl, heterocyclyl, arylalkyl, heteroarylalkyl, alkenyl, alkynyl, or haloalkyl, each optionally substituted; $R^3$, $R^4$, $R^5$, and $R^6$ can be the same or different and are individually hydrogen, $C_1$-$C_6$ alkyl, heteroalkyl, halide, —$OR^7$, —$SR^7$, —$N(R^7)_2$, or —$C(\!=\!O)R^8$, each optionally substituted; each $R^7$ can be the same or different and is hydrogen, alkyl, heteroalkyl, cycloalkyl, haloalkyl, aryl, heteroaryl, or heterocyclyl, each optionally substituted; each $R^8$ can be the same or different and is hydrogen, alkyl, heteroalkyl, cycloalkyl, haloalkyl, heterocyclyl, aryl, heteroaryl, —OH, alkoxy, —$NH_2$, alkylamino, —SH, or alkylthiol, each optionally substituted; m is an integer between 1 and 12, inclusive; and n is an integer between 1 and 4, inclusive.

In some embodiments, a compound of formula (II) comprises formula (IV):

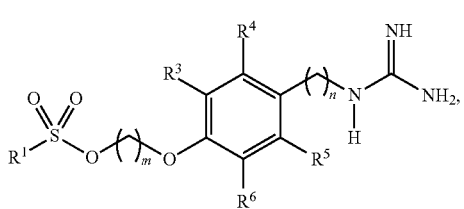

(IV)

or a salt, free base, or combination thereof.

In some embodiments, a compound of formula (IV) comprises formula (III):

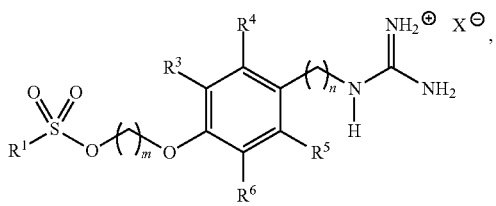

(III)

wherein $X^\ominus$ is a counter anion. In some embodiments, $X^\ominus$ is halide, phosphate, sulfate, trifluoroacetate, toluenesulfonate, acetate, formate, citrate, ascorbate, mesylate (methanesulfonate), or benzoate.

In some embodiments, a compound of formula (II) comprises the formula:

or a salt, free base, or combination thereof.

In some embodiments, at least one $R^2$ is not hydrogen, optionally, wherein at least one $R^2$ is t-butyloxycarbonyl. In some embodiments, the compound of formula (II) comprises the formula:

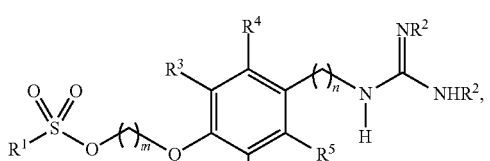

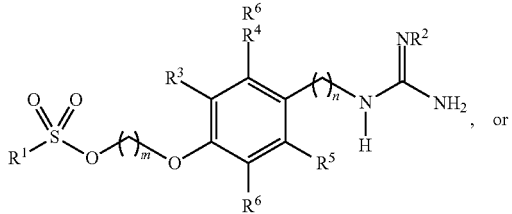

, or

-continued

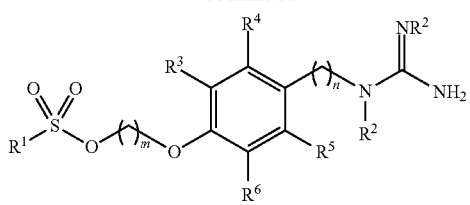

or a salt, free base, or combination thereof.

In some embodiments, a compound of formula (II) comprises the formula:

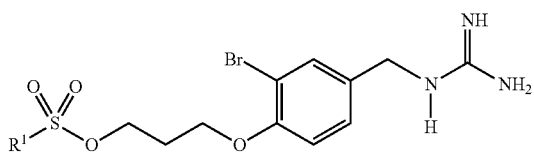

or a salt, free base, or combination thereof.

In some embodiments, m is 3. In some embodiments, m is an integer between 3 and 12, inclusive. In some embodiments, $R^3$ is halide; and $R^4$-$R^6$ are hydrogen. In some embodiments, $R^3$ is Br. In some embodiments, $R^1$ is $C_1$-$C_6$ alkyl, haloalkyl, or aryl. In some embodiments, $R^1$ is methyl, ethyl, n-propyl, i-propyl, n-butyl, i-butyl, t-butyl, pentyl, or hexyl. In some embodiments, $R^1$ is haloalkyl. In some embodiments, $R^1$ is $CF_3$. In some embodiments, $R^1$ is phenyl (Ph), optionally substituted. In some embodiments, $R^1$ is 4-$CH_3C_6H_4$, 2,4,6-$(CH_3)_3C_6H_2$, or $C_6H_4X$, wherein X is halide. In some embodiments, n is 1. In some embodiments, m is an integer between 1 and 10 inclusive, or between 1 and 8 inclusive, or between 1 and 6 inclusive. In some embodiments, F is isotopically enriched with $^{18}F$.

In one embodiment, a compound of formula (II) comprises the formula:

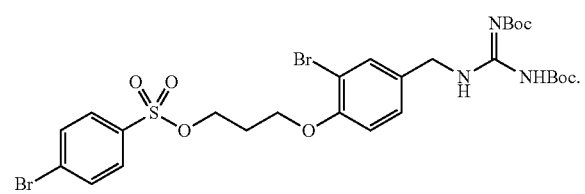

In one aspect, a compound of formula (II) comprises the formula:

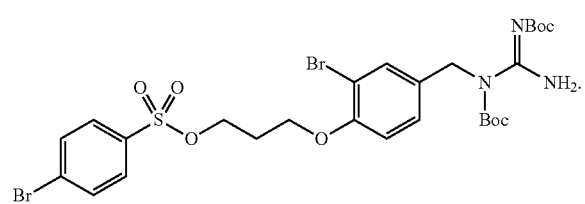

In one aspect, a compound of formula (II) comprises the formula

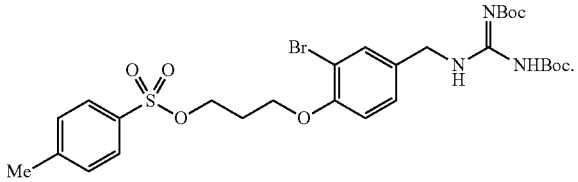

In one aspect, a compound of formula (II) comprises the formula:

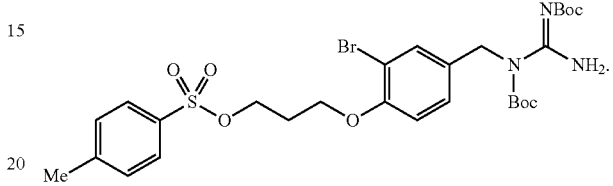

In some embodiments, a compound of formula (II) comprises the formula:

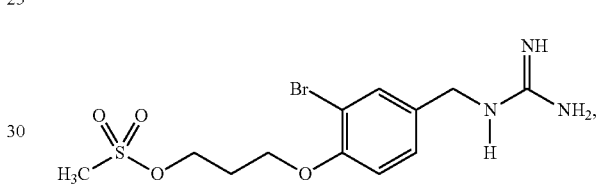

In some embodiments, a compound of formula (II) comprises the formula:

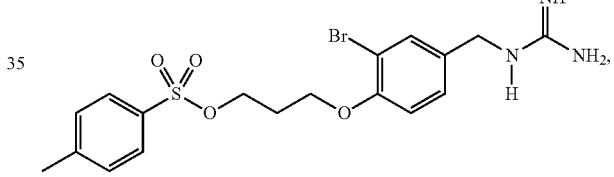

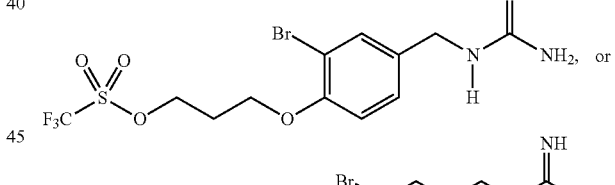

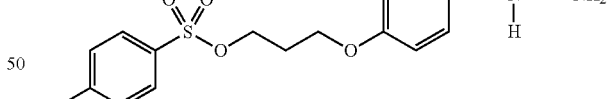

In some embodiments, the compound comprising formula (I), formula (II), and/or formula (IV) is provided as a solution in a solvent.

In some embodiments, the conditions suitable for deprotection comprise exposing the compound of formula (I) and/or formula (II) to an acid or to an acidic environment. In some embodiments, the acid is hydrochloric acid, formic acid, sulfuric acid, benzoic acid, acetic acid, trifluoroacetic acid, p-toluenesulfonic acid, phosphoric acid, or methanesulfonic acid. An acidic environment may be, for example, a pH equal to or less than 4, equal to or less than 3, equal to or less than 2, or equal to or less than 1.

In some embodiments, the suitable conditions comprise reacting at or above room temperature. In some embodiments, conditions suitable for deprotection and/or fluorination may comprise a temperature ranging from about 100° C. to about 150° C., including a temperature of about 100° C.

In some embodiments, the suitable conditions comprise reacting at a temperature of about 50° C., or about 60° C., or about 70° C., or about 80° C., or about 90° C., or about 100° C., or about 110° C., or about 120° C., or about 150° C., or about 170° C., or about 200° C., or about 225° C., or about 250° C. for a period of about 5 minutes or less, or about 10 minutes or less, or about 20 minutes or less, or about 30 minutes or less.

In some embodiments, the suitable conditions comprise a solution pH of equal to or less than about 13, or equal to or less than about 12, or equal to or less than about 11. In some embodiments, the suitable conditions comprise a solution pH of between about 8 and about 9, or between about 8 and about 10, or between about 7 and about 8. In some embodiments, conditions suitable for fluorination comprise a pH in the range of about 8-13, about 9-13, about 10-13, or about 10-12.

In some embodiments, the solvent is benzene, toluene, xylene, diethyl ether, glycol, diethyl ether, hexane, pentane, methylene chloride, chloroform, dioxane, tetrahydrofuran, ethyl acetate, water, or mixtures thereof. In some embodiments, the compound comprising formula (V) is isolated using column chromatography.

In some embodiments, the step of reacting comprises exposing a compound comprising formula (IV) to a source of fluoride. In some embodiments, the source of fluoride is isotopically enriched with $^{18}$F. In some embodiments, the source of fluoride is NaF or KF.

In some embodiments, the suitable conditions further comprise exposing a compound comprising Formula (II) or Formula (IV) to a source of fluoride in the presence of an ammonium salt or a bicarbonate salt. In some embodiments, the molar ratio of ammonium salt or bicarbonate salt to the compound of formula (IV) is less than or equal to about 10:1, or less than or equal to about 9:1, or less than or equal to about 8:1, or less than or equal to about 7:1 or less than or equal to about 6:1, or less than or equal to about 5:1, or less than or equal to about 4:1, or less than or equal to about 3:1, or less than or equal to about 2:1, or less than or equal to about 1:1. In some embodiments, the ammonium salt is an ammonium bicarbonate salt, ammonium hydroxide salt, ammonium acetate salt, ammonium lactate salt, ammonium trifluoroacetate salt, ammonium methanesulfonate salt, ammonium p-toluenesulfonate salt, ammonium nitrate salt, ammonium iodide salt, or ammonium bisulfate salt. In some embodiments, the bicarbonate salt is a tetraalkylammonium bicarbonate. In some embodiments, the ammonium salt or the bicarbonate salt comprises the formula:

wherein $R_4$ is alkyl. In some embodiments, the reacting is carried out in the presence of a cryptand.

In embodiments, a method comprises reacting a compound comprising formula (XI):

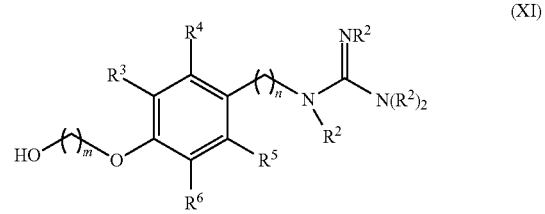

or a salt, free base, or combination thereof, under conditions suitable to form a compound comprising formula (II):

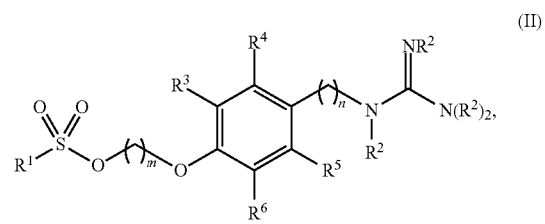

or a salt, free base, or combination thereof, wherein $R^1$ is alkyl, heteroalkyl, cycloalkyl, aryl, heteroaryl, arylalkyl, heteroarylalkyl, alkenyl, alkynyl, heterocyclyl, or haloalkyl, each optionally substituted; each $R^2$ can be the same or different and is hydrogen or a nitrogen-protecting group, provided at least one $R^2$ is not hydrogen; $R^3$, $R^4$, $R^5$, and $R^6$ can be the same or different and are individually hydrogen, $C_1$-$C_6$ alkyl, heteroalkyl, halide, —$OR^7$, —$SR^7$, —$N(R^7)_2$, or —$C(=O)R^8$, each optionally substituted; each $R^7$ can be the same or different and is hydrogen, alkyl, heteroalkyl, cycloalkyl, haloalkyl, aryl, heteroaryl, or heterocyclyl, each optionally substituted; each $R^8$ can be the same or different and is hydrogen, alkyl, heteroalkyl, cycloalkyl, haloalkyl, heterocyclyl, aryl, heteroaryl, —OH, alkoxy, —$NH_2$, alkylamino, —SH, or alkylthiol, each optionally substituted; m is an integer between 1 and 12, inclusive; and n is an integer between 1 and 4, inclusive.

In yet another aspect, the invention provides particular salts of imaging agents and/or their precursors. In one embodiment, a salt comprises formula (VI):

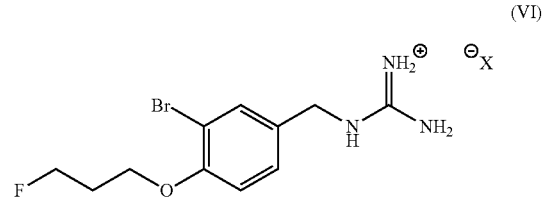

wherein $X^\ominus$ is formate.

In another embodiment, a salt comprises formula (VII):

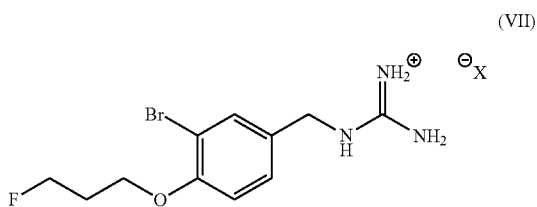

(VII)

wherein $X^{\ominus}$ is ascorbate.

In some embodiments, the salt is a citrate salt or a trifluoroacetate salt comprising the cation of formula (VI) or (VII).

In some embodiments, the fluorine of a salt is isotopically enriched with $^{18}F$.

In some embodiments, a pharmaceutically acceptable composition comprising a salt as described herein and optionally a pharmaceutically acceptable excipient is provided.

In some embodiments, a kit is provided comprising a salt or composition as described herein and instructions for use.

In another aspect, methods of imaging are provided. In one embodiment, a method of imaging a subject comprises administering a dose of a pharmaceutically acceptable composition comprising an imaging agent, including salts thereof, as described herein, wherein the fluorine is isotopically enriched with $^{18}F$, and optionally a pharmaceutically acceptable excipient, to a subject; and acquiring at least one image of a portion of the subject. In some embodiments, the maximum dose of the imaging agent is approximately 15 mCi or less, 14 mCi or less, 13 mCi or less, 12 mCi or less, 11 mCi or less or 10 mCi or less.

In one aspect, the invention provides use of a salt as described herein for imaging a portion of a subject.

In some embodiments, a method of imaging a subject is provided that comprises administering a dose of a compound comprising the formula:

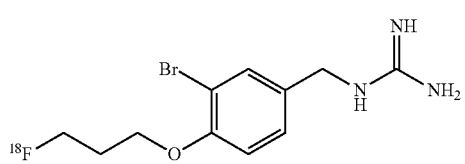 [SMILES: N=C(N)NCc1ccc(OCCC[18F])c(Br)c1]

or a free base, pharmaceutically acceptable salt, or combination thereof, to a subject, wherein the maximum dose of the compound administered to the subject is approximately 15 mCi or less; and acquiring at least one image of a portion of the subject.

In some embodiments, a method for detecting norepinephrine transporter (NET) in a portion of a subject is provided, the method comprising administering a dose of a compound comprising the formula:

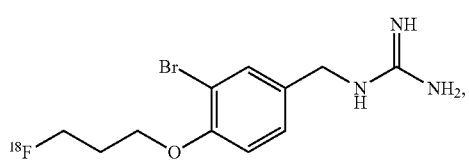 [SMILES: N=C(N)NCc1ccc(OCCC[18F])c(Br)c1]

or a free base, pharmaceutically acceptable salt, or combination thereof, to a subject, wherein the maximum dose of the compound administered to the subject is less than approximately 14 mCi; and acquiring at least one image of the portion of the subject, wherein the image detects NET in the subject.

In some embodiments, the maximum dose of the compound administered to the subject is approximately 13 mCi or less, is between approximately 10 mCi and approximately 13 mCi, or is between approximately 8 mCi and approximately 10 mCi.

In some embodiments, the step of acquiring employs positron emission tomography. In some embodiment, the portion of the subject being imaged is at least a portion of the cardiovascular system, the heart, or is at least a portion of the heart.

In some embodiments, the method further comprises determining the presence or absence of a cardiovascular disease or condition in the subject.

In some embodiments, the compound is provided for administration in a solution comprising between approximately 1% and approximately 10% ethanol and between approximately 25 mg/mL and approximately 75 mg/ml ascorbic acid.

In some embodiments, the method further comprises administering a second dose of the compound to the subject at a time subsequent to the first dose; and acquiring at least one image of the portion of the subject after the administration of the second dose of the compound. In some embodiments, the method further comprises comparing the at least one image acquired after the first dose with the at least one image acquired after the second dose; and determining the presence or absence of differences between the cardiac sympathetic innervation at the time of administration of the first and second dose of the compound to the subject.

In some embodiments, presence of NET indicates presence of a condition. In some embodiments, the condition is a tumor.

In some embodiments, the detecting comprises determining level, density, localization, and/or function of NET in the portion of the subject.

In some embodiments, the method further comprises assessing cardiac sympathetic innervation in the subject.

In some embodiments, the step of determining comprises determining level, density, localization, or function of NETs in the portion of the subject.

In some embodiments, image data from dynamic images are used to distinguish changes in local or global blood flow from changes in local or global NET function or distribution.

In some embodiments, the method further comprises providing image data using another imaging agent, and determining blood flow based on the image data to distinguish local or global blood flow from local or global changes in NET function or distribution.

In some embodiments, the method further comprising assessing cardiac sympathetic innervation in the subject.

In some embodiments, at least a portion of the compound is present as a pharmaceutically acceptable salt. In some embodiments, the salt is a formate salt or the ascorbate salt of the compound. In some embodiments, the salt is the citrate salt or the trifluoroacetate salt of the compound.

Figure 1:
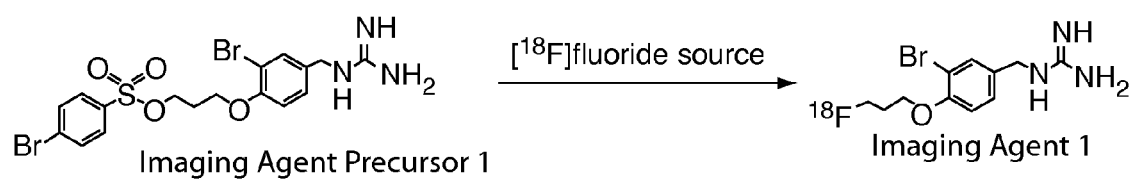
FIG. 1 shows an example of a nucleophilic $[^{18}F]$-fluorination reaction using an imaging agent precursor and a fluoride source to form an imaging agent of the invention.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION OF THE INVENTION

The present invention generally relates to compounds, compositions thereof, systems comprising such compounds, reagents, cassettes, methods, kits, and apparatuses for the synthesis and/or use of imaging agents and precursors thereof. In some aspects, the invention generally relates to an imaging agent of the invention (i.e., an imaging agent of Formula (I), including an imaging agent of formula (V), such as imaging agent-1) synthesized using methods described herein. The imaging agents of the invention may be used to image an area of interest in a subject, including, but not limited to, the heart, a portion of the heart, the cardiovascular system, cardiac vessels, brain, and other organs.

In some embodiments, the present invention provides methods for synthesizing an imaging agent precursor of the invention that can be reacted with an imaging moiety (or a source thereof) to form an imaging agent. It is advantageous to utilize methods which involve high-yielding reactions and a relatively low number of synthetic, purification, and/or formulation events in the preparation of an imaging agent precursor and/or imaging agent. Accordingly, many of the methods provided herein for synthesizing an imaging agent precursor and/or imaging agent produce the compounds in fewer steps than previously reported, with greater ease of synthesis, and/or with higher yield. In certain embodiments, the fluorination of an imaging agent precursor comprising a sulfonate leaving group is performed with a fully deprotected form of the precursor eliminating the need for a subsequent deprotection step. Therefore, the last synthetic step is the fluorination reaction eliminating the loss of isotopically labeled material in subsequent steps.

The methods and compositions of this disclosure provide various advantages over the methods, compounds, and compositions known in the art. As another example, some of the compounds provided herein are salts associated with a counter anion, wherein the counter anion has been unexpectedly found to improve the solubility, yield, stability, and/or ease of purification of the compound. For example, the counter anion in some instances influences numerous aspects of the manufacture of an imaging agent, or precursor thereof, or a composition thereof, including (1) solubility of the imaging agent precursor and/or imaging agent, (2) purity of the imaging agent precursor and/or imaging agent, and (3) stability of the imaging precursor and/or imaging agent.

Imaging Agents

In some aspects, imaging agents for imaging an area of interest of a subject are provided. In certain embodiments, the imaging agent is labeled with $^{18}F$ and is useful in PET imaging. In some embodiments, the imaging agent is a compound comprising formula (I):

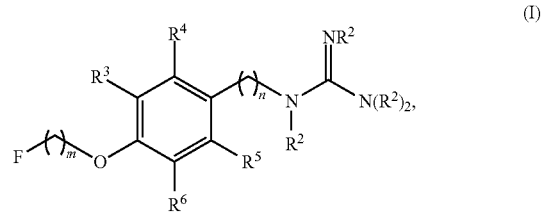

or a salt, free base, or combinations thereof, wherein:

$R^3$, $R^4$, $R^5$, and $R^6$ can be the same or different and are individually hydrogen, $C_1$-$C_6$ alkyl, heteroalkyl, halide, —$OR^7$, —$SR^7$, —$N(R^7)_2$, or —$C(=O)R^8$, each optionally substituted;

each $R^2$ can be the same or different and is hydrogen or a nitrogen-protecting group;

each $R^7$ can be the same or different and is hydrogen, alkyl, heteroalkyl, cycloalkyl, haloalkyl, heterocyclyl, aryl, or heteroaryl, each optionally substituted;

each $R^8$ can be the same or different and is hydrogen, alkyl, heteroalkyl, cycloalkyl, haloalkyl, heterocyclyl, aryl, heteroaryl, —OH, alkoxy, —$NH_2$, alkylamino, —SH, or alkylthiol, each optionally substituted;

m is an integer between 1 and 12, inclusive; and n is an integer between 1 and 4, inclusive.

In certain embodiments, the imaging agent is a compound comprising formula (V):

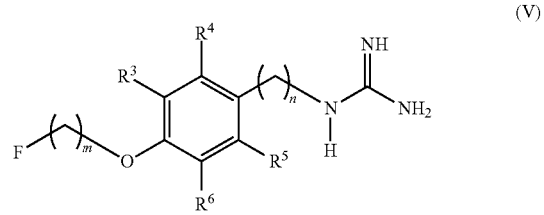

or a salt, free base, or combinations thereof, wherein $R^3$, $R^4$, $R^5$, $R^6$, m, and n are as defined above.

In certain embodiments, the compound of formula (I) comprises formula:

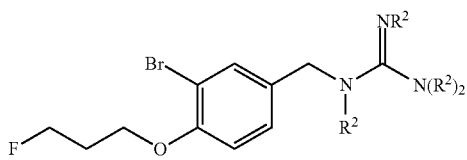

wherein at least one $R^2$ is a nitrogen protecting group. In certain embodiments, the nitrogen protecting group is a Boc protecting group. In certain embodiments, one, two, or three $R^2$ groups are nitrogen protecting groups (e.g., Boc protecting groups), and the other $R^2$ groups are hydrogen. In certain embodiments, the fluorine of the compounds is isotopically enriched with $^{18}F$. Fully protected, partially protected, and fully unprotected forms of compounds comprising formula (I) isotopically enriched with $^{18}F$ may be useful as imaging agents.

A non-limiting example of an imaging agent, referred to herein as imaging agent-1, comprises the formula:

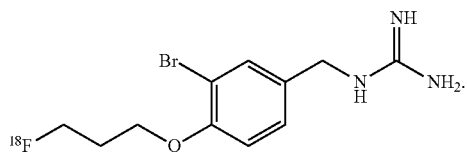 [SMILES: N=C(N)NCc1ccc(OCCC[18F])c(Br)c1]

As used herein, the term imaging agent-1 may also refer to a salt and/or a free base, or combinations thereof, of the above compound, such as a formate salt (Formula (VI)), an ascorbate salt (Formula (VII)), a citrate salt (Formula (IX)), or a trifluoroacetic acid salt (Formula (X)), as described herein.

For the sake of convenience and brevity, various aspects and embodiments of the invention are described in terms of imaging agent-1. However, it is to be understood that, unless otherwise specified, the invention contemplates the synthesis and use of imaging agents other than imaging agent-1 in these various aspects and embodiments. Such imaging agents may be compounds of formula (I) and/or compounds of formula (V), as described herein.

As used herein, the term "imaging agent" refers to any chemical compound that includes an imaging moiety. An "imaging moiety" refers to an atom or group of atoms that is capable of producing a detectable signal itself, or upon exposure to an external source of energy (e.g., electromagnetic radiation, ultrasound, and the like). Nuclear medicine imaging agents may comprise radioisotopes as the imaging moiety. For example, nuclear medicine imaging agents can include $^{11}C$, $^{13}N$, $^{18}F$, $^{76}Br$, $^{123}I$, $^{124}I$, $^{125}I$, $^{131}I$, $^{99m}Tc$, $^{95}Tc$, $^{111}In$, $^{62}Cu$, $^{64}Cu$, $^{67}Ga$, and $^{68}Ga$ as the imaging moiety. In some embodiments, the imaging moiety is $^{18}F$. Imaging agents comprising $^{18}F$ have been used for imaging hypoxia and cancer (Drugs of the Future 2002, 27, 655-667).

Imaging agents allow for the detection, imaging, and/or monitoring of the presence and/or progression of a condition, pathological disorder, and/or disease. Typically, the imaging agent may be administered to a subject in order to provide information relating to at least a portion of the subject (e.g., human). In some cases, an imaging agent may be used to highlight a specific area of a subject, rendering organs, blood vessels, tissues, and/or other portions more detectable and more clearly imaged. By increasing the detectability and/or image quality of the area being studied, the presence and extent of disease and/or injury can be determined.

In some embodiments, an imaging agent comprising an isotope such as a radioisotope may be referred to as being "isotopically enriched." An "isotopically enriched" composition refers to a composition comprising a percentage of one or more isotopes of an element that is more than the percentage (of such isotope) that occurs naturally. As an example, a composition that is isotopically enriched with a fluoride species may be "isotopically enriched" with fluorine-18 ($^{18}F$). Thus, with regard to a plurality of compounds, when a particular atomic position is designated as $^{18}F$, it is to be understood that the abundance (or frequency) of $^{18}F$ at that position (in the plurality) is greater, including substantially greater, than the natural abundance (or frequency) of $^{18}F$, which is essentially zero. In some embodiments, a fluorine designated as $^{18}F$ may have a minimum isotopic enrichment factor of about 0.001% (i.e., about 1 out of $10^5$ fluorine species is $^{18}F$), 0.002%, 0.003%, 0.004%, 0.005%, 0.006%, 0.007%, 0.008%, 0.009%, 0.01%, about 0.05%, about 0.1%, about 0.2%, about 0.3%, about 0.4%, about 0.5%, about 0.75%, about 1%, about 2%, about 3%, about 4%, about 5%, about 10%, about 15%, about 20%, about 30%, about 40%, about 50%, about 60%, about 70%, about 80%, about 90%, about 95%, or greater. The minimum isotopic enrichment factor, in some instances, may range from about 0.001% to about 1%. The isotopic enrichment of the compounds provided herein can be determined using conventional analytical methods known to one of ordinary skill in the art, including mass spectrometry and HPLC.

In some embodiments, methods and systems of this disclosure use or comprise compounds of formula (I) or (V), including, without limitation, imaging agent-1. In some embodiments, the present invention relates to methods of imaging, including methods of imaging in a subject that includes administering a composition or formulation that includes an imaging agent (e.g., an imaging agent comprising formula (I) or formula (V), such as imaging agent-1) to the subject by injection, infusion, or any other known method, and imaging a region of interest of the subject. Regions of interest may include, but are not limited to, the heart, a portion of the heart, cardiovascular system, cardiac vessels, pancreas, adrenal glands, salivary glands, thymus, or other organs with high sympathetic innervation or high imaging agent uptake. Regions of interest may also include tumors. In certain embodiments, the imaging agent is used as a radiotracer for mapping the cardiac nerve terminal in vivo using positron emission tomography (PET) or other imaging techniques. An event of interest can be imaged and detected and/or other information may be determined using methods and/or systems of the disclosure.

The imaging agents of the invention, including imaging agent-1, may act as norepinephrine transporter ligands that target or bind NET. In some embodiments, the methods comprise detecting MET, including determining NET levels, in a subject, wherein determining may comprise determining the level, density, function, and/or localization of NET in a subject. In certain embodiments, without wishing to be bound by a particular theory, the imaging agent binds to norepinephrine transporters (NET) allowing for imaging of cardiac sympathetic innervation or activity. Accordingly, in some aspects, methods for assessing cardiac sympathetic innervation and/or myocardial sympathetic function are provided.

Imaging Agent Precursors

Figure 6:
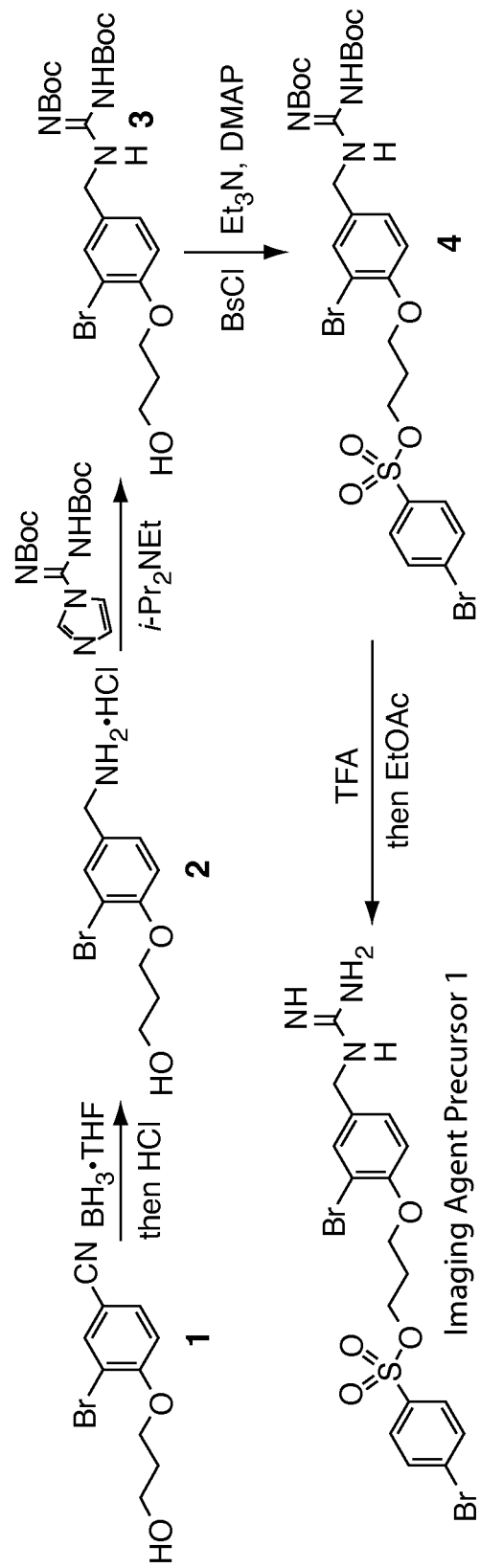
FIG. 6 shows an exemplary synthesis of an imaging agent precursor of the invention.

In other aspects, imaging agent precursors useful in the preparation of imaging agents of the invention are provided. An exemplary synthesis of imaging agent precursor 1 is shown in FIG. 6. In certain embodiments, an imaging agent precursor of the invention comprises a leaving group (e.g., a sulfonate) that can be substituted with a nucleophile in a substitution reaction. The imaging agent precursor may also include various functional groups that are optionally protected. Earlier precursors in the synthesis of imaging agents of the invention are also encompassed by the present invention.

In certain embodiments, the present invention provides a compound (e.g., an imaging agent precursor) comprising formula (II):

(II)

or a salt, free base, or combinations thereof, wherein $R^1$ is alkyl, heteroalkyl, cycloalkyl, heterocyclyl, aryl, heteroaryl, arylalkyl, heteroarylalkyl, alkenyl, alkynyl, or haloalkyl, each optionally substituted;

$R^3$, $R^4$, $R^5$, and $R^6$ can be the same or different and are individually hydrogen, $C_1$-$C_6$ alkyl, heteroalkyl, halide, —$OR^7$, —$SR^7$, —$N(R^7)_2$, or —$C(=O)R^8$, each optionally substituted;

each $R^2$ can be the same or different and is hydrogen or a nitrogen-protecting group;

each $R^7$ can be the same or different and is hydrogen, alkyl, heteroalkyl, cycloalkyl, heterocyclyl, haloalkyl, aryl, or heteroaryl, each optionally substituted;

each $R^8$ can be the same or different and is hydrogen, alkyl, heteroalkyl, cycloalkyl, heterocyclyl, haloalkyl, aryl, heteroaryl, —OH, alkoxy, —$NH_2$, alkylamino, —SH, or alkylthiol, each optionally substituted;

m is an integer between 1 and 12, inclusive; and n is and integer between 1 and 4, inclusive. In some embodiments, a compound of formula (II) is an imaging agent precursor.

In certain embodiments, the imaging agent precursor is a compound comprising Formula (IV):

(IV)

or a salt, free base, or combination thereof, wherein $R^1$, $R^3$-$R^6$, m, and n are as defined herein.

A non-limiting example of an imaging agent precursor, referred to herein as imaging agent precursor-1, comprises the formula:

or a salt, free base, or combinations thereof.

Another non-limiting example of an imaging agent precursor, referred to herein as imaging agent precursor-2, comprises the formula:

or a salt, free base, or combinations thereof.

Another non-limiting example of an imaging agent precursor comprises the formula:

or a salt, free base, or combinations thereof.

Another non-limiting example of an imaging agent precursor comprises the formula:

or a salt, free base, or combinations thereof.

Another non-limiting example of an imaging agent precursor comprises the formula:

or a salt, free base, or combinations thereof.

Another non-limiting example of an imaging agent precursor comprises the formula:

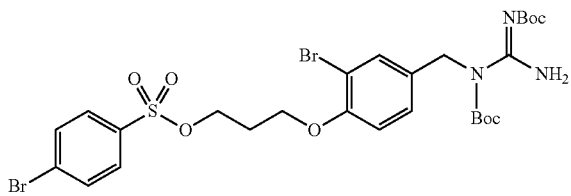

or a salt, free base, or combinations thereof.

Another non-limiting example of an imaging agent precursor comprises the formula:

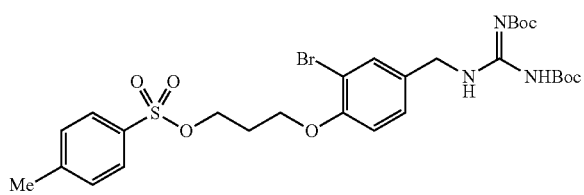

or a salt, free base, or combinations thereof.

Another non-limiting example of an imaging agent precursor comprises the formula:

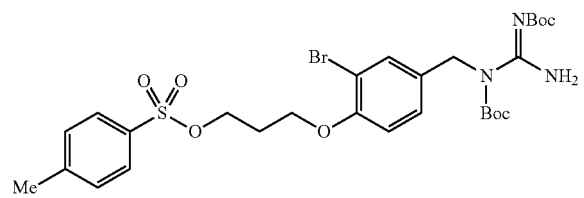

or a salt, free base, or combinations thereof.

For the sake of convenience and brevity, various aspects and embodiments of the invention are described in terms of imaging agent precursor-1 and/or imaging agent precursor-2. However, it is to be understood that, unless otherwise specified, the invention contemplates the synthesis and use of imaging agent precursors other than imaging agent precursor-1 and -2 in these various aspects and embodiments. Such imaging agent precursors may be compounds of Formula (II) and/or compounds of Formula (IV) and/or compounds of Formula (III), as described herein.

In certain embodiments, a salt of a compound of formula (II) is provided. That is, a compound of formula (II) may be charged and may be associated with a counter ion. In some cases, the compound of formula (II) is positively charged. In a particular embodiment, the guanidine functional group of the compound of formula (II) is protonated and therefore positively charged such that a salt of a compound of formula (II) comprises formula (III):

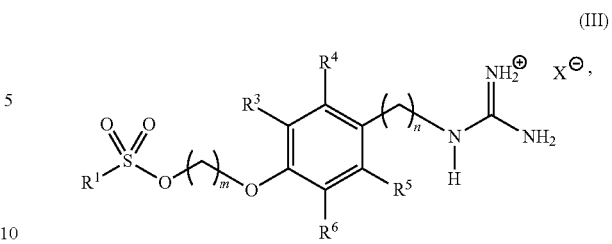

wherein $X^\ominus$ is a counter anion. As will be understood by those of ordinary skill in the art, in embodiments described herein wherein a compound comprises a compound of formula (II), or a variation thereof, the compound may be present, at least in part, in a salt form. For example, any compound described herein comprising a neutral and/or unprotonated guanidine functional group may also be present as a protonated guanidine functional group (e.g., associated with a counter anion).

Those of ordinary skill in the art will be aware of suitable counter anions. In addition, those of ordinary skill in the art will be aware that the counter anion $X^\ominus$ may have a charge of greater than (−1) (e.g., (−2), (−3)), and in such embodiments, each counter anion $X^\ominus$ may be associated with more than one molecule of a compound of the present invention. Non-limiting examples of suitable counter anions include the conjugate base of inorganic acids (e.g., chloride, bromide, iodide, fluoride, nitrate, sulfate, phosphate) or from the conjugate base of organic acids (e.g., carboxylate, acetate, benzoate, tartrate, adipate, lactate, formate, maleate, glutamate, ascorbate, citrate, gluconate, oxalate, succinate, pamoate, salicylate, isethionate, succinamate, mono-diglycollate, di-isobutyrate, glucoheptonate). Still other non-limiting examples of salts include adipate, alginate, aminosalicylate, anhydromethylenecitrate, arecoline, aspartate, bisulfate, camphorate, digluconate, dihydrobromide, disuccinate, glycerophosphate, hemisulfate, fluoride, iodide, methylenebis(salicylate), napadisylate, oxalate, pectinate, persulfate, phenylethylbarbiturate, picrate, propionate, thiocyanate, tosylate, undecanoate, acetate, benzenesulfonate, benzoate, bicarbonate, bitartrate, bromide, calcium edentate, camyslate, carbonate, chloride, citrate, dihydrochloride, edentate, edisylate, estolate, esylate, fumarate, gluceptate, gluconate, glutamate, glycollylarsanilate, hexylresorcinate, hydrabamine, bromide, chloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, teoclate, and triethiodide (see Berge et al., *Journal of Pharmaceutical Sciences*, 66(1), 1977, 1-19). In certain embodiments, the salt is a mesylate (i.e., methanesulfonate), phosphate, sulfate, acetate, formate, benzoate, trifluoroacetate, or tosylate salt of a compound of formula (II). In certain embodiments, the salt is a mesylate (i.e., methanesulfonate), acetate, formate, benzoate, trifluoroacetate, or tosylate salt of a compound of formula (II).

In some embodiments, $R^1$ is alkyl, haloalkyl, or aryl. In some cases, $R^1$ is alkyl (e.g., methyl, ethyl, n-propyl, i-propyl, n-butyl, i-butyl, t-butyl, pentyl, hexyl). In some cases, $R^1$ is haloalkyl (e.g., —$CF_3$, —$CHF_2$, —$CH_2F$, —$CF_2CF_3$, —$CH_2CF_3$). In some cases, $R^1$ is aryl, optionally substituted. In certain embodiments, $R^1$ is substituted or unsubstituted phenyl. In certain embodiments, $R^1$ is unsubstituted phenyl.

In some cases, $R^1$ is substituted phenyl (e.g., 4-CH$_3$Ph, 2,4, 6-(CH$_3$)$_3$C$_6$H$_2$, C$_6$H$_4$X wherein X is halide (e.g., 4-BrC$_6$H$_4$)).

In some embodiments n is an integer between 1 and 4, inclusive, or is 1, 2, 3, or 4.

In some embodiments, m is an integer between 1 and 12, inclusive; or 1 and 10, inclusive; or 1 and 8, inclusive; or 1 and 6, inclusive; or is 1, 2, 3, 4, 5, or 6. In some embodiments, m is an integer between 3 and 12, inclusive.

As described above, $R^2$ may be a nitrogen protecting group. Nitrogen-protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. For example, nitrogen protecting groups include, but are not limited to, carbamates (including methyl, ethyl and substituted ethyl carbamates (e.g. Troc), to name a few), amides, cyclic imide derivatives, N-alkyl and N-aryl amines, imine derivatives, and enamine derivatives, to name a few. In some embodiments, the nitrogen-protecting group is carbobenzyloxy (Cbz), p-methoxybenzyl carbonyl (MeOZ), t-butyloxycarbonyl (Boc), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), or p-toluenesulfonyloxy (Ts). In certain embodiments, at least one $R^2$ is t-butyloxycarbonyl (Boc).

Nitrogen-protecting groups such as amide groups include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen-protecting groups such as carbamate groups include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10, 10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen-protecting groups such as sulfonamide groups include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide Other nitrogen-protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyemesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentaacylchromium- or tungsten)acyl] amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In some embodiments, $R^4$, $R^5$, and $R^6$ are hydrogen; and $R^3$ is $C_1$-$C_6$ alkyl, hetero-$C_1$-$C_6$ alkyl, halide, —$OR^7$, —$SR^7$, —$N(R^7)_2$, or —$C(=O)R^8$, each optionally substituted. In some cases, $R^3$ is halo (e.g., F, Cl, Br, I). In certain embodiments, $R^3$ is bromo. In a particular embodiment, $R^4$, $R^5$, and $R^6$ are hydrogen; and $R^3$ is bromo, for example, such that the compound of formula (II) comprises the structure:

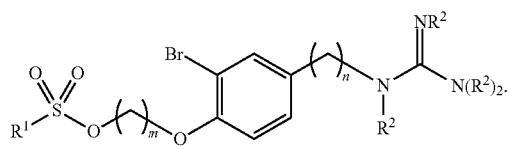

In some embodiments, each $R^2$ is hydrogen such that the compound of formula (II) comprises the structure:

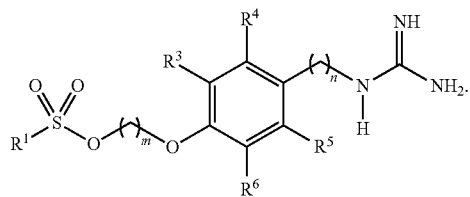

In a particular embodiment, $R^4$, $R^5$, and $R^6$ are hydrogen; $R^3$ is bromo; and each $R^2$ is hydrogen, for example, such that the compound of formula (II) has the structure:

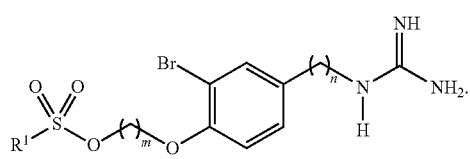

In other embodiments, at least one $R^2$ is not hydrogen. For example, the compound of formula (II) may be one of the formulae:

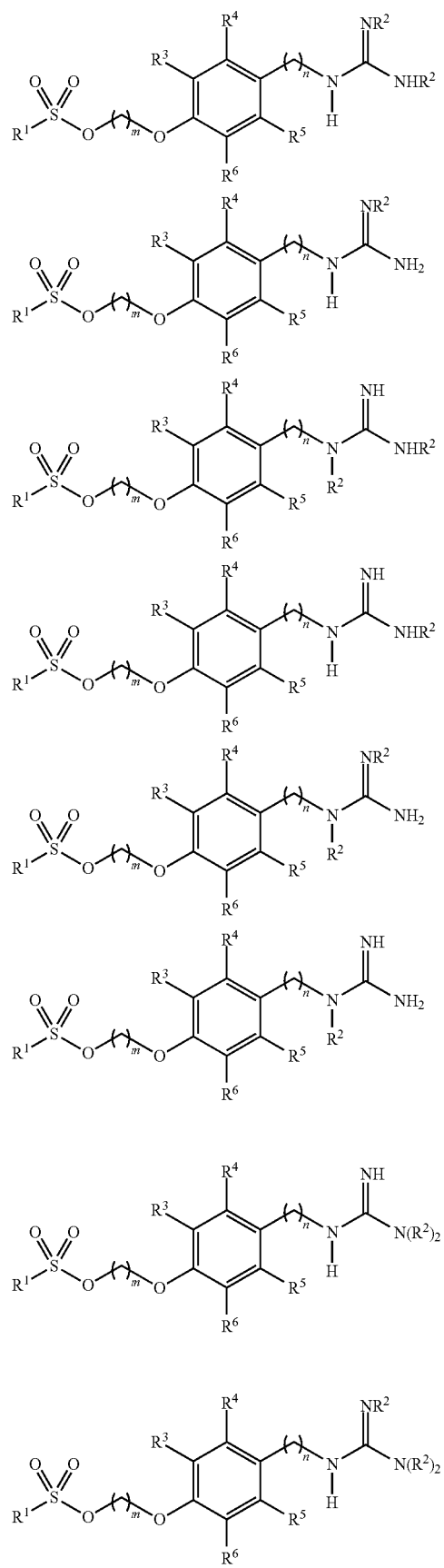

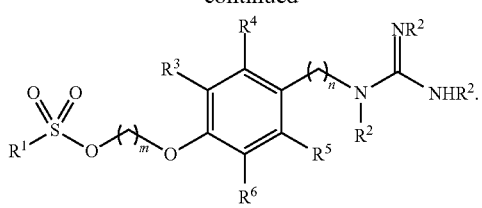

As described herein, these compounds may be present, as a salt, free base, or combination thereof.

In some embodiments, m is 3, n is 1, $R^3$ is Br (or another halogen), and $R^4$, $R^5$, and $R^6$ are all H, such that a compound of formula (II) comprises the structure:

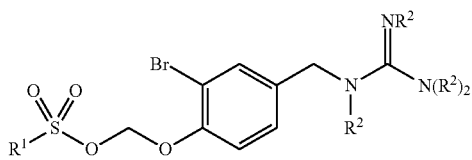

wherein each of $R^1$ and $R^2$ are as defined above and described in embodiments herein, both singly and in combination. Further, in some cases, each $R^2$ is H, such that the compound of formula (II) comprises the structure:

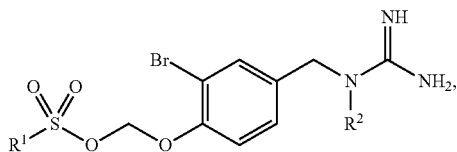

wherein $R^1$ is as defined above and described in embodiments herein.

In certain embodiments, a compound of formula (II) comprises the structure:

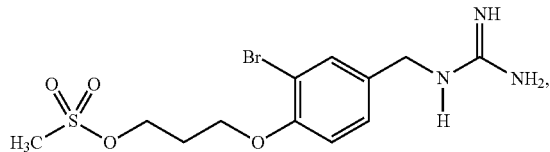

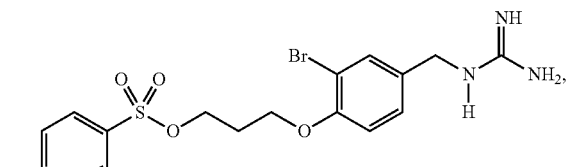

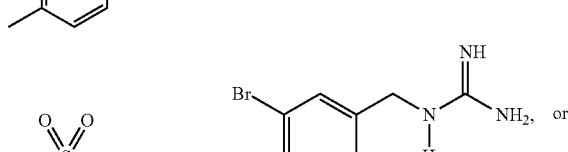

or a salt, free base, or combination thereof.

In certain embodiments, the present invention provides compounds useful in the synthesis of compounds of Formula (II). In certain embodiments, the present invention provides a compound of formula:

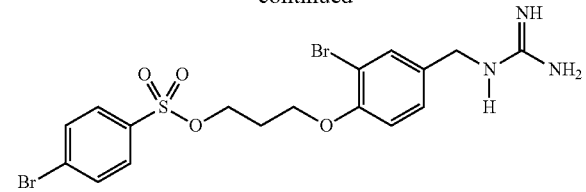

or a salt, free base, or combination thereof; wherein each $R^2$ can be the same or different and is hydrogen or a nitrogen-protecting group; and m is an integer between 3 and 12, inclusive. In one embodiment, m is 3.

In certain embodiments, the invention provides a compound comprising formula:

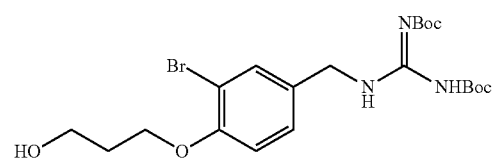

or a salt, free base, or combination thereof.

In certain embodiments, the invention provides a compound comprising formula:

or a salt, free base, or combination thereof.

In one embodiment, the invention provides a compound comprising formula:

or a salt, free base, or combination thereof.

In one embodiment, the invention provides a compound comprising formula:

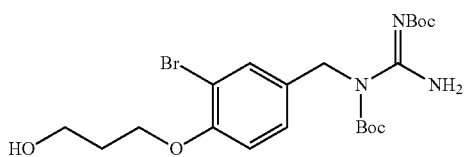

or a salt, free base, or combinations thereof.

In certain embodiments, m is an integer between 3 and 10, inclusive; between 3 and 6, inclusive; or between 3 and 5, inclusive. In certain embodiments, m is 3, 4, 5, or 6. In certain embodiments, m is 3.

In some embodiments, all $R^2$ are hydrogen. In other embodiments, at least one $R^2$ is a nitrogen protecting group (e.g., nitrogen protecting groups described herein). In other embodiments, at least two $R^2$ are nitrogen protecting group s (e.g., nitrogen protecting groups described herein). In other embodiments, at least three $R^2$ are nitrogen protecting groups (e.g., nitrogen protecting groups described herein). In some embodiments, the nitrogen-protecting group is carbobenzyloxy (Cbz), p-methoxybenzyl carbonyl (MeOZ), t-butyloxycarbonyl (Boc), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), or p-toluenesulfonyloxy (Ts). In certain embodiments, at least one $R^2$ is t-butyloxycarbonyl (Boc). In certain embodiments, at least two $R^2$ are t-butyloxycarbonyl (Boc).

In another aspect, the invention provides a compound comprising formula:

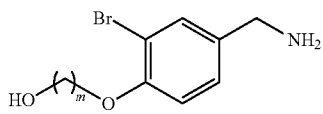

or a salt, free base, or combination thereof, wherein m is an integer between 3 and 12, inclusive. In certain embodiments, m is an integer between 3 and 10, inclusive; between 3 and 6, inclusive; or between 3 and 5, inclusive. In certain embodiments, m is 3, 4, 5, or 6. In certain embodiments, m is 3.

In one embodiment, the invention provides a compound comprising formula:

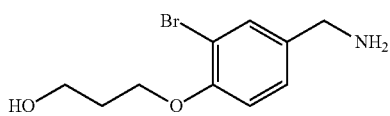 [SMILES: NCc1ccc(OCCCO)c(Br)c1]

or a free base, salt, or combination thereof.

In one aspect, the invention provides a compound comprising formula:

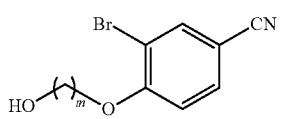

or a salt thereof, wherein m is an integer between 3 and 12, inclusive. In certain embodiments, m is an integer between 3 and 10, inclusive; between 3 and 6, inclusive; or between 3 and 5, inclusive. In certain embodiments, m is 3, 4, 5, or 6. In certain embodiments, m is 3.

In one embodiment, the invention provides a compound comprising formula:

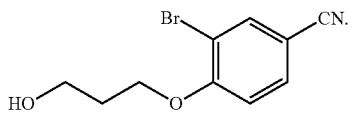 [SMILES: N#Cc1ccc(OCCCO)c(Br)c1]

Methods of Synthesizing Imaging Agent Precursors

In other aspects, methods of synthesizing imaging agent precursors of the invention and imaging agents of the invention are provided. In certain embodiments, an imaging agent precursor with a leaving group (e.g., sulfonate) is reacted with a nucleophile in a substitution reaction to yield an imaging agent of the invention, or a protected form thereof. Synthetic methods are also provided for preparing earlier precusuors in the synthesis of imaging agents of the invention, for example, synthetic methods exemplary steps of which are shown in FIG. 6.

In some embodiments, the present invention provides methods for synthesizing imaging agent precursors of the invention. The methods described herein may be used for the synthesis of a variety of imaging agent precursors. Generally, the imaging agent precursor includes a leaving group that is replaced by an imaging moiety, such as an $^{18}F$ species.

The imaging agent precursors of the invention (e.g., compounds of Formula (II)) may be prepared in a variety of different ways. In certain embodiments, the free hydroxyl group of an alcohol that comprises formula (XI):

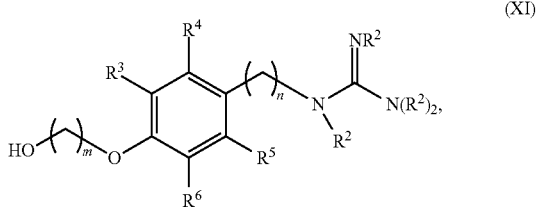

(XI)

or a salt, free base, or combinations thereof, wherein $R^3$, $R^4$, $R^5$, and $R^6$ can be the same or different and are individually hydrogen, $C_1$-$C_6$ alkyl, heteroalkyl, halide, —$OR^7$, —$SR^7$, —$N(R^7)_2$, or —$C(=O)R^8$, each optionally substituted;

each $R^2$ can be the same or different and is hydrogen or a nitrogen-protecting group;

each $R^7$ can be the same or different and is hydrogen, alkyl, heteroalkyl, cycloalkyl, heterocyclyl, haloalkyl, aryl, or heteroaryl, each optionally substituted;

each $R^8$ can be the same or different and is hydrogen, alkyl, heteroalkyl, cycloalkyl, heterocyclyl, haloalkyl, aryl, heteroaryl, —OH, alkoxy, —$NH_2$, alkylamino, —SH, or alkylthiol, each optionally substituted;

m is an integer between 1 and 12, inclusive; and n is an integer between 1 and 4, inclusive, is converted into a suitable leaving group (e.g., a sulfonate leaving group) to yield a compound comprising Formula (II). Each of $R^2$-$R^8$, m, and n are as defined above and described in embodiments herein, both singly and in combination, unless stated otherwise. Sulfonate leaving group methodology is reviewed in Netscher, *Recent Res. Dev. Org. Chem.* 7:71-83, 2003, which is incorporated herein by reference. In certain embodiments, the free hydroxyl group is converted into a tosylate (4-methylbenzenesulfonate) using tosyl halide (e.g., tosyl chloride). In certain embodiments, the free hydroxyl group is converted into a besylate (benzenesulfonate) using a besylate halide (e.g., besylate chloride). In certain embodiments, the free hydroxyl group is converted into a nosylate (4-nitrobenzenesulfonate) using a nosylate halide (e.g., nosylate chloride). In other embodiments, the free hydroxyl group is converted into bromobenzenesulfonate using a bromobenzenesulfonate halide (e.g., bromobenzenesulfonate chloride). In other embodiments, the free hydroxyl group is converted into a mesylate (methanesulfonate) using a mesyl halide (e.g., mesyl chloride). In other embodiments, the free hydroxyl group is converted into a triflate (trifluoromethanesulfonate) using triflic anhydride or a triflic halide. As would be appreciate by one of skill in the art, other sulfonates may be used in the imaging agent precursors of the invention. Typically the preparation of the sulfonate comprising Formula (II) is performed in an aprotic solvent (e.g., dichloromethane, THF) at or around room temperature in the presence of a base such a DMAP and/or a trialkylamine.

The alcohol comprising formula (XI):

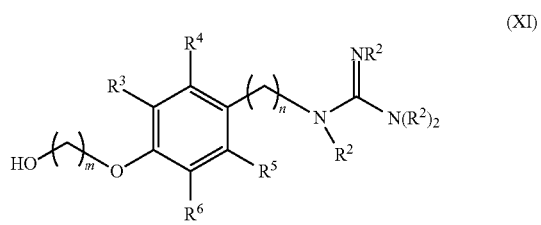
(XI)

may be prepared based on synthetic methodologies disclosed in PCT Publication No. WO 2008/083056, which is incorporated herein by referenced. Furthermore, exemplary syntheses of various imaging agent precursors of Formula (II), including salt forms thereof, are provided in Examples 1-13 and FIG. 6.

In certain embodiments, the alcohol comprising formula (XI) is prepared by reacting a compound comprising formula:

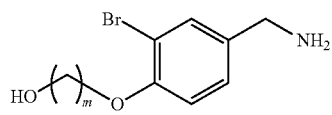

or a salt, free base, or combination thereof, with a compound of formula:

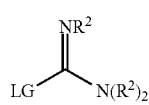

wherein LG is a suitable leaving group. In one embodiment, m is 3.

In certain embodiments, the compound comprising formula:

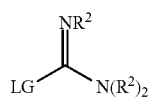

is of formula:

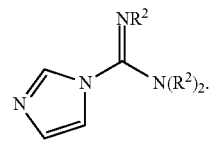

In one embodiment, the compound comprising formula:

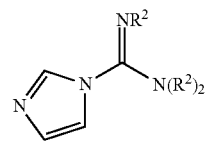

is of formula:

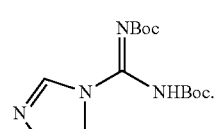

In one embodiment, the compound comprising formula:

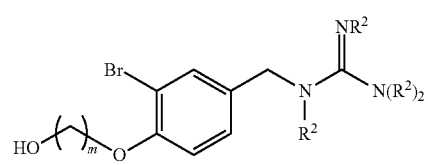

is of formula:

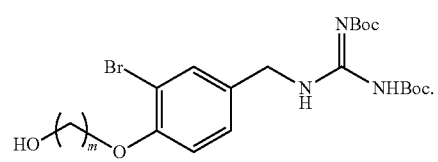

In another aspect, the invention provides a method of preparing the starting material for the previous reaction by reducing a compound comprising formula:

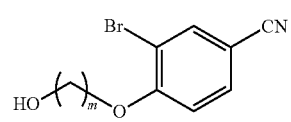

or a salt thereof, wherein m is an integer between 3 and 12, inclusive, with a reductant under suitable conditions to form a compound comprising:

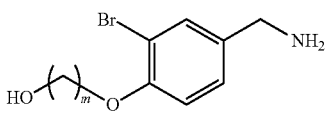

or a salt, free base, or combination thereof. In one embodiment, m is 3. Exemplary agents useful in reducing a nitrile group (—CN) to a primary amino group (—CH$_2$NH$_2$), include, but are not limited to, LiAlH$_4$ (LAH); hydrogen gas (H$_2$) in the presence of a metal catalyst (e.g., Pd, Pt, Ni); NaBH$_4$ and a transition metal salt to form the metal borate in situ (e.g., NiCl$_2$ to form nickel borate (NiBH$_4$) in situ; ZnCl$_2$ to form the zinc borate (ZnBH$_4$) in situ); NaBH$_4$ plus I$_2$; NaBH$_4$ plus H$_2$SO$_4$; NiBH$_4$; ZnBH$_4$; LiBH$_4$; and borane (e.g., BH$_3$/THF, BH$_3$/DCM). In one embodiment, the reductant is borane (e.g., BH$_3$/THF).

In some embodiments, the invention provides a method of deprotecting a guanidine functional group of a compound comprising formula (II):

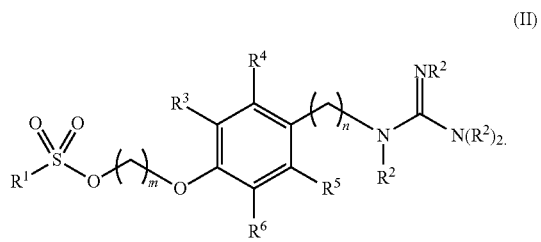

For example, in some embodiments, a method comprises deprotecting a guanidine functional group of a compound comprising formula (II):

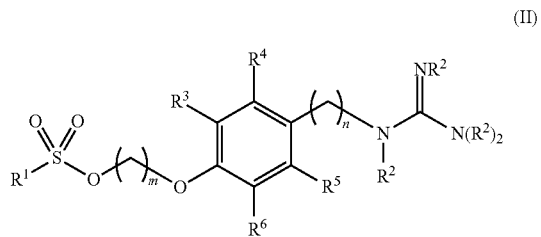

or a salt, free base, or combination thereof, under conditions suitable to form a compound comprising formula (IV):

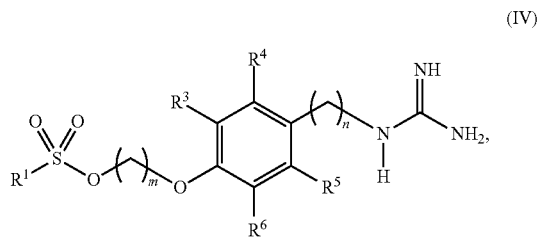

or a salt, free base, or combination thereof, wherein

R$^1$ is alkyl, heteroalkyl, cycloalkyl, aryl, heteroaryl, arylalkyl, heteroarylalkyl, alkenyl, alkynyl, heterocyclyl, or haloalkyl, each optionally substituted;

R$^3$, R$^4$, R$^5$, and R$^6$ can be the same or different and are individually hydrogen, C$_1$-C$_6$ alkyl, heteroalkyl, halide, —OR$^7$, —SR$^7$, —N(R$^7$)$_2$, or —C(=O)R$^8$, each optionally substituted;

each R$^2$ can be the same or different and is hydrogen or a nitrogen-protecting group;

each R$^7$ can be the same or different and is hydrogen, alkyl, heteroalkyl, cycloalkyl, haloalkyl, aryl, heteroaryl, or heterocyclyl, each optionally substituted;

each R$^8$ can be the same or different and is hydrogen, alkyl, heteroalkyl, cycloalkyl, haloalkyl, heterocyclyl, aryl, heteroaryl, —OH, alkoxy, —NH$_2$, alkylamino, —SH, or alkylthiol, each optionally substituted;

m is an integer between 1 and 12, inclusive; and n is an integer between 1 and 4, inclusive.

Each of R$^1$-R$^8$, m, and n are as defined above and described in embodiments herein, both singly and in combination, unless stated otherwise.

Suitable conditions for deprotection of a guanidine functional group are described herein. Such conditions may include an acidic environment (e.g., pH equal or less than 4, equal to or less than 3, equal to or less than 2, or equal to or less than 1). For example, in certain embodiments, one or more of R$^2$ is t-butyloxycarbonyl, and the step of deprotecting comprising treating a compound of formula (II) with trifluoroacetic acid, hydrochloric acid, sulfuric acid, or p-toluenesulfonic acid. Such conditions for deprotection may additionally or alternatively include a temperature ranging from 100-150° C.

The methods described herein may be carried out in any suitable solvent, including, but are not limited to, non-halogenated hydrocarbon solvents (e.g., pentane, hexane, heptane, cyclohexane), halogenated hydrocarbon solvents (e.g., dichloromethane, chloroform, fluorobenzene, trifluoromethylbenzene), aromatic hydrocarbon solvents (e.g., toluene, benzene, xylene), ester solvents (e.g., ethyl acetate), ether solvents (e.g., tetrahydrofuran, dioxane, diethyl ether, dimethoxyethane.), and alcohol solvents (e.g., ethanol, methanol, propanol, isopropanol, tert-butanol). In certain embodiments, a protic solvent is used. In other embodiments, an aprotic solvent is used. Non-limiting examples of solvents useful include acetone, acetic acid, formic acid, dimethyl sulfoxide, dimethyl formamide, acetonitrile, p-cresol, glycol, petroleum ether, carbon tetrachloride, hexamethyl-phosphoric triamide, triethylamine, picoline, and pyridine.

The methods may be carried out at any suitable temperature. In some cases, the method is carried out at about room temperature (e.g., about 20° C., between about 20° C. and about 25° C., about 25° C., or the like). In some cases, however, the method is carried out at a temperature below or above room temperature, for example, at about −78° C. at about −70° C., about −50° C., about −30° C., about −10° C., about −0° C., about 10° C., about 30° C., about 40° C., about 50° C., about 60° C., about 70° C., about 80° C., about 90° C., about 100° C., about 120° C., about 140° C., or the like. In some embodiments, the method is carried out at temperatures above room temperature, for example, between about 25° C. and about 120° C., or between about 25° C. and about 100° C., or between about 40° C. and about 120° C., or between about 80° C. and about 120° C. The temperature may be maintained by reflux of the solution. In some cases, the method is carried out at temperatures between about −78° C. and about 25° C., or between about 0° C. and about 25° C.

The methods described herein may be carried out at any suitable pH, for example, equal to or less than about 13, equal to or less than about 12, equal to or less than about 11, equal to or less than about 10, equal to or less than about 9, equal to or less than about 8, equal to or less than about 7, or equal to or less than about 6. In some cases, the pH may be greater than or equal to 1, greater than or equal to 2, greater than or equal to 3, greater than or equal to 4, greater than or equal to 5, greater than or equal to 6, greater than or equal to 7, or greater than or equal to 8. In some cases, the pH may be between about 2 and about 12, or between about 3 and about 11, or between about 4 and about 10, or between about 5 and about 9, or between about 6 and about 8, or about 7.

The percent yield of a product may be greater than about 60%, greater than about 70%, greater than about 75%, greater than about 80%, greater than about 85%, greater than about 90%, greater than about 92%, greater than about 95%, greater than about 96%, greater than about 97%, greater than about 98%, greater than about 99%, or greater.

Methods of Synthesizing Imaging Agents

In other aspects, methods are provided for synthesizing imaging agents. The methods described herein may be used for the synthesis of a variety of imaging agents of the invention from an imaging agent precursor of the invention.

Fluorination

In some cases, the imaging agent is formed by reacting an imaging agent precursor (e.g., a compound comprising formula (II)-(IV)) with an imaging moiety. The imaging agent precursor may include at least one leaving group that is susceptible to being displaced by a nucleophilic imaging moiety, such as an $^{18}F$ fluoride species. Thus, in certain embodiments, the method involves reacting an imaging agent precursor comprising a leaving group with a source of an imaging moiety (e.g., a fluoride species). For example, during the reaction, the imaging moiety replaces the leaving group via a substitution reaction, such as an $S_N2$ or $S_N1$ reaction, thereby producing the imaging agent. In certain embodiments, the fluorination reaction is a one-step procedure which does not require a subsequent deprotection step. That is, the fluorination step is performed on a fully deprotected imaging agent precursor. A non-limiting example of a synthetic method for preparing an imaging agent is shown in FIG. 1, wherein imaging agent precursor-1 is converted into imaging agent-1. In some embodiments, multiple substitution reactions may occur through multiple leaving groups during synthesis of an imaging agent from an imaging agent precursor. The methods described herein exhibit improved yields may allow for the synthesis of imaging agents, including imaging agents comprising a radioisotope (e.g., $^{18}F$). The imaging agents may be useful as sensors, diagnostic tools, and the like. Synthetic methods for preparing an imaging agent have also been designed to use an automated synthesis system to prepare and purify imaging agents that comprise a radioisotope.

As described herein, in some cases, the method of synthesizing an imaging agent of the invention may involve the use of one or more reagents (e.g., salts) that may facilitate a chemical reaction (e.g., a substitution reaction). In certain embodiments, the choice of salt form may allow for the fluorination of an unprotected imaging agent precursor. Without wishing to be bound by a particular theory, the counter anion may interact with the guanidine functional group preventing it from interfering with the fluorination reaction and/or may prevent side reactions. In certain embodiments, the salt is a mesylate (i.e., methanesulfonate), phosphate, sulfate, acetate, formate, benzoate, trifluoroacetate, or tosylate salt of a compound of formula (II). In certain embodiments, the salt is a mesylate (i.e., methanesulfonate), acetate, formate, benzoate, trifluoroacetate, or tosylate salt of a compound of formula (II).

In some embodiments, a method for synthesizing an imaging agent comprises contacting an imaging agent precursor of the invention (e.g., a compound comprising formula (II), (III), or (IV)) with a fluoride species resulting in the fluoride species replacing the leaving group of the precursor to produce an imaging agent (e.g., a compound comprising formula (I)) comprising the fluorine species).

In certain embodiments, the method involves a nucleophilic fluorination reaction. That is, an imaging agent precursor comprising a leaving group is reacted in the presence of a fluoride species, whereby $S_N2$ or $S_N1$ displacement of the leaving group by the fluoride species produces the imaging agent. In some embodiments, the fluoride species is isotopically enriched with $^{18}F$.

Those of ordinary skill in the art will be aware of suitable conditions for fluorinating a compound (e.g., a compound of formula (II), (III), or (IV)). For example, see International Patent Application No. PCT/US2011/024109, by Cesati, filed Feb. 8, 2011, herein incorporated by reference. In some cases, a compound of formula (II), (III), or (IV), or a salt, free base, or combination thereof, is exposed to a source of fluorine, optionally enriched with an isotope of fluorine (e.g., enriched with $^{18}F$). In some cases, the source of fluorine is a fluoride salt (e.g., KF, NaF, tetralkylammonium fluoride).

The fluorine source may comprise or be associated with or may be used in connection with another reagent. The reagent may be capable of enhancing the reactivity of the fluorine species or otherwise facilitating conversion of the precursor to the imaging agent. For example, in one set of embodiments, the reagent may be used in combination with a multidentate ligand, such as a crown ether or a cryptand that is capable of chelating a metal ion. The multidentate ligand may be, for example, 4,7,13,16,21,24-hexaoxa-1,10-diazabicyclo [8.8.8]-hexacosane (i.e., Kryptofix® 222). When the fluorine source is KF, cryptands having a high affinity for potassium are useful as they chelate potassium and thereby increase the reactivity of the fluoride ion. In some embodiments, cryptands having an affinity for potassium near that of Kryptofix® 222 (e.g., 75%, 80%, 85%, 90%, 95%, or more of the Kryptofix® 222's affinity for potassium) are used. The reaction conditions may comprise one or more solvents.

In some embodiments, the fluorination occurs in the presence of $K_2CO_3$ and Kryptofix® 222 (or any another cryptand having affinity for the cation of interest, including for example potassium, near that of Kryptofix® 222) in MeCN (acetonitrile) alone or in combination with t-BuOH, as the solvent. The molar ratio of $K_2CO_3$ to imaging agent precursor (such as but not limited to imaging agent precursor-1 or -2) ranges from about 0.5:1 to about 5:1, more preferably 0.5:1 to 1:1. In some embodiments, the molar ratio is about 0.66:1.

In some embodiments, the fluorination occurs in the presence of tetraalkylammonium carbonate or tetraalkylammonium bicarbonate in MeCN as the solvent. In some embodiments, the molar ratio of tetraalkylammonium carbonate or bicarbonate to imaging agent precursor (such as imaging agent precursor-1 or -2) is 5:1. In some embodiments, the molar ratio may range from about 7:1 to about 3:1, or from about 6:1 to about 4:1, or about 5.5:1 to about 4.5:1. The tetraalkylammonium cation may be tetraethylammonium or tetrabutylammonium but it is not so limited.

Compounds comprising formula (V):

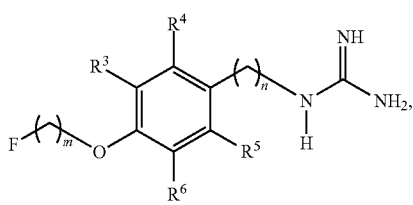

or a salt, free base, or combination thereof, wherein each of $R^3$-$R^6$, m, and n are as defined above and described in embodiments herein, both singly and in combination, can be produced from a precursor using a two-step or three-step process such as that described in International PCT Publication WO 2008/083056 by Purohit et al., which is incorporated herein by reference.

In contrast, the synthetic methods provided herein may involve a single-step preparation of imaging agents of the invention (e.g., compounds of formula (V), or a salt, free base, or combination thereof). The single-step method minimally involves fluorination of a completely or partially deprotected precursor in the presence of, for example, $K_2CO_3$/Kryptofix® 222 (or other suitable alternatives to Kryptofix® 222) or tetraalkylammonium carbonate or bicarbonate, in MeCN alone or in an MeCN mixture (such as an MeCN and t-BuOH mixture). These methods are particularly suitable when particular salt forms of the imaging agent precursors of the invention are used. Such salts include halide, acetate, formate, citric, ascorbate, trifluoroacetate, toluenesulfonate, benzoate, acetate, phosphate, sulfate, tosylate, and mesylate.

In some cases, the methods further identify counter anions important in the production of salts of a compound of formula (V). In some cases, the counter anion may effect: (1) solubility of the precursor, (2) purity of the active pharmaceutical intermediate, and (3) stability of the drug product. In some cases, the trifluoroacetate anion was demonstrated to be particularly effective. In certain embodiments, as described herein, the imaging agent precursor and/or the imaging agent is present in a salt form which aids in the reactivity and/or the stability of the reaction product and/or reactant during and/or after a deprotection and/or fluorination reaction.

In some cases, the imaging agent precursor comprises a guanidine functional group which may or may not be deprotected prior to, or in some instances after, fluorination. For example, the guanidine functional group of a compound of formula (II) may or may not be deprotected prior to fluorination. That is, in some cases, an imaging agent precursor comprising a protected guanidine functional group is fluorinated, optionally followed by deprotection. Alternatively, the guanidine functional group of an imaging agent precursor is deprotected (e.g., according to the methods described herein), followed by fluorination. As described herein, in certain embodiments, the fluorine source is isotopically enriched with $^{18}F$.

In certain embodiments, a compound comprising formula (II) is first fluorinated then deprotected. In certain embodiments, method comprises fluorinating a compound comprising formula (II):

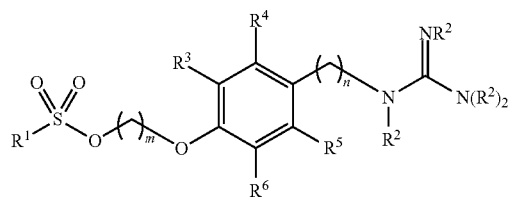

or a salt, free base, or combination thereof, under conditions suitable to form a compound comprising formula (I):

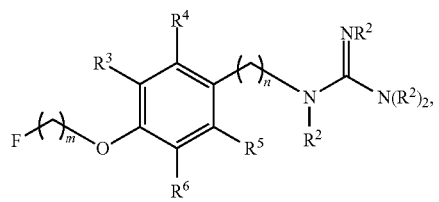

or a salt, free base, or combination thereof, wherein
$R^3$, $R^4$, $R^5$, and $R^6$ can be the same or different and are individually hydrogen, $C_1$-$C_6$ alkyl, heteroalkyl, halide, —$OR^7$, —$SR^7$, —$N(R^7)_2$, or —$C(=O)R^8$, each optionally substituted;
each $R^2$ can be the same or different and is hydrogen or a nitrogen-protecting group;
each $R^7$ can be the same or different and is hydrogen, alkyl, heteroalkyl, cycloalkyl, haloalkyl, aryl, heteroaryl, or heterocyclyl, each optionally substituted;
each $R^8$ can be the same or different and is hydrogen, alkyl, heteroalkyl, cycloalkyl, haloalkyl, heterocyclyl, aryl, heteroaryl, —OH, alkoxy, —$NH_2$, alkylamino, —SH, or alkylthiol, each optionally substituted;
m is an integer between 1 and 12, inclusive; and
n is an integer between 1 and 4, inclusive.
Each of $R^1$-$R^8$, m, and n are as defined above and described in embodiments herein, both singly and in combination, unless otherwise.

Suitable conditions for fluorinating a compound are described herein.

In some instances, following fluorination of a compound comprising formula (II) to form a compound comprising formula (I), the compound comprising formula (I) is deprotected completely or partially. In certain embodiments, the method comprises deprotecting the compound comprising formula (I):

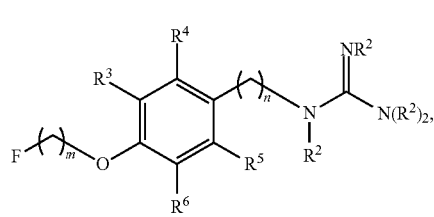

or a salt, free base, or combination thereof, provided at least one $R^2$ is not H, under conditions suitable to form a compound comprising formula (V):

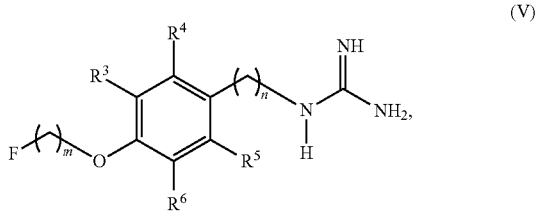

(V)

or a salt, free base, or combination thereof. Deprotection can occur, for example, under acidic conditions (e.g., pH equal to or less than 4), and optionally at elevated temperatures (e.g., ranging from about 100-150° C.).

In some cases, however, an imaging agent precursor comprising a deprotected guanidine functional group is fluorinated. For example, in certain embodiments, the method comprises fluorinating a compound comprising formula (IV):

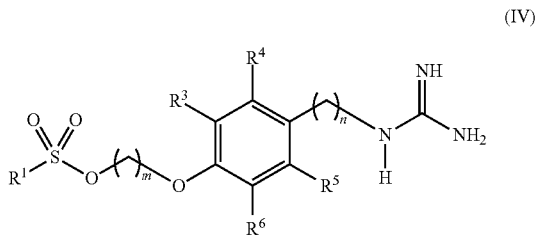

(IV)

or a salt, free base, or combination thereof, under conditions suitable to form a compound of formula (V):

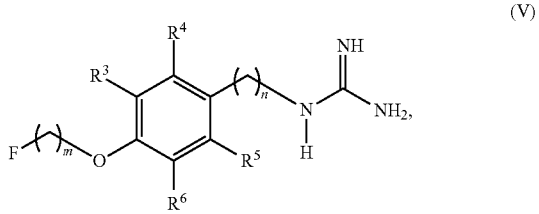

(V)

or a salt, free base, or combination thereof, wherein $R^1$ is alkyl, heteroalkyl, cycloalkyl, aryl, heteroaryl, arylalkyl, heteroarylalkyl, alkenyl, alkynyl, heterocyclyl, or haloalkyl, each optionally substituted;

$R^3$, $R^4$, $R^5$, ad $R^6$ can be the same or different and are individually hydrogen, $C_1$-$C_6$ alkyl, heteroalkyl, halide, —$OR^7$, —$SR^7$, —$N(R^7)_2$, or —$C(=O)R^8$, each optionally substituted;

each $R^7$ can be the same or different and is hydrogen, alkyl, heteroalkyl, cycloalkyl, haloalkyl, aryl, heteroaryl, or heterocyclyl, each optionally substituted;

each $R^8$ can be the same or different and is hydrogen, alkyl, heteroalkyl, cycloalkyl, haloalkyl, heterocyclyl, aryl, heteroaryl, —OH, alkoxy, —$NH_2$, alkylamino, —SH, or alkylthiol, each optionally substituted;

m is an integer between 1 and 12, inclusive; and n is an integer between 1 and 4, inclusive.

Each of $R^1$, $R^3$-$R^8$, m, and n are as defined above and described in embodiments herein, both singly and in combination, unless stated otherwise.

In some cases, it has been found, that the stability, solubility, and/or reactivity of a precursor sulfonic acid ester to a fluorinated counterpart is dependent on the derived guanidinium salt form. For example, an investigation of a series of mineral acid salts (e.g., chloride, phosphate, and sulfate salts) demonstrated variable physical properties relevant to manufacture and long term storage capacity. Salt form development revealed solubility differences in multiple solvent systems relevant to modern fluorination chemistry including, for example, MeCN, t-BuOH, and mixtures thereof. In some instances, agent precursor solubility was correlated with overall fluorination efficiency, as minimum imaging agent precursor concentration thresholds were required in order to achieve preferential rates of fluorination relative to decomposition. In addition, in some cases, the reaction rates were also variable with selection of the counter anion, even at equivalent values of solution molarity.

In some embodiments, a method for synthesizing a fluorinated compound comprises reacting, in the presence of a reagent (e.g., a carbonate or bicarbonate ion), (i) a precursor of the fluorinated compound comprising a substituent substituted with a halide or a sulfonate-containing group, with (ii) a salt comprising a fluoride species and weakly coordinating cation.

As used herein, the term "leaving group" is given its ordinary meaning in the art of synthetic organic chemistry and refers to an atom or a group capable of being displaced by a nucleophile. Examples of suitable leaving groups include, but are not limited to, halides (such as chloride, bromide, or iodide), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates In some cases, the leaving group is a sulfonic acid ester, such as toluenesulfonate (tosylate, Ts), methanesulfonate (mesylate, Ms), p-bromobenzenesulfonyl (brosylate, Bs), or trifluoromethanesulfonate (triflate, Tf). In some cases, the leaving group may be a brosylate, such as p-bromobenzenesulfonyl. In some cases, the leaving group may be a nosylate, such as 2-nitrobenzenesulfonyl. The leaving group may also be a phosphineoxide (e.g., formed during a Mitsunobu reaction) or an internal leaving group such as an epoxide or cyclic sulfate. In some embodiments, the leaving group is a sulfonate-containing group. In some embodiments, the leaving group is a tosylate group.

In some embodiments, one or more reagents is used in the reaction mixture comprising the imaging agent precursor and the fluoride species. A "reagent," also referred to as an "additive," is any chemical compound added to a reaction mixture. The reagent may be consumed or not consumed during the reaction. The reagent may be a stoichiometric or catalytic reagent. Exemplary reagents include catalysts, salts, oxidants, reductants, chelating agents, bases, acids, metals, phase transfer reagents, and others as would be appreciated by one of skill in the art.

The reagent may, in some cases, facilitate reaction between the imaging agent precursor and the fluoride species and/or may aid in stabilizing the resultant imaging agent. For example, the fluoride species may have relatively low reactivity (e.g., nucleophilicity), and addition of certain reagents may enhance the reactivity of the fluoride species. As an illustrative embodiment, a fluorine species may be a negatively charged fluoride ion (e.g., an isotopically enriched $^{18}$F ion), and a reagent may be used to bind to any positively charged counter ions present within the reaction mixture, thereby enhancing the reactivity of the fluoride ion. An example of such a reagent is a cryptand such as, but not limited to, Kryptofix (e.g., Kryptofix®-222). In some embodiments, the reagent decreases the rate of undesired side reactions, as described below.

In some cases, the reagent may be combined with the fluoride species prior to its contact with the imaging agent precursor. For example, in certain embodiments a solution comprising the fluoride species and the reagent is prepared, and the solution is added to the imaging agent precursor. In other embodiments, a solid comprising the fluoride species and the reagent is prepared, and the solid is contacted with the imaging agent precursor in solution. In certain embodiments, the fluoride species is adsorbed onto a solid support (e.g., an anion exchange column), and a solution comprising the reagent is used to elute the fluoride species from the solid support. The eluted solution is then contacted with the imaging agent precursor, or is concentrated to produce a solid, which is then contacted with the imaging agent precursor in solution.

In some embodiments, the reagent is a bicarbonate salt. As used herein, the term "bicarbonate salt" refers to a salt comprising a bicarbonate or hydrogen carbonate ion ($HCO_3^-$ ion). The bicarbonate salt may be a metal bicarbonate, such as sodium bicarbonate, calcium bicarbonate, potassium bicarbonate, and magnesium bicarbonate. In certain embodiments, the bicarbonate salt is potassium bicarbonate ($KHCO_3$). In some embodiments, the bicarbonate salt comprises a non-metal counter ion, such as ammonium bicarbonate. For example, the bicarbonate salt may be a tetraalkylammonium bicarbonate salt having the formula, $R_4NHCO_3$, wherein $R_4$ is alkyl. In some embodiments, R may be a lower alkyl, such as methyl, ethyl, propyl, butyl, pentyl, hexyl, or the like. In certain embodiments, the ammonium salt is $Et_4NHCO_3$. In other embodiments, the salt is $Me_4NHCO_3$, $i-Pr_4NHCO_3$, $n-Pr_4NHCO_3$, $n-Bu_4NHCO_3$, $i-Bu_4NHCO_3$, or $t-Bu_4NHCO_3$.

In some embodiments, the reagent is a carbonate salt. As used herein, the term "carbonate salt" refers to a salt comprising a carbonate ion ($CO_3^{-2}$ ion). The carbonate salt may be a metal carbonate, such as sodium carbonate, calcium carbonate, potassium carbonate, and magnesium carbonate. In certain embodiments, the carbonate salt is potassium carbonate ($K_2CO_3$). In some embodiments, the carbonate salt comprises a non-metal counter ion, such as ammonium carbonate. For example, the carbonate salt may be a tetraalkylammonium carbonate salt having the formula, $(R_4N)_2CO_3$, wherein R is alkyl. In some embodiments, R may be a lower alkyl, such as methyl, ethyl, propyl, butyl, pentyl, hexyl, or the like. In certain embodiments, the ammonium salt is $(Et_4N)_2CO_3$. In other embodiments, the salt is $(Me_4N)_2CO_3$, $(i-Pr_4N)_2CO_3$, $(n-Pr_4N)_2CO_3$, $(n-Bu_4N)_2CO_3$, $(i-Bu_4N)_2CO_3$, or $(t-Bu_4N)_2CO_3$.

Without wishing to be bound by any particular theory, the use of bicarbonate, carbonate, and/or ammonium salts may aid in decreasing the rate of competing reactions such as hydrolysis during nucleophilic fluorination of an imaging agent precursor.

In some embodiments, the reagent is a salt comprising a cation that forms a weakly coordinating salt with a fluoride species. As used herein, a "cation that forms a weakly coordinating salt with a fluoride species" refers to a cation that renders a fluoride species reactive within a fluorination reaction. For example, the cation may not strongly bind to the fluoride species, allowing the fluoride species to act as a nucleophile during a nucleophilic fluorination reaction. Those of ordinary skill the art would be able to select an appropriate cation that would be suitable as a weakly coordinating counter ion for a fluoride species. For example, the cation may be have a relatively large atomic radius and/or may be a weak Lewis base. In some cases, the cation may be selected to be lipophilic. In some cases, the cation may comprise one or more alkyl groups. Examples of weakly coordinating cations include cesium ions, ammonium ions, weakly coordinating salts of hexamethylpiperidindium, $S(NMe_2)_3$, $P(NMe_2)_4$, tetraaalkylphosphonium salts, tetraarylphosphonium salts, (e.g. tetraphenylphosphonium), hexakis(dimethylamino)diphosphazenium, and tris(dimethylamino)sulfonium.

In some embodiments, the reagent is an ammonium salt, i.e., a salt comprising a substituted or unsubstituted ammonium ion. In some cases, the ammonium ion is a weakly coordinating cation. In some cases, the ammonium salt has the formula, $R_4NX$, where each R can be the same or different and is alkyl, heteroalkyl, aryl, heteroaryl, or heterocyclic, each optionally substituted, and X is a negatively charged counter ion. In some cases, R is alkyl, heteroalkyl, aryl, heteroaryl, or heterocyclic, each optionally substituted. The ammonium salt may include a range of negatively charged counter ions, including halides, carbonates, and bicarbonates. Examples of ammonium salts include, but are not limited to, ammonium bicarbonate salts, ammonium hydroxide salts, ammonium acetate salts, ammonium lactate salts, ammonium trifluoroacetate salts, ammonium methanesulfonate salts, ammonium p-toluenesulfonate salts, ammonium nitrate salts, ammonium halide salts (e.g., ammonium iodide salts), and ammonium bisulfate salts.

In one set of embodiments, the ammonium salt is a tetraalkylammonium salt, such as a tetraalkylammonium bicarbonate salt. For example, the ammonium salt may have the formula, $R_4NHCO_3$, wherein each R is independently alkyl. In some cases, R is optionally substituted. In some embodiments, the alkyl group is a lower $C_1$-$C_6$ alkyl group. In some embodiments, the tetraalkylammonium salt is a basic tetraalkylammonium salt.

The salt (e.g., bicarbonate salt and/or ammonium salt) may be utilized in the reaction such that the molar ratio of the salt to the imaging agent precursor is less than or equal to about 10:1, or less than or equal to about 9:1, or less than or equal to about 8:1, or less than or equal to about 7:1 or less than or equal to about 6:1, or less than or equal to about 5:1, or less than or equal to about 4:1, or less than or equal to about 3:1, or less than or equal to about 2:1, or less than or equal to about 1:1. In some cases, the molar ratio of the salt to the imaging agent precursor is between about 3:1 and about 8:1, or between about 4:1 and about 7:1, or between about 5:1 and about 7:1, or between about 5:1 and about 8:1.

In some embodiments, the reagent is used in combination with a species capable of enhancing the reactivity of the fluoride species or otherwise facilitating conversion of the imaging agent precursor to the imaging agent. For example, the species may be a compound capable of chelating one or more ions (e.g., metal ions) that may be present within the reaction mixture. Without wishing to be bound by theory, the species may be used to chelate a counter ion to a fluoride species, such as a potassium ion, thereby increasing the reactivity (e.g., nucleophilicity) of the fluoride species. In certain embodiments, the reagent is used in combination with a multidentate ligand, such as a crown ether or a cryptand that is capable of chelating a metal ion. The multidentate ligand (e.g., cryptand) may be selected based on the metal ion to be chelated. The multidentate ligand may be, for example, 4,7,13,16,21,24-hexaoxa-1,10-diazabicyclo[8.8.8]-hexacosane (e.g., Kryptofix® 222). Other cryptands will be known to those of ordinary skill in the art.

Some embodiments involve the use of a carbonate salt in combination with 4,7,13,16,21,24-hexaoxa-1,10-diazabicyclo[8.8.8]-hexacosane. In a specific embodiment, potassium carbonate is used in combination with 4,7,13,16,21,24-hexaoxa-1,10-diazabicyclo[8.8.8]-hexacosane.

In another set of embodiments, it may be advantageous to utilize the methods described herein in the absence of a cryptand. The term "cryptand" is given its ordinary meaning in the art and refers to a bi- or a polycyclic multidentate ligand for a cation. For example, the method may be carried out using an ammonium salt, in the absence of a cryptand (e.g., 4,7,13,16,21,24-hexaoxa-1,10-diazabicyclo[8.8.8]-hexacosane). In some cases, cryptands may increase the pH of the reaction solution, which in the presence of another reagent (e.g. carbonate salt) may adversely affect the yield and/or purity of the fluorination reaction. Accordingly, carrying out the fluorination reaction, in the absence of a cryptand, and optionally in the presence of another reagent (e.g., ammonium and/or bicarbonate salt) may increase the yield and/or purity of the reaction, as described herein.

In another set of embodiments, the method is performed in the absence of a carbonate salt.

In some embodiments, the use of a salt in the reaction increases the yield by about 10%, about 20%, about 30%, about 40%, about 50%, about 60%, about 70%, about 80%, about 90%, about 100%, about 200%, about 300%, about 400%, about 500%, or greater, relative to conducting the reaction under essentially the same conditions but in the absence of a salt.

As will be understood by one of ordinary skill in the art, during fluorination, any associated anionic species (e.g., in instances where the starting material is a salt) may be exchanged. That is, the starting material may be provided as a first salt (e.g., trifluoroacetate, chloride), and the isolated product (e.g., the fluorinated product) may be isolated as a second, different salt (e.g., formate, ascorbate, citrate, or trifluoroacetate). In some cases, following formation of a salt, the counter anion may be exchanged in an additional reaction step. For example, the HCl salt of a compound may be exposed to a suitable reagent (e.g., AgOAc or AgOBz) such that the compound forms the corresponding salt of the reagent (e.g., acetate salt or benzoate salt, respectively). As another example, the TFA salt of a compound may be exposed to a suitable reagent (e.g., phosphoric acid or methanesulfonic acid) such that the compound forms the corresponding salt of the reagent (e.g., phosphate salt or methanesulfonate salt, respectively). The intermediate salt (e.g., trifluoroacetate salt or chloride salt in the above-examples) may or may not be isolated prior to exposure to the reagent.

Those of ordinary skill in the art will be able to select and/or determine the appropriate set of reaction conditions (e.g., concentration, temperature, pressure, reaction time, solvents) suitable for use in a particular application. The imaging agent may be further processed using one or more purification techniques, and may optionally be combined with additional components, such as a stabilizing agent.

In some embodiments, the imaging agent is formed as a salt (e.g., a pharmaceutically acceptable salt).

In some embodiments, a formate salt comprising formula (VI):

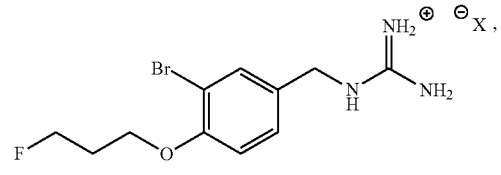

wherein $X^\ominus$ is formate, is provided.

In other embodiments, an ascorbate salt comprising formula (VII):

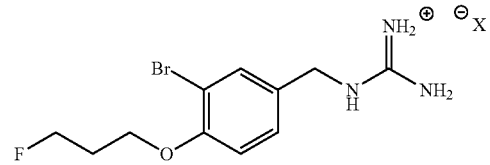

wherein $X^\ominus$ is ascorbate, is provided.

In other embodiments, a citrate salt comprising formula:

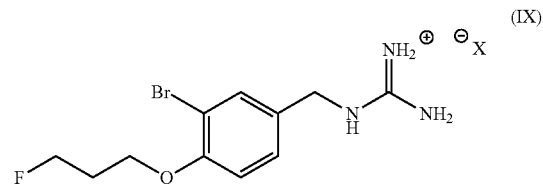

wherein $X^\ominus$ is citrate, is provided.

In other embodiments, a trifluoroacetate salt comprising formula:

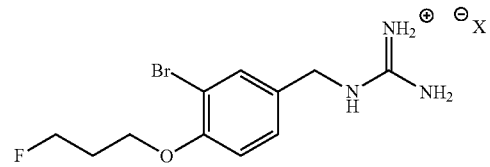

wherein $X^\ominus$ is trifluoroacetate, is provided.

In certain embodiments, the fluorine in the salt of formula (I), (VI), (VII), (IX), or (X) is isotopically enriched with $^{18}$F. In some embodiments, a pharmaceutically acceptable composition is provided.

In certain embodiments, the pharmaceutically acceptable composition comprises a salt comprising formula (VI):

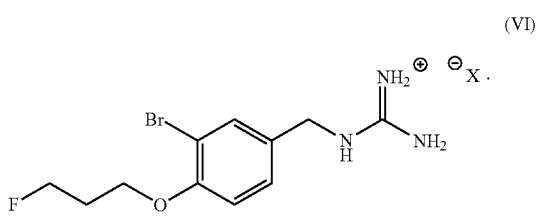

(VI)

wherein $X^{\ominus}$ is formate, or a salt comprising formula (VII):

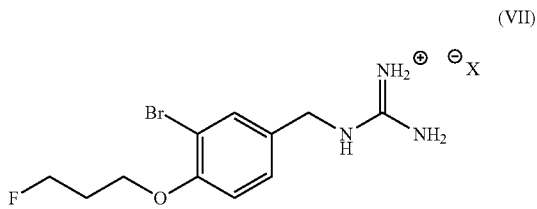

(VII)

wherein $X^{\ominus}$ is ascorbate, or combinations thereof, and optionally a pharmaceutically acceptable excipient. Other pharmaceutically acceptable compositions comprise the citrate salt of formula (IX) or the trifluoroacetate salt of formula (X).

Pharmaceutically acceptable excipients and other aspects of pharmaceutically acceptable compositions are described herein.

The formate salt and ascorbate salt have been found to have unexpected properties, including improved purity and/or stability as compared to other salt forms of the compound comprising formula (VIII):

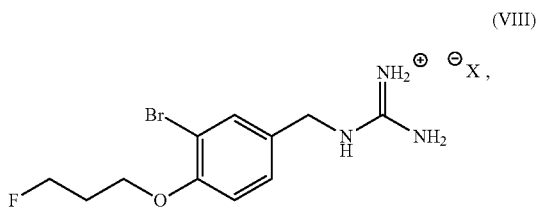

(VIII)

wherein $X^{\ominus}$ is a counter anion.

In addition, in some cases, it has been found that the salt form of the precursor of the compound of formula (VI) or (VII) may influence the purity of the final product in a pharmaceutically acceptable composition (e.g., for use as an imaging agent). For example, with respect to the formate salt (i.e., a compound of formula (VI)), this salt form has been found to have unexpected characteristics with respect to purification (e.g., the compound may be isolated in greater ease and/or in higher yields as compared to other salt forms). This may be due to the solubility characteristics of the salt. In addition, the salt form has been found to have unexpected characteristics with respect to stability. In some embodiments, the ascorbate salts of imaging agents isotopically enriched in $^{18}F$ are substantially more stable as compared to other salt forms.

In some embodiments, conversion of a compound of formula (VIII) into a suitable compound for use in a pharmaceutically acceptable composition involves three steps: (1) purification (e.g., by HPLC), (2) solvent exchange, and (3) formulation. In some cases, the compound of formula (VIII) is purified by HPLC, and the purification, retention, and/or resolution the compound is sensitive to pH and/or buffer capacity of the mobile phase. Various reagents may be contained in the mobile phase to effectively purify the compound, including acetic, citric, and/or formic acid modifiers. In a particular embodiment, the presence of formic acid in the mobile phase is particularly effective. In addition, the additive was also found to influence solvent exchange, as elution of a compound (e.g., through a C-18 Sep-Pak®) can depend on composition of the mobile phase. In some cases, formulation of the salt can be influenced by both the pH of the solution and salt form identity. pH can be adjusted to manage acute radiolytic decomposition during solvent exchange, while counter anion selection may be based on long-term antioxidant capacity.

Those of ordinary skill in the art would be able to select a source of a fluoride species suitable for use in the methods described herein. The term "fluoride species" as used herein refers to a fluoride atom or group of atoms comprising at least one fluoride atom, wherein the fluoride atom is capable of reacting with another compound (e.g., an imaging agent precursor). In some embodiments, an isotopically-enriched $^{18}F$ species may be produced by the nuclear reaction $^{18}O(p,n)^{18}F$ from proton bombardment of $[^{18}O]H_2O$ in a cyclotron. The method may involve treating a solution of the $^{18}F$ species to remove any impurities, such as unreacted $[^{18}O]H_2O$. For example, a solution of the $^{18}F$ species may be filtered through an anion exchange column, where the $^{18}F$ species is retained on the cationic resin matrix while the $[^{18}O]H_2O$ is eluted. The $^{18}F$ species is then removed by washing the anion exchange column with various mixtures of solvents and optional reagents (e.g., salt), forming an $^{18}F$-containing solution. In some cases, the anion exchange column is washed with an aqueous solution of a salt, such as $K_2CO_3$ or $Et_4NHCO_3$. In other cases, the column is washed (e.g., with aqueous $K_2CO_3$), and the resulting solution diluted (e.g., with MeCN) and/or concentrated (e.g., to dryness using elevated temperature and/or reduced pressure). Anhydrous $[^{18}F]KF$ and/or $[^{18}F]Et_4NF$ may be obtained and reacted with a compound or a salt thereof.

In some cases, the $^{18}F$-containing solution is combined with additional components prior to reaction with an imaging agent precursor. For example, one or more solvents may be added to dilute the $^{18}F$-containing solution to a desired concentration. In certain embodiments, the $^{18}F$-containing solution is diluted with acetonitrile (MeCN). In certain embodiments, the $^{18}F$-containing solution is diluted with acetonitrile (MeCN) and t-BuOH.

In some cases, the $^{18}F$-containing solution may be concentrated to dryness by exposure to elevated temperature and/or reduced pressure to form an anhydrous $^{18}F$-containing solid. In some embodiments, the $^{18}F$-containing solid may further comprise one or more reagents (e.g., salts). The chemical composition of the $^{18}F$-containing solid may depend on the number and kind of reagents used in preparation of the $^{18}F$-containing solution. For example, a solution of potassium carbonate may be used to elute the $^{18}F$ species from the anion exchange column, thereby resulting in an $^{18}F$-containing solid comprising KF. In another example, a solution of tetraethylammonium bicarbonate is used to elute the $^{18}F$ species from the anion exchange column, thereby resulting in an $^{18}F$-containing solid comprising $[^{18}F]$-$Et_4NF$.

In some cases, the solution comprising the $^{18}F$ species is heated to a temperature ranging from room temperature to about 200° C. For example, a solution comprising the $[^{18}F]$-fluoride may be heated to elevated temperatures to encourage evaporation of the solvent (e.g., to about 110° C.). In some embodiments, the solution is heated to a temperature ranging from about 90-120° C. or from about 100-150° C. In some cases, the solution is heated to about 75° C., about 85° C., about 95° C., about 105° C., about 115° C., about 125° C., or greater. In some cases, the solution is placed under a reduced pressure of about 100 mm Hg, about 125 mm Hg, about 150 mm Hg, about 175 mm Hg, about 200 mm Hg, about 225 mm Hg, about 250 mm Hg, about 275 mm Hg, about 300 mm Hg, about 325 mm Hg, about 350 mm Hg, about 375 mm Hg, about 400 mm Hg, or greater. In some cases, the solution is placed under a reduced pressure of about 100 mbar, about 125 mbar, about 150 mbar, about 175 mbar, about 200 mbar, about 225 mbar, about 250 mbar, about 275 mbar, about 280 mbar, about 300 mbar, about 325 mbar, about 350 mbar, about 375 mbar, about 400 mbar, about 450 mbar, about 500 mbar, or greater. Those of ordinary skill in the art would be able to select and/or determine conditions suitable for a particular process. In some embodiments, the solution is concentrated to dryness at about 150 mm Hg and about 115° C. In some embodiments, the solution is concentrated to dryness at about 375 mm Hg and about 115° C. In some embodiments, the solution is concentrated to dryness at about 400 mbar and about 110-150° C. In some embodiments, the solution is concentrated to dryness at about 280 mbar and about 95-115° C.

The fluoride species and/or the reagent, if present, is then contacted with the imaging agent precursor under conditions that result in conversion of the imaging agent precursor to the imaging agent product via nucleophilic fluorination. Those of ordinary skill in the art would be able to select conditions suitable for use in a particular reaction. For example, the ratio of fluoride species to imaging agent precursor may be selected to be about 1:10,000 or more, about 1:5000 or more, about 1:3000 or more, about 1:2000 or more, about 1:1000 or more, about 1:500 or more, about 1:100 or more, about 1:50 or more, about 1:10 or more, about 1:5 or more, or, in some cases, about 1:1 or more. In some embodiments, the fluoride species may be present at about 10 mol %, or about 5 mol %, or about 3 mol %, or about 2 mol %, or about 1 mol % or about 0.5 mol %, or about 0.1 mol %, or about 0.05 mol %, or about 0.01 mol % relative to the amount of imaging agent precursor. In some embodiments, the fluoride species is isotopically enriched with $^{18}F$. For example, the ratio of $^{18}F$ species to imaging agent precursor may be selected to be about 1:1,000,000 or more, or about 1:500,000 or more, or about 1:250,000 or more, or about 1:100,000 or more, or about 1:50,000 or more, or about 1:25,000 or more, or about 1:10,000 or more, about 1:5000 or more, about 1:3000 or more, about 1:2000 or more, about 1:1000 or more, about 1:500 or more, about 1:100 or more, about 1:50 or more, about 1:10 or more, about 1:5 or more, or, in some cases, about 1:1 or more.

In some embodiments, the nucleophilic fluorination reaction is carried out in the presence of one or more solvents, for example, an organic solvent, a non-organic solvent (e.g., an aqueous solvent), or a combination thereof. In some cases, the solvent is a polar solvent or a non-polar solvent. In some embodiments, the solvent is an aqueous solution, such as water. The solvent comprises at least about 0.001% water, at least about 0.01% water, at least about 0.1% water, at least about 1% water, at least about 5%, at least about 10%, at least about 20% water, at least about 30% water, at least about 40% water, at least about 50% water, or greater. In some cases, the solvent may comprise between about 0.1% and about 100% water, about 1% to about 90%, about 1% to about 70%, about 1% to about 50%, or about 10% to about 50%. In some cases, the solvent comprises no more than about 10% water, about 5% water, about 4% water, about 3% water, about 2% water, about 1% water, or about 0.5% water. In some cases, the solvent comprises between about 0.01% water and about 5% water, or between about 0.01% water and about 2% water, or between about 0.1% water and about 0.2% water.

Other non-limiting examples of solvents useful in the methods include, but are not limited to, non-halogenated hydrocarbon solvents (e.g., pentane, hexane, heptane, cyclohexane), halogenated hydrocarbon solvents (e.g., dichloromethane, chloroform, fluorobenzene, trifluoromethylbenzene), aromatic hydrocarbon solvents (e.g., toluene, benzene, xylene), ester solvents (e.g., ethyl acetate), ether solvents (e.g., tetrahydrofuran, dioxane, diethyl ether, dimethoxyethane), and alcohol solvents (e.g., ethanol, methanol, propanol, isopropanol, tert-butanol). Other non-limiting examples of solvents include acetone, acetic acid, formic acid, dimethyl sulfoxide, dimethyl formamide, acetonitrile, p-cresol, glycol, petroleum ether, carbon tetrachloride, hexamethyl-phosphoric triamide, triethylamine, picoline, and pyridine. In some embodiments, the reaction is carried out in a polar solvent, such as acetonitrile. In some cases, the solvent may be selected so as to reduce and/or minimize the formation of side products. In certain embodiments, the fluorination reaction is carried out in MeCN as the solvent. In certain embodiments, the fluorination reaction is carried out in t-BuOH as the solvent. In certain embodiments, the fluorination reaction is carried out in a mixture of MeCN and t-BuOH as the solvent. In certain embodiments, the fluorination reaction is carried out in DMF as the solvent. In certain embodiments, the fluorination reaction is carried out in DMSO as the solvent. In certain embodiments, the fluorination reaction is carried out in THF as the solvent.

In certain embodiments, an anhydrous $^{18}F$-containing solid, optionally comprising a reagent, may be contacted with a solution of an imaging agent precursor (e.g., a tosylate precursor), and the resulting solution is heated to an elevated temperature for a select period of time. The solution may be, for example, an acetonitrile solution. In other embodiments, a solution of the $^{18}F$ species and reagent, if present, is contacted with a solid imaging agent precursor or a solution of the imaging agent precursor.

Some embodiments involve contacting the imaging agent precursor with the fluoride species in a solution having a pH below about 13, below about 12, or below about 11. In some cases, the solution has a pH between about 8 and about 9, or between about 8 and about 10, or between about 7 and about 8. In certain embodiments, the pH range for the fluorination reaction is greater than about 6, or greater than about 7, or between and including 7-13, between and including 6-12, between and including 7-12, between and including 8-12, between and including 9-12, and between and including 10-12.

In some cases, the solution comprising the $^{18}F$ species, imaging agent precursor, and, optionally, reagent, is heated to an elevated temperature for a period of time. For example, the solution may be heated to about 50° C., about 60° C., about 70° C., about 80° C., about 90° C., about 100° C., about 110° C., about 120° C., about 150° C., about 170° C., about 200° C., about 225° C., about 250° C., or greater, for a period of about 5 minutes or less, about 10 minutes or less, about 20 minutes or less, about 30 minutes or less. It should be understood that other temperatures and reaction times may be used. Upon completion of the reaction, the reaction mixture is cooled (e.g., to room temperature) and optionally diluted with a solvent, such as water, or mixtures of solvents, such as water/acetonitrile. In some embodiments, the reaction mixture is heated to elevated temperatures to encourage evaporation of the solvent (e.g., to about 95° C.). In some embodiments, the solution is heated to a temperature ranging from about 55-125° C. In some cases, the solution is heated to about 65° C., about 75° C., about 85° C., about 95° C., about 105° C., about 115° C., or greater. In some cases, the solution is placed under a reduced pressure of about 100 mm Hg, about 125 mm Hg, about 150 mm Hg, about 175 mm Hg, about 200 mm Hg, about 225 mm Hg, about 250 mm Hg, about 275 mm Hg, about 300 mm Hg, about 325 mm Hg, about 350 mm Hg, about 375 mm Hg, about 400 mm Hg, or greater. In some cases, the solution is placed under a reduced pressure of about 100 mbar, about 125 mbar, about 150 mbar, about 175 mbar, about 200 mbar, about 225 mbar, about 250 mbar, about 275 mbar, about 280 mbar, about 300 mbar, about 325 mbar, about 350 mbar, about 375 mbar, about 400 mbar, about 450 mbar, about 500 mbar, or greater. Those of ordinary skill in the art would be able to select and/or determine conditions suitable for a particular process. In some embodiments, the solution is concentrated to dryness under a flow of inert gas at about 95° C.

Upon completion of the fluorination reaction, the resulting imaging agent is optionally subjected to one or more purification steps. In some cases, the imaging agent may be reconstituted in a solvent prior to purification (e.g., by chromatography such as HPLC). In some cases, the imaging agent is dissolved in water, acetonitrile, or combinations thereof. In some embodiments, following formation of a solution comprising the imaging agent and the solvent and prior to purification (e.g., by HPLC), the solution is heated. In a particular embodiment, the imaging agent is reconstituted in a water/acetonitrile mixture and heated (e.g., to a temperature of about 90-100° C.) for about 1 minute, about 3 minutes, about 5 minutes, about 10 minutes, about 20 minutes, about 30 minutes, or more. Following the heating of the mixture, the solution may be optionally cooled prior to purification.

Deprotection

Those of ordinary skill in the art will be aware of suitable conditions for deprotecting guanidine functional groups. As discuss below, the protecting groups may be removed before or after fluorination. In some embodiments, the suitable conditions comprise exposing a compound comprising a protected guanidine functional group to an acid. The acid may be added neat or in a solution (e.g., such that the acid is at a concentration of about 0.1 M, about 0.2 M, about 0.3 M, about 0.4 M, about 0.5 M, about 0.75 M, or about 1.0 M). In certain embodiments, the nitrogen-protecting group is t-butyloxycarbonyl, and the acid used for the deprotecting step is trifluoroacetic acid. In certain embodiments, following deprotection, the compound is a salt (e.g., a trifluoroacetate salt).

In some cases, the suitable conditions for deprotection comprise acidic conditions. The acid may be provided at a ratio of about 2:1, about 1:1, about 1:2, about 1:3, or about 1:4 compound:acid. In certain embodiments, the pH range for deprotection of imaging agent precursors such as compounds of Formula (II) (or alternatively of protected fluorinated imaging agents of the invention) may be equal to or less than about 4, including equal to or less than about 3, equal to or less than about 2, and equal to or less than about 1.

The conditions may comprise one or more solvents. Non-limiting examples of solvents are provided herein. The reaction may be carried out at any suitable temperature, and in certain embodiments, the deprotection reaction is carried out at room temperature or above room temperature. The product may be analyzed, isolated, and/or purified using techniques known to those of ordinary skill in the art (e.g., column chromatography, HPLC, NMR, MS, IR, UV/Vis). In some cases, the product is isolated as a salt (e.g., via filtration, crystallization). In certain embodiments, the salt is an ascorbate salt. In certain embodiments, the salt is a formate salt. In other embodiments, the salt is a citrate salt or a trifluoroacetate salt.

Purification and Formulation

In some cases, the synthesis, purification, and/or formulation of an imaging agent (e.g., a compound comprising formula (I) or (V)) is performed using an automated reaction system optionally comprising a cassette, wherein the cassette comprises a synthesis module, and/or a purification module, and/or a formulation module. Automated reaction systems and cassettes are described herein.

Purification and isolation may be performed using methods known to those skilled in the art, including separation techniques like chromatography, or combinations of various separation techniques known in the art, for example, extractions, distillation, and crystallization. In one embodiment, high performance liquid chromatography (HPLC) is used with a solvent, or mixture of solvents, as the eluent, to recover the product. In some cases, the eluent includes a mixture of water and acetonitrile, such as a 20:80 water:acetonitrile mixture. The content of water in the eluent may vary from, for example, about 1% to about 30%. In some cases, HPLC purification may be performed using a C18 column. The product may be analyzed (e.g., by HPLC) to determine yield (e.g., radiochemical yield) and/or radiochemical purity. The radiochemical purity may be greater than about 50%, about 60%, about 70%, about 80%, about 90%, about 95%, about 97%, about 98%, about 99%, or more. The percent yield of a product may be greater than 10%, greater than 20%, greater than 30%, greater than 40%, greater than 50%, greater than about 60%, greater than about 70%, greater than about 75%, greater than about 80%, greater than about 85%, greater than about 90%, greater than about 92%, greater than about 95%, greater than about 96%, greater than about 97%, greater than about 98%, greater than about 99%, or greater. In some embodiments, the radiochemical yield ranges from 15-50%.

The product may be further processed using additional purification techniques, such as filtration. In some cases, the imaging agent is purified using HPLC, to produce a solution of HPLC mobile phase and the imaging agent. The HPLC mobile phase may be subsequently exchanged for a solution of ascorbic acid or a salt thereof, and ethanol solution, by filtration through a C-18 resin (e.g., C18 Sep-Pak® cartridge). In some embodiments, the solution of the HPLC mobile phase and the imaging agent is filtered through a C-18 resin, where the imaging agent remains on the resin and the other components, such as acetonitrile and/or other solvents or components, are removed via elution. The C-18 resin may be further washed with a solution of ascorbic acid or a salt thereof, and the filtrate discarded. To recover the purified imaging agent, the C-18 resin is washed with a solvent, such as ethanol, and the resulting solution is optionally further diluted with an ascorbic acid solution or a salt thereof, as described herein.

Optionally, the recovered product is combined with one or more stabilizing agents, such as ascorbic acid or a salt thereof. For example, a solution comprising the purified imaging agent may be further diluted with a solution of ascorbic acid or a salt thereof. As described herein, a formulation may be prepared via an automated reaction system comprising a cassette.

In some cases, a solution comprising the imaging agent product may be sterile filtered (e.g., using a 13 mm diameter, Millipore, Millex PVDF 0.22 µm sterilizing filter) into a sterile product vial. The sterile product vial may be a commercially available, pre-sterilized unit that is not opened during the production process, as any imaging agents (or other components) may be aseptically inserted through the septum prior to use. Those of ordinary skill in the art would be able to select suitable vials and production components, including commercially available, pre-sterilized units comprising a 0.22 μm pore size membrane venting filter and quality control sampling syringes.

Following aseptic filtration, individual doses may be filled in syringes, labeled, and shipped to a clinical site. Dosing administration techniques, kits, cassettes, methods and systems (e.g., automated reaction systems) for synthesis of the imaging agent, and testing procedures are described herein. In some embodiments, the product is dispensed into a 3 or 5 mL syringe and labeled for distribution. Labels may be prepared at a radiopharmacy and applied to a syringe shield and shipping container. Additional labels may be provided in the shipping container for inclusion in clinical site records.

Uses of Imaging Agents

In another aspect, the present invention provides methods of imaging, including methods of imaging a subject that includes administering a composition or formulation that includes an imaging agent of the invention (i.e., a compound of Formula (I), including a compound of Formula (V), such as, but not limited to, imaging agent-1) to the subject by injection, infusion, or any other method of administration, and imaging a region of interest of the subject. Regions of interest may include, but are not limited to, the heart, a portion of the heart, the cardiovascular system, cardiac vessels, blood vessels (e.g., arteries and/or veins), brain, pancreas, adrenal glands, other organs, and tumors. As described herein, imaging agent-1 comprises the formula:

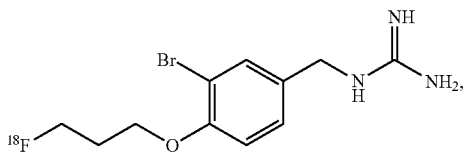 [SMILES: N=C(N)NCc1ccc(OCCC[18F])c(Br)c1]

or a pharmaceutically acceptable salt, free base, or combination thereof. In some embodiments, a pharmaceutically acceptable salt of imaging agent-1 comprises the formula:

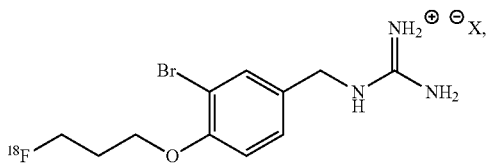 [SMILES: NC(=[NH2+])NCc1ccc(OCCC[18F])c(Br)c1 ; "X,"]

wherein $X^\ominus$ is a counter anion. In certain embodiments, $X^\ominus$ is formate or ascorbate. In some embodiments, the $X^\ominus$ is citrate or trifluoroacetate.

In some embodiments, methods of this disclosure include (a) administering to a subject a composition that includes an imaging agent of the invention including, but not limited to, imaging agent-1, and (b) acquiring at least one image of at least a portion of the subject. In some cases, the step of acquiring employs positron emission tomography (PET) for visualizing the distribution of the imaging agent within at least a portion of the subject. As will be understood by those of ordinary skill in the art, imaging using methods of this disclosure may include full body imaging of a subject, or imaging of a specific body region, organ, or tissue of the subject that is of interest. For example, if a subject is known to have, or is suspected of having myocardial ischemia, methods of this disclosure may be used to image the heart of the subject. In some embodiments, imaging may be limited to the heart or may include the heart and its associated vasculature.

In some embodiments, imaging agents of the invention, including but not limited to imaging agent-1, are used to monitor and/or assess certain aspects of the sympathetic nervous system (SNS). The SNS plays a role in normal cardiac regulation and/or the pathogenesis of heart failure development and/or progression. Generally, following myocardial insult (e.g., myocardial infarction, valve regurgitation, hypertension), compensatory activation of the SNS is induced to help maintain sufficient cardiac output. Sustained elevation of the cardiac SNS can cause elevated cardiac norepinephrine (NE) release, down regulation of the beta1 adrenergic receptor, and/or down regulation of the NE transporter (NET), which can result in spillover of NE. Elevated levels of NE can be attributed to cardiac myocyte hypertrophy, fibroblast activation, collagen deposition, and/or myocyte apoptosis, which can result in ventricle remodeling and/or susceptibility to arrhythmia.

In some embodiments, assessment of the changes and/or the presence of a neurotransmitter in a subject, and certain parameters relating to the neurotransmitter provides feedback relating to cardiac events. For example, assessment of NET in a subject can be used to provide feedback relating to cardiac events and/or cardiac exposure to NE. In some cases, the neurotransmitter is a monoamine other than NE.

In some embodiments, the neurotransmitter is NE. Utilizing an imaging agent that targets NET permits imaging of the location, concentration, density, and/or distribution of NETs and also can be used to detect changes in NETs over time, for example, by acquiring a first NET image in a subject or region of a subject; obtaining a subsequent NET image of the subject or the region of the subject and comparing the first and subsequent images. Differences between the images can provide information on the change in NET status in the subject or region of the subject. Changes in a NET parameter (e.g., location, density, concentration, and/or distribution) over time may be assessed and correlated with disease onset, progression, and/or regression. In some embodiments, a method comprises administering a dose of a pharmaceutically acceptable composition (e.g., imaging agent-1) to a subject, and acquiring at least one image of a portion of the subject, wherein the image allows for the assessment and/or detection of NET in the subject. In some cases, the detection comprises detection of the level (e.g., concentration) of NET, detection of the density of NET, detection of NET function, and/or detection of the localization of NET.

In some embodiments, changes in NET (e.g., density, localization, concentration, function) may be used to assess the presence and/or absence of a condition, disease, and/or disorder. For example, in some cases, changes in NET may be used to assess cardiac sympathetic innervation and/or myocardial sympathetic function in a subject. For example, an increase or decrease in NET concentration in a portion of the subject (e.g., heart) may indicate the cardiac sympathetic innervation in that portion of the subject. In some cases, subjects with impaired NET functions are correlated with heart failure and/or rapid myocardial reorganization.

In some embodiments, an imaging agent that targets NET may also be used to observe, estimate and/or quantify localized blood flow to tissue. More specifically, there may be instances in which the level of imaging agent (or radioactivity) observed in the myocardium, is decreased compared to normal or below threshold. There may be various causes of this decreased signal, one of which may be reduced blood flow to and through the myocardium. In order to determine the cause, the subject may be imaged using a different imaging agent and/or a different imaging modality suitable for detecting blood flow. Comparison of images obtained using the different methods can reveal whether the decrease or absence of signal from the imaging agent that targets NET is attributable to blood flow rather than to a difference in NET level, activity and the like. In other embodiments of the invention, the myocardium may be imaged serially, for example immediately after administration of the imaging agent, in order to observe movement of the imaging agent into the heart. Such serial images should yield information about blood flow through the heart. Later images are also obtained as these reveal a more steady state of blood flow into and out of the heart as well as blood retention in the heart. In this way, alterations in global, local, or regional blood flow may be distinguished from local or regional changes in NET density, localization, concentration, and function as described above. In some embodiments, an imaging agent that targets NET is used to assess the ability of a therapeutic agent and/or treatment to modify NET. For example, images acquired from a subject administered an imaging agent of the including but not limited to imaging agent-1 before therapeutic treatment can be compared to images acquired from the same subject after therapeutic treatment of the subject to determine if the treatment has affected the location, concentration, and/or density of NET for the subject. Similarly, images at different times and/or before and after treatment can be used to detect changes in NET in a subject over time and/or with treatment.

In some aspects, global images (e.g., global NET images) are acquired, and in other aspects of the invention, regional images (e.g., regional NET images) are acquired following administration of an imaging agent that targets NET, wherein a global image is an image of all or substantially all of an organ (e.g., heart, kidney, pancreas), and a regional image is an image of only a portion of an organ. Images can be acquired using an image collection system such as a PET system, a SPECT system, or any other suitable imaging system.

In some embodiments, images may be acquired over a single time interval, and in other embodiments, they may be acquired as a series of images of the same or different acquisition durations beginning either at the time of administration or at a later time.

In some embodiments, methods of diagnosing or assisting in diagnosing a disease or condition, assessing efficacy of a treatment of a disease or condition, or imaging of a subject with a known or suspected cardiovascular disease or condition changing sympathetic innervations are provided. A cardiovascular disease can be any disease of the heart or other organ or tissue supplied by the vascular system. The vascular system includes coronary arteries, and all peripheral arteries supplying the peripheral vascular system and the brain, as well as veins, arterioles, venules, and capillaries. In cases, cardiac innervation may be examined, as abnormalities in cardiac innervation have been implicated in the pathophysiology of many heart diseases, including sudden cardiac death, congestive heart failure, diabetic autonomic neuropathy, myocardial ischemia, and cardiac arrhythmias. Other non-limiting examples of cardiovascular diseases of the heart include diseases such as coronary artery disease, myocardial infarction, myocardial ischemia, angina pectoris, congestive heart failure, cardiomyopathy (congenital or acquired), arrhythmia, or valvular heart disease. In some embodiments, the methods disclosed herein are useful for monitoring and measuring cardiac innervation. For example, a method described herein can determine the presence or absence of cardiac innervation. Conditions of the heart may include damage, not brought on by disease but resulting from injury e.g., traumatic injury, surgical injury. Methods described herein can be used in some embodiments to determine global or regional changes in cardiac sympathetic innervation.

In some cases, a subject whom an imaging agent of the invention may be administered may have signs or symptoms suggestive of a disease or condition associated with abnormalities in cardiac innervation. In some cases, use of the imaging agent can be used to diagnose early or pre-disease conditions that indicate that a subject is at increased risk of a disease. Imaging methods described herein may be used to detect cardiac innervation in subjects already diagnosed as having a disease or condition associated with abnormalities in cardiac innervation, or in subjects that have no history or diagnosis of such a disease or condition. In other instances, the methods may be used to obtain measurements that provide a diagnosis or aid in providing a diagnosis of a disease or condition associated with abnormalities in cardiac innervation. In some instances, a subject may be already undergoing drug therapy for a disease or condition associated with abnormalities in cardiac innervation, while in other instances a subject may be without present therapy for a disease or condition associated with abnormalities in cardiac innervation. In some embodiments, the method may be used to assess efficacy of a treatment for a disease or condition. For example, the heart can be visualized using contrast/imaging agents described herein before, during, and/or after treatment of a condition affecting the heart of a subject. Such visualization may be used to assess a disease or condition, and aid in selection of a treatment regimen, e.g. therapy, surgery, medications, for the subject.

In some embodiments, a compound of the present invention is employed for determining the presence or absence of a tumor in a subject. In some embodiments, the tumor is a NET-expressing tumor. In some embodiments, an imaging agent of the invention is employed for determining the response to therapy of a tumor in a subject. Methods for determining the presence of a tumor and/or for determining the response to therapy of a tumor in a subject can follow the same or similar methods as described for methods of imaging a subject.

In some embodiments, an imaging agent of the invention (e.g., imaging agent-1) is used as an imaging agent in combination with positron emission tomography (PET) or with other imaging methods including, but not limited to, single photon emission computed tomography (SPECT) imaging. In some cases, PET imaging may be used in cardiac sympathetic neuronal imaging in a subject following administration of imaging agent-1 to the subject. For example, imaging agent-1 may be administered to a subject and imaged in the subject using PET. As will be known to those of ordinary skill in the art, PET is a non-invasive technique that allows serial images and measurements to be obtained in a single subject over a time period. PET imaging used may be carried out using known systems, methods, and/or devices. In some embodiments, PET imaging is conducted using a cardiac imaging system. A cardiac imaging system may include PET imaging functionality; and a control unit configured to drive the imaging functionality to perform a PET imaging procedure on a portion of the subject of interest before, during and/or after administration of imaging agent-1 to the subject. In some cases, the control unit is configured to drive the imaging functionality to perform a PET imaging procedure. The control unit may comprise a computer system and/or software. In such a case, the computer system may be programmed or configured to execute the required methods for acquiring and/or analyzing the images. Further, the system may include a data storage device that is readable by a machine, embodying a set of instructions executable by the machine to perform the required methods of acquiring and/or analyzing the images.

Imaging systems (e.g., cardiac imaging systems) and components thereof will be known to those of ordinary skill in the art. Many imaging systems and components (e.g., cameras, software for analyzing the images) are known and commercially available, for example, a Siemens Biograph-64 scanner or other scanner suitable for imaging. In some embodiments, image data is acquired in list mode, and such list data may be used to create static, dynamic, or gated images. An appropriate period of time for acquiring images can be determined by one of ordinary skill in the art, and may vary depending on the cardiac imaging system, the imaging agent (e.g., amount administered, composition of the imaging agent, subject parameters, area of interest). As used herein a "period of acquiring images" or an "image acquisition period" may be a period of time for obtaining a single continuous image, and/or may be a period during which one or more individual discrete images are obtained. Thus, a period of image acquisition can be a period during which one or more images of one or more regions of a subject are acquired.

The term "list mode," as used herein, is given its ordinary meaning in the art. With respect to PET, list mode is a form in which the data that is used to create a PET image can be initially collected. In list mode, each of or a portion of coincidence events (i.e., each of a portion of detected photon pairs) generates an entry in a list of events. Each entry includes various information including, but not limited to, which detectors were involved, the energy of the photons detected, the time of detection, and/or whether there was a cardiac gating mark. The information can be converted into one or more images by the process of rebinning and/or histogramming, in which all or a portion of the events for each pair of detectors is summed, followed by the resulting set of projections (e.g., in the form of a sinogram wherein for each slice, each horizontal line in the sinogram represents the projections for coincidences at a given angle). List mode may be contrasted with "histogram mode" in which the summations are completed during acquisition so that the only raw data is the sinogram. In some embodiments, histogram mode may be employed.

In some embodiments, a period of image acquisition after administration of imaging agent-1 to a subject may be between about 0 seconds and about 60 minutes, between about 1 minute and about 30 minutes, between about 5 minutes and about 20 minutes, or at least about 1 minute, at least about 3 minutes, at least about 5 minutes, at least about 6 minutes, at least about 7 minutes, at least about 8 minutes, at least about 9 minutes, at least about 10 minutes, at least about 15 minutes, at least about 20 minutes, at least about 30 minutes, at least about 45 minutes, at least about 60 minutes, at least about 90 minutes, at least about 2 hours, at least about 3 hours, at least about 4 hours, at least about 5 hours, or greater. In some embodiments, a period of image acquisition may begin prior to administration of imaging agent-1 to a subject. For example, a period of image acquisition may begin more than about 10 minutes, about 5 minutes, about 4, minutes, about 3 minutes, about 2 minutes, about 1 minute, about 0 minutes prior to administration of imaging agent-1 to the subject. In some embodiments, imaging may be continuous over the imaging period of time, or images may be acquired at intervals such as in periodic or gated imaging.

In some embodiments, an imaging agent of the invention (e.g., imaging agent-1) is provided in ethanol/ascorbic acid. In some embodiments, an imaging agent of the invention (e.g., imaging agent-1) is provided as a composition comprising ethanol, ascorbic acid (e.g., as sodium ascorbate), and water. In some cases, the composition comprises less than about 20 weight % ethanol, less than about 15 weight % ethanol, less than about 10 weight % ethanol, less than about 8 weight % ethanol, less than about 6 weight % ethanol, less than about 5 weight % ethanol, less than about 4 weight % ethanol, less than about 3 weight % ethanol, or less ethanol. In some cases, the composition comprises less than about 100 mg/mL, less than about 75 mg/mL, less than about 60 mg/mL, less than about 50 mg/mL, less than about 40 mg/mL, less than about 30 mg/mL, less than about 20 mg/mL, less than about 10 mg/mL, or less ascorbic acid (e.g., sodium ascorbate) in water. A non-limiting, exemplary formulation of imaging agent-1 includes about 5 weight % ethanol and about 50 mg/ml ascorbic acid. In a particular non-limiting embodiment, a compound comprising formula (VI) or (VII) is provided as a solution in water comprising less than about 5 weight % ethanol and less than about 50 mg/mL sodium ascorbate in water. As will be understood by those of ordinary skill in the art, in the presence of ascorbic acid, at least a portion of the imaging agent-1 may be present as the ascorbate salt such that imaging agent-1 has the formula:

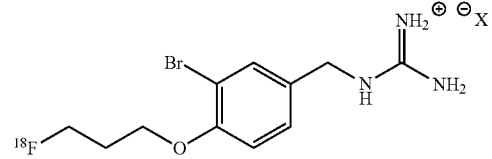

wherein $X^\ominus$ is ascorbate.

Additional components of a composition comprising an imaging agent of the invention (e.g., imaging agent-1) may be selected depending on the mode of administration to the subject. Various modes of administration will be known to one of ordinary skill in the art which effectively deliver the pharmacological agents of the invention to a desired tissue, cell, organ, or bodily fluid. In some embodiments, an imaging agent of the invention (e.g., imaging agent-1) is administered intravenously (e.g., intravenous bolus injection) using methods known to those of ordinary skill in the art. As used herein, a dose that is "administered to a subject" means an amount of the imaging agent, e.g. imaging agent-1, that enters the body of the subject.

In some embodiments, the volume of the administered imaging agent may be between 0 and about 3 mL, between about 3 mL and about 5 mL, or between about 5 mL and about 10 mL.

In some embodiments, due to factors such as partial retention of imaging agent such as imaging agent-1 in a syringe, tubing, needles, or other equipment used to administer the imaging agent to a subject, the amount of an imaging agent such as imaging agent-1 that is measured or determined to be in the a syringe or other equipment prepared for administration may be more than the amount in the dose that is administered to the subject. In some embodiments, an injection of an imaging agent is followed by a flushing injection of normal saline into the subject, using the same tubing, needle, port, etc., used for administration of the imaging agent.

Flushing may be performed immediately following administration of the imaging agent-1, or up to about 1 min, about 2 min, about 3 min, about 5 min, or more after the administration. In some embodiments, flushing may be performed between 0 and 10 seconds, between 10 seconds and 25 seconds, or between 25 seconds and 60 seconds.

The volume of saline or other agent for flushing may be up to about 5 ml, about 6 ml, about 7 ml, about 8 ml, about 9 ml, about 10 ml, about 15 ml, about 20 ml, or more. As will be understood by those of ordinary skill in the art, in embodiments where imaging agent-1 is administered using a syringe or other container, the true amount of imaging agent-1 administered to the subject may be corrected for any imaging agent-1 that remains in the container. For example, the amount of radioactivity remaining in the container, and tubing and needle or delivery instrument that carried the imaging agent from the container and into the subject can be determined after the imaging agent has been administered to the subject and the difference between the starting amount of radioactivity and the amount remaining after administration indicates the amount that was delivered into the subject. In some cases, the container or injection device (e.g., catheter, syringe) may be rinsed with a solution (e.g., saline solution) following administration of imaging agent-1.

A composition of an imaging agent of the invention (e.g., imaging agent-1) for injection may be prepared in an injection syringe. Imaging agents may be prepared by a radiopharmacy (e.g., using the methods described herein) and/or a PET manufacturing center and provided to a health-care professional for administration. A dose of imaging agent-1 may be diluted with saline (e.g., as described herein), if needed to obtain a practical dose volume. For example, if the activity concentration of imaging agent-1 is so high that only about 0.1 mL is needed for an appropriate dose for a subject, the solution can be diluted, e.g., with sterile saline, so the syringe contains about 0.5 ml to about 6 ml or more ml of an imaging agent-1 solution for administration. In some embodiments, an injection volume for imaging agent-1 is between about 0.5 and about 5 ml, about 1 and about 4 ml, about 2 and about 3 ml, at least about 0.5 ml, about 1 ml, about 2 ml, about 3 ml, about 4 ml, about 5 ml, about 6 ml, about 7 ml, about 8 ml, about 9 ml, about 10 ml, or more. Those of skill in the art will recognize how to dilute imaging agent-1 to produce a sufficient dose volume for administration. In some aspects, imaging agent-1 is provided in a container such as a vial, bottle, or syringe, and may be transferred, as necessary, into a suitable container, such as a syringe for administration.

Components of a composition comprising an imaging agent of the invention (e.g., imaging agent-1) may be selected depending on the mode of administration to the subject. Various modes of administration that effectively deliver imaging agents of the invention to a desired tissue, cell, organ, or bodily fluid will be known to one of ordinary skill in the art. In some embodiments, the imaging agent is administered intravenously (e.g., intravenous bolus injection) using methods known to those of ordinary skill in the art.

The useful dosage of the imaging agent to be administered and the particular mode of administration will vary depending upon such factors as age, weight, and particular region to be imaged, as well as the particular imaging agent used, the diagnostic use contemplated, and the form of the formulation, for example, suspension, emulsion, microsphere, liposome, or the like, as described herein, and as will be readily apparent to those skilled in the art.

In one embodiment, imaging agent-1 is administered by intravenous injection, usually in saline solution, at a dose of between about 0.1 and about 20 mCi (and all combinations and subcombinations of dosage ranges and specific dosages therein, and as described below), or between a dose of about 0.5 and about 14 mCi. Imaging is performed using techniques well known to the ordinarily skilled artisan and/or as described herein.

Based on dosing studies, the desirable maximum dose administered to a subject may be based on determining the amount of imaging agent of the invention (e.g., imaging agent-1), which limits the radiation dose to about 5 rem to the critical organ (e.g., urinary bladder) and/or about 1 rem effective dose (ED) or lower, as will be understood by those of ordinary skill in the art. In some embodiments of the invention, the maximum desirable dose or total amount of imaging agent-1 administered is between about 8 mCi and about 13 mCi. In some embodiments of the invention, the maximum desirable dose or total amount of imaging agent-1 administered is between about 10 mCi and about 13 mCi. In some embodiments of the invention, the maximum desirable dose or total amount of imaging agent-1 administered is between about 8 mCi and about 10 mCi. In some embodiments, a desirable dose may be less than or equal to about 15 mCi, less than or equal to about 14 mCi, less than or equal to about 13 mCi, less than or equal to about 12 mCi, less than or equal to about 11 mCi, or less than or equal to about 10 mCi over a period of time of up to about 10 minutes, about 30 minutes, about 1 hour, about 2 hours, about 6 hours, about 12 hours, about 24 hours, or about 48 hours. In some embodiments, the maximum dose of imaging agent-1 administered to a subject may be less than about 14 μg per about 50 kg of body weight per day. That is in some embodiments of the invention, the maximum dose of a composition comprising imaging agent-1 administered to a subject may be less than about 0.28 μg of a imaging agent-1 per kg of body weight per day.

In some embodiments, the total amount of imaging agent-1 administered to a subject is between about 0.1 mCi and about 30 mCi, or between about 0.5 mCi and about 20 mCi. In some embodiments, the total amount of imaging agent-1 administered to a subject is less than or equal to about 50 mCi, less than or equal to about 40 mCi, less than or equal to about 30 mCi, less than or equal to about 20 mCi, less than or equal to about 18 mCi, less than or equal to about 16 mCi, less than or equal to about 15 mCi, less than or equal to about 14 mCi, less than or equal to about 13 mCi, less than or equal to about 12 mCi, less than or equal to about 10 mCi, less than or equal to about 8 mCi, less than or equal to about 6 mCi, less than or equal to about 4 mCi, less than or equal to about 2 mCi, less than or equal to about 1 mCi, or less than or equal to about 0.5 mCi. The total amount administered may be determine based on a single dose or multiple doses administered to a subject within a time period of up to or at least about 30 seconds, about 1 minute, about 10 minutes, about 30 minutes, about 1 hour, about 2 hours, about 6 hours, about 12 hours, about 24 hours, about 48 hours, or about 1 week.

In some aspects of the invention, between about 10 and about 13 mCi, or between about 8 to about 10 mCi of imaging agent-1 is administered to a subject, and a first period of image acquisition begins at the time of administration (e.g. injection) or begins at more than about 0 minutes, about 1 minute, about 2 minutes, about 3 minutes, about 4 minutes, about 5 minutes, prior to the administration of the imaging agent-1. In some embodiments of the invention, the first imaging continues for at least about 5 minutes, about 10 minutes, about 15 minutes, about 30 minutes, about 45 minutes, about 60 minutes, about 75 minutes, about 90 minutes, about 105 minutes, about 120 minutes, or longer. Following the first period of imaging, the subject may undergo one or more additional imaging acquisition periods during up to about 1, about 2, about 3, about 4, about 5, about 6, or more hours after the administration of imaging agent-1. One or more additional image acquisition periods may have a duration of between about 3 and about 40 minutes, about 5 and about 30 minutes, about 7 and about 20 minutes, about 9 and about 15 minutes, and may be for about 10 minutes. The subject, in some embodiments, may return once, twice, or three or more times for additional imaging following the first injection of imaging agent-1 wherein a second, third, or more, injections of imaging agent-1 may be administered. A non-limiting example of an administration and image acquisition method for imaging agent-1 for a subject comprises injection of between about 10 and about 13 mCi, or between about 8 to about 10 mCi of imaging agent-1 to the subject, with image acquisition starting less than about 10 minutes before the injection and continuing for about 60 minutes. In some embodiments, the subject undergoes additional image acquisition for about 10 minutes, or for about 20 minutes, or for about 30 minutes, or for about 40 minutes, or for about 50 minutes, or for about 60 minutes, at about one hour, or about two hours, or about 3 hours, or about 4 hours, and at about 4 hours, or about 5 hours, or about 6 hours, or about 7 hours, or about 8 hours, after the injection of imaging agent-1.

In some embodiments, studies may also be performed using an agent specialized for tissue blood flow using methods known to those familiar with the art. The images from these studies may then be used to distinguish abnormalities seen in images from, for example, agent-1, due to changes in NET from those due to alterations of global, regional or local blood flow.

Exemplary Cassettes and Reaction Systems

In some embodiments, systems, methods, kits, and cassettes are provided for the synthesis of an imaging agent of the invention (e.g., imaging agent-1). In some embodiments, an imaging agent may be prepared using an automated reaction system comprising a disposable or single use cassette. The cassette may comprise all the non-radioactive reagents, solvents, tubing, valves, reaction vessels, and other apparatus and/or components necessary to carry out the preparation of a given batch of imaging agent. The cassette allows the reaction system to have the flexibility to make a variety of different imaging agents with minimal risk of cross-contamination, by simply changing the cassette. By the term "cassette" is meant a piece of apparatus designed to fit removably and interchangeably onto automated reaction systems, in such a way that mechanical movement of moving parts of the automated reaction system controls the operation of the cassette from outside the cassette, i.e., externally. In certain embodiments, a cassette comprises a linear arrangement of valves, each linked to a port where various reagents, cartridges, syringes, and/or vials can be attached, by either needle puncture of a septum-sealed vial, or by gas-tight, marrying joints. Each valve may have a male-female joint which interfaces with a corresponding moving arm of the automated synthesizer. External rotation of the arm can control the opening or closing of the valve when the cassette is attached to the automated reaction system. Additional moving parts of the automated reaction system are designed to clip onto syringe plunger tips, and thus raise or depress syringe barrels. An automated reaction system may further include a controller and one or more controllable valves in electrical communication with the controller. An automated reaction system may also include additional vessels, valves, sensors, heaters, pressurizing elements, etc., in electrical communication with the controller. An automated reaction system may be operated by a controller using suitable software for control of valve openings and closings, heating, cooling, pressure levels, fluid movement, flow rate, etc. The automated reaction system may optionally include a computer operating system, software, controls, etc., or other component. In addition, the automated reaction system may comprise a mount for the cassette.

Examples of automated reaction systems (e.g., a nucleophilic reaction system), include, but are not limited to, the Explora GN or RN synthesis system (Siemens Medical Solutions USA, Inc.), GE-Tracerlab-MX synthesis system (GE Healthcare), Eckert & Ziegler Modular-Lab Synthesis system, etc., which are commonly available at PET manufacturing facilities.

Figure 2:
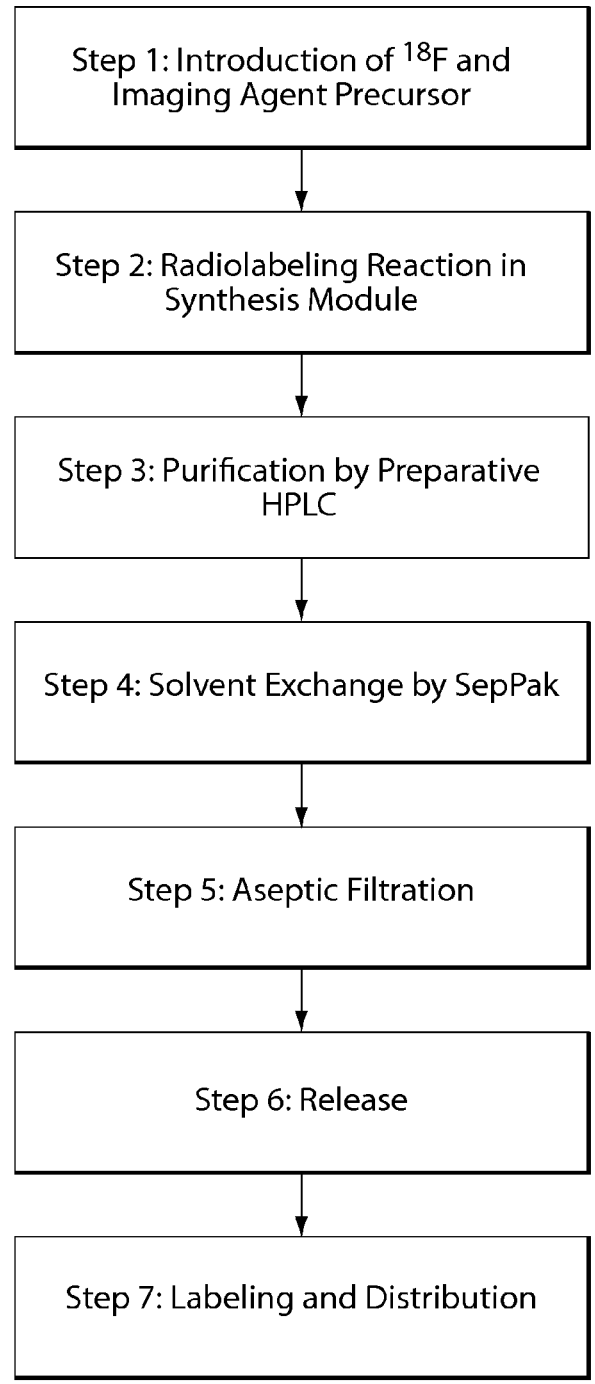
FIG. 2 shows a flow chart showing an exemplary method for synthesizing an imaging agent of the invention.

The automated reaction systems may carry-out numerous steps, as outlined in FIG. 2, including, but not limited to, providing an $^{18}F$ fluoride species, and an imaging agent precursor, optionally in a solution (e.g., as described herein, for example, imaging agent precursor-1 in acetonitrile), a radiolabeling reaction (e.g., reaction of the $^{18}F$ species and the imaging agent precursor to form the imaging agent) optionally in a synthesis module, purification (e.g., by preparative HPLC), solvent exchange (e.g., by SepPak), aseptic filtration, and release into a container.

Figure 3:
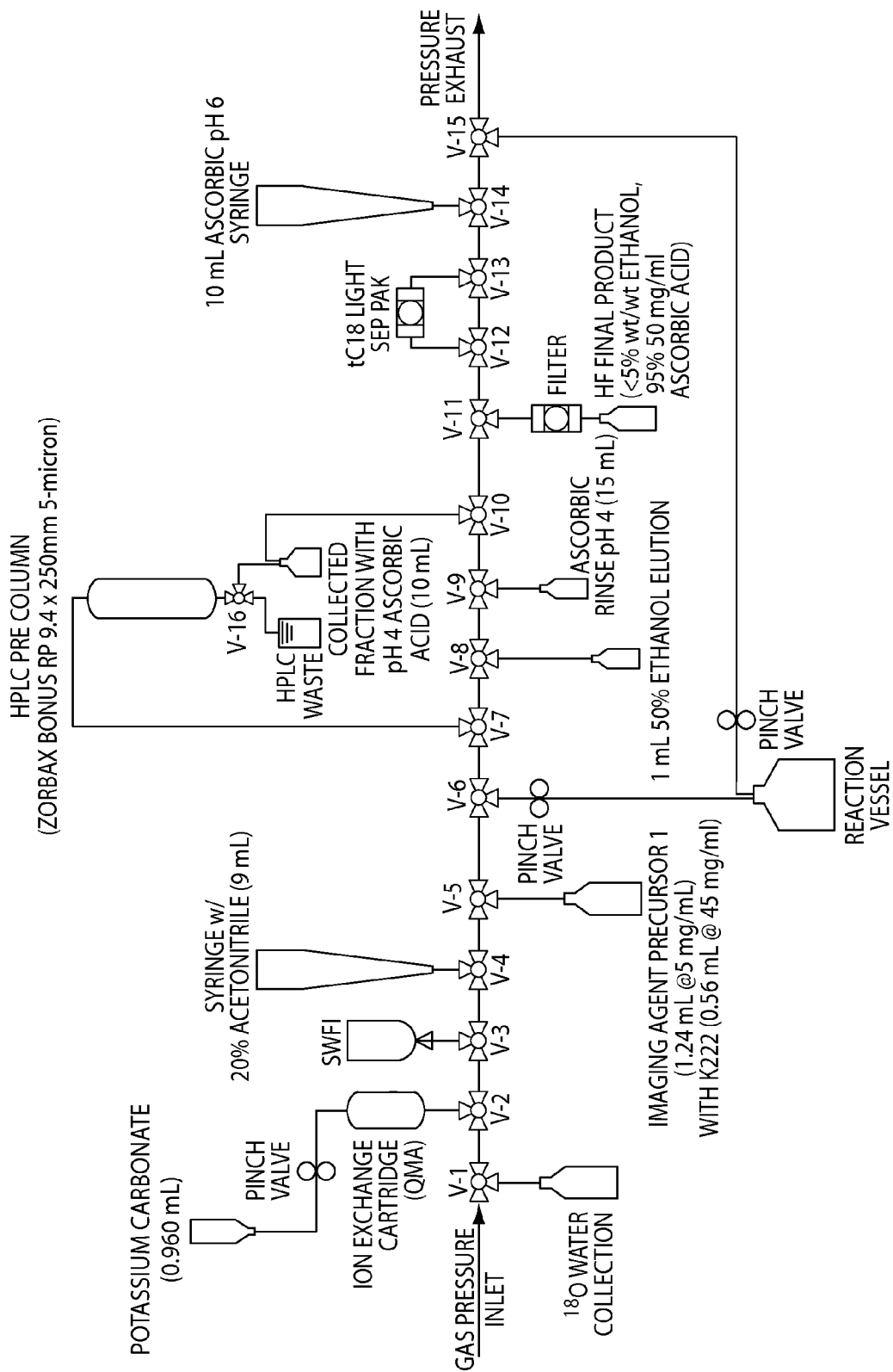
FIGS. 3 and 4 are schematic representations of exemplary cassettes with associated columns and reagents for synthesizing an imaging agent of the invention using a modified GE TRACERLab-MX chemistry module.
Figure 4:
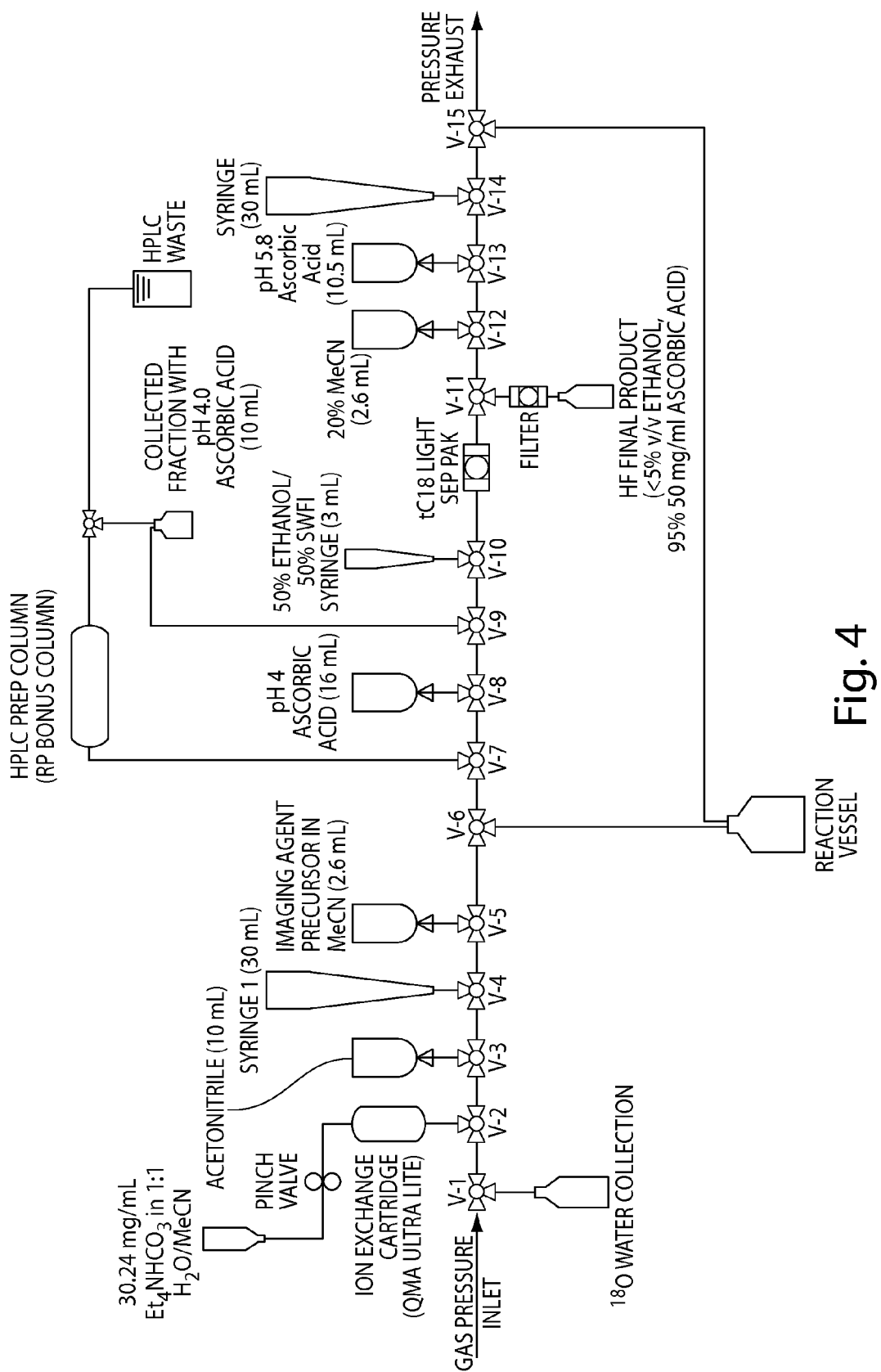
Figure 5:
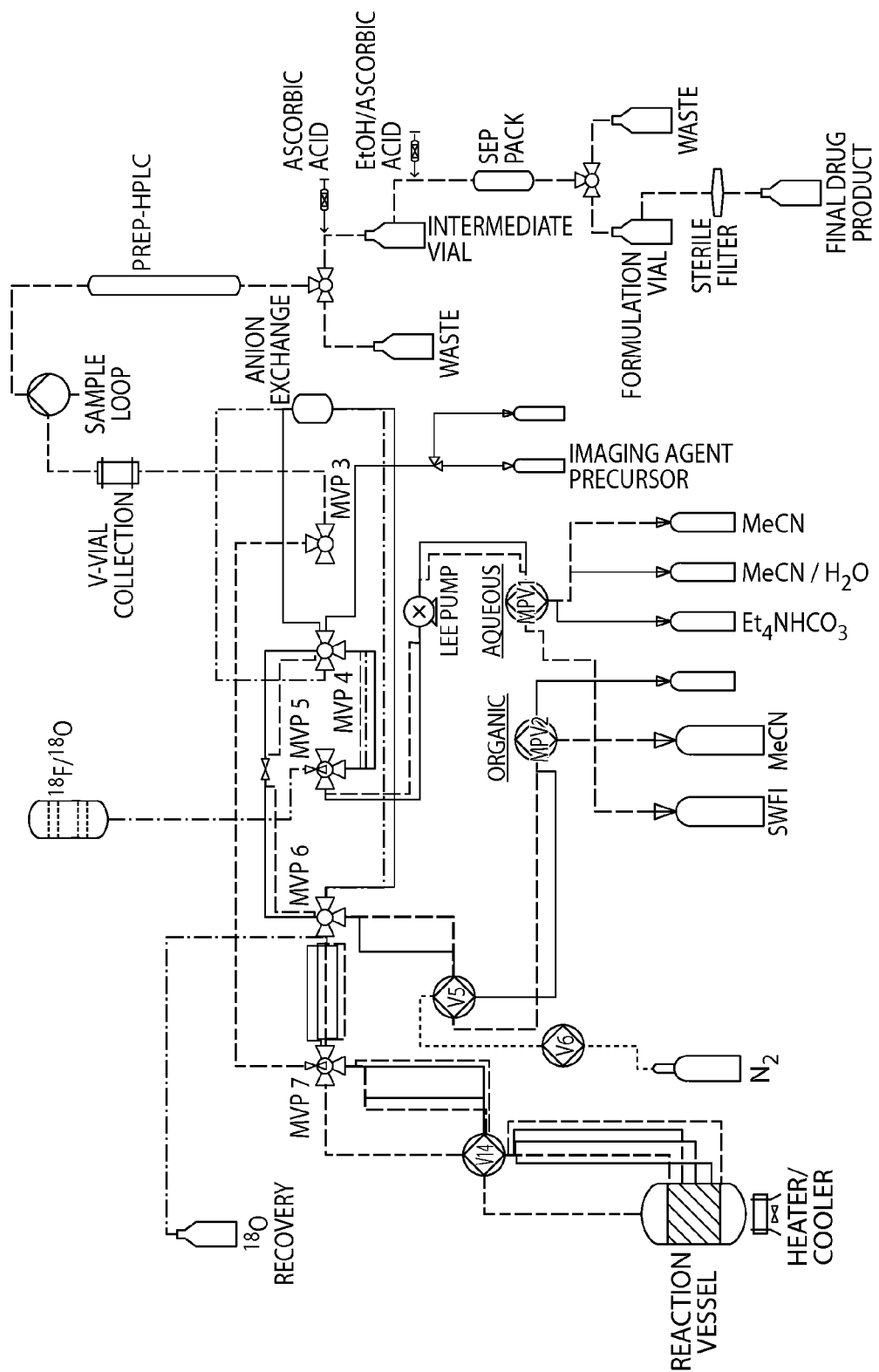
FIG. 5 is a schematic representation of a system for synthesizing an imaging agent of the invention using a modified Explora GN chemistry module.

In some embodiments, the automated reaction system may make use of a cassette comprising a reaction module in fluid connection with a purification module and/or a formulation module. FIGS. 3 and 4 show schematic representations of cassettes in connection with exemplary reaction systems for synthesizing an imaging agent comprising a reaction module, a purification module, and/or a formulation module. FIG. 5 shows schematic representation of an exemplary reaction system for synthesizing an imaging agent comprising a reaction module. For example, the reaction module may include a reaction chamber in which conversion of the imaging agent precursor to the imaging agent is performed. The reaction module may include a source of a fluoride species (e.g., $^{18}F$), a source of the imaging agent precursor, a source of a reagent (e.g., salt), and other sources of additional components such as solvents, each of which may optionally be fluidly connected to the reaction chamber. The reaction module may also comprise an anion exchange column for purification of the fluoride species, prior to introduction into the reaction chamber.

Upon reaction, the resulting imaging agent product is transferred from the reaction module to the purification module for further processing, treatment, and/or purification. The purification module may include, for example, a column (e.g., an HPLC column) fluidly connected to one or more sources of solvents to be used as eluents. The purification module may further comprise a source of a stabilizing agent (e.g., ascorbic acid or a salt thereof), which may be added to the imaging agent upon purification (e.g., by HPLC). The purified imaging agent is then transferred to the formulation module, where further purification and formulation may be performed. The formulation module may include a C-18 column for solvent exchange and/or a filter for aseptic filtration.

In another embodiment, a cassette comprises a reaction module and a formulation module. A reaction module of the invention may include a source of $^{18}F$, an anion exchange to remove unreacted $[^{18}O]_2O$, a source of an ammonium salt, a source for a diluent for the $^{18}F$, a source for an imaging agent precursor, (e.g., imaging agent precursor-1 shown in FIG. 1, or other imaging agent precursor), a source for an MeCN/$H_2O$ diluent for the reaction mixture, a reaction vessel for reacting the $^{18}F$ and the imaging agent precursor, a solid phase extraction column (e.g., a C18 column, or other suitable column) in fluid communication with the reaction vessel. The anion exchange column includes a solid sorbent to adsorb the $^{18}F$. Unreacted $[^{18}O]H_2O$ and residual reaction impurities pass through cationic resin matrix without adsorbing on the sorbent. The reaction module also includes a source of wash solutions in fluid communication with the anion exchange column for providing wash solutions to elute $^{18}$F off the sorbent, and includes a source of an eluent (e.g., as $H_2O$/MeCN, or other suitable eluent comprising a salt) in fluid communication with the anion exchange column for eluting the imaging agent product off the sorbent. The reaction module may also include a source of a diluent for the eluted $^{18}$F.

A formulation module of an apparatus of the invention may be in fluid communication with a reaction module and may include a solid phase extraction cartridge that includes a solid sorbent (e.g., C-18, or other suitable sorbent) to adsorb the diluted imaging agent, a source of wash solutions (e.g., comprising ascorbic acid, a salt thereof, or other suitable wash solution) in fluid communication with the solid phase extraction cartridge for providing wash solutions to wash off any remaining impurities on the sorbent, and a source of eluting fluid (e.g., ethanol/$H_2O$, or other suitable eluting fluid) in fluid communication with the solid phase extraction cartridge for eluting the imaging agent product off the sorbent. The formulation module may also include a source of a diluent (e.g., comprising ascorbic acid, a salt thereof, or other suitable diluent), for diluting the eluted imaging agent. The formulation module may also be in fluid communication with a sterilizing filter (e.g., a Millipore Millex GV PVDF sterilizing filter, or other suitable sterilizing filter).

In some embodiments, a general procedure for synthesizing an imaging agent of the invention (e.g., imaging agent-1) using an automated synthesis module is as follows. An [$^{18}$F]-fluoride species (e.g., in an aqueous solution) is provided to a synthesis module. In some cases, the fluoride species (e.g., in an aqueous solution) is filtered through an anion exchange column to remove unreacted [$^{18}$O]$H_2O$, wherein the [$^{18}$F]-fluoride species is retained within the cationic resin matrix. The column is washed with solution (e.g., an aqueous base) to elute the [$^{18}$F]-fluoride species into a reaction vessel. The resulting solution is diluted (e.g., with MeCN), and then concentrated to dryness (e.g., using elevated temperature and reduced pressure). The resulting material is exposed to solution of an imaging agent precursor (e.g., imaging agent precursor-1), optionally in the presence on one or more reagents (e.g., an activating agent). The solution is optionally heated for period of time (e.g., to 90-110° C. and maintained 5-15 min), followed by cooling. The solution is evaporated to dryness (e.g., using elevated temperature and/or reduced pressure), and then reconstituted in a reconstitution solution (e.g., $H_2O$/MeCN), followed by purification (e.g., by HPLC on an Agilent BONUS-RP column) using a select eluent (e.g., a solution of $NH_4HCO_2$ in $H_2O$/MeCN). The product is collected, optionally diluted (e.g., with ascorbic acid solution), followed by transfer to a formulation module.

In a particular embodiment, a cassette is provided for use with an automated synthesis module, for example, a GE TRACERlab MX synthesis module. In one embodiment, a cassette comprises a disposable sterilized assembly of molded stopcock manifolds specifically designed for use with the automated synthesis module (e.g., GE TRACERlab MX synthesis module). Individual manifolds are connected in a linear or non-linear fashion to form a directional array that dictates the flow path of reagents used in the preparation of an imaging agent (e.g., imaging agent-1). In some embodiments, the main body of the cassette contains at least one manifold comprising a plurality of manifold positions (e.g., stopcocks). For example, the main body may comprise at least one, two, three, four or more, manifolds. The cassette may comprise between 1 to 20 manifold positions, between 1 to 15 manifold positions, between 5 and 20 manifold positions, between 5 and 15 manifold positions. Each of the manifolds may or may not be symmetrical. In one embodiment, the main body of the cassette contains three plastic manifolds each fitted with five standard molded stopcocks, thereby having a total of 15 total manifold positions. Individual stopcocks are adapted with luer fittings to accommodate solvents, reagents, syringes, tubing required for gas and liquid handling, etc. The stopcocks are adapted for solvents and reagents and may be fitted with plastic spikes upon which inverted punch vials are located, while those featuring tubing and syringes are fitted with male luer connections according to function. In some embodiments, the cassette comprises a linear arrangement of a plurality of stopcock manifolds connected one or more of the components selected from the group consisting of a gas inlet, anion exchange cartridge, C-18 cartridge, syringe, solvent reservoir, reaction vessel, HPLC system, collection vessel, reservoir for solution of ascorbic acid or salt thereof, and exhaust outlet. In some cases the cassette further comprises tubing. In some cases, the cassette further comprises an imaging agent synthesis module, wherein the apparatus is fluidically connected to the cassette. In some cases, the apparatus is capable carrying out the method of synthesizing an imaging agent as described herein (e.g., a method of synthesizing imaging agent-1).

A non-limiting example of a cassette configuration which may be used for the preparation of imaging agent-1 is depicted in FIG. 3. The following provides a description of the attachments to each of the 15 manifold positions: 1) luer connections—gas inlet and [$^{18}$O]$H_2O$ recovery; 2) anion exchange cartridge—QMA Light; 3) spike connection—SWFI; 4) syringe—containing $H_2O$ and/or MeCN; 5) luer connection—imaging agent precursor-1; 6) luer connection—reaction vessel; 7) HPLC inlet; 8) luer connection—ethanol; 9) luer connection—ascorbic acid; 10) luer connection—collection vessel; 11) luer connection—final product vial; 12) luer connection—tC18 light Sep Pak column inlet; 13) luer connection—tC18 light Sep Pak column outlet; 14) syringe—containing ascorbic acid; 15) luer connections—reaction vessel and exhaust. Manifold one (stopcocks 1-5) is joined to manifold two (stopcocks 6-10) and manifold two is connected to manifold three (stopcocks 11-15) using two male luer connections fitted with a short length of silicon tubing. Individual manifold connections, luer fittings and all silicon tubing are readily available from commercial suppliers.

Another non-limiting example of a cassette configuration which may be used for the preparation of imaging agent-1 is depicted in FIG. 4. The following provides a description of the attachments to each of the 15 manifold positions: 1) luer connections—gas inlet and [$^{18}$O]$H_2O$ recovery; 2) anion exchange cartridge—QMA Light; 3) spike connection—MeCN; 4) syringe—empty; 5) spike connection—imaging agent precursor-1 (e.g., in MeCN); 6) luer connection—reaction vessel; 7) HPLC inlet; 8) spike connection—ascorbic acid; 9) luer connection—collection vessel; 10) syringe—containing ethanol and/or SFWI; 11) luer connection—final product vial; 12) spike connection—$H_2O$ and/or MeCN; 13) spike connection—ascorbic acid; 14)—syringe—empty; 15) luer connections—reaction vessel and exhaust. Manifold one (stopcocks 1-5) is joined to manifold two (stopcocks 6-10) using two male luer connections fitted with a short length of silicon tubing. Manifold two is connected to manifold three (stopcocks 11-15) using a tC-18 Sep-Pak® and the appropriate luer adapters. Individual manifold connections, luer fittings and all silicon tubing are readily available from commercial suppliers.

In some embodiments, the present invention provides a cassette for the preparation of an imaging agent comprising the formula:

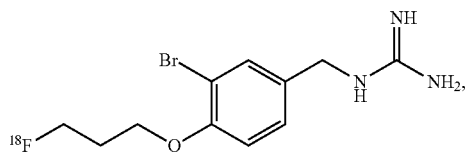 [SMILES: N=C(N)NCc1ccc(OCCC[18F])c(Br)c1]

or a salt, free base, and/or pharmaceutically acceptable formula, or combination thereof.

Pharmaceutical Compositions

Once a compound of the present disclosure (e.g., a compound of formula (I), (V), (VI), (VII), (IX) or (X))) has been prepared or obtained, it may be combined with one or more pharmaceutically acceptable excipients to form a pharmaceutical composition that is suitable for administration to a subject, including a human. As would be appreciated by one of skill in this art, the excipients may be chosen, for example, based on the route of administration as described below, the imaging agent being delivered, time course of delivery of the agent, and/or the health/condition of the subject. The pharmaceutical composition may be a solid or liquid.

Pharmaceutical compositions of the present invention and for use in accordance with the present invention may include a pharmaceutically acceptable excipient or carrier. As used herein, the term "pharmaceutically acceptable excipient" or "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium iodide, sodium metabisulfite, sodium nitrite, sodium sulfite, and sodium thiosulfate.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The pharmaceutical compositions of this invention can be administered to humans and/or to animals parenterally (e.g., by intravenous, intramuscular, subcutaneous, or intraperitoneal injection). The mode of administration will vary depending on the intended use, as is well known in the art.

Kits

Systems, methods, kits, and/or cassettes are provided comprising an imaging agent or an imaging agent precursor as described herein or a composition thereof and/or for preparation of an imaging agent (e.g., imaging agent-1). In some embodiments, kits for the administration of an imaging agent (e.g., imaging agent-1) are provided. In some cases, the composition provided with the kit may be used for or in the preparation of an imaging agent for detecting, imaging, and/or monitoring a disorder or condition. Kits of the invention may include, for example, a container comprising an imaging agent or an imaging agent precursor and instructions for use. Kits may comprise a sterile, non-pyrogenic, formulation comprising a predetermined amount of an imaging agent or an imaging agent precursor, and optionally other components. A container that may be used in conjunction with an imaging agent (e.g., imaging agent-1) for example, to deliver and/or administer the imaging agent to a subject, may be a syringe, bottle, vial, or tube. Instructions in a kit of the invention may relate to methods for synthesizing an imaging agent or an imaging agent precursor, methods of diluting the imaging agent or the imaging agent precursor, methods of administering the imaging agent to a subject for diagnostic imaging, or other instructions for use. An imaging agent or an imaging agent precursor may be provided in a kit and additional preparations before use may optionally include diluting the imaging agent or imaging agent precursor to a usable concentration.

In some cases, a kit can also include one or more vials containing a diluent for preparing an imaging agent (e.g., imaging agent-1) composition for administration to a subject (e.g., a human). A diluent vial may contain a diluent such as physiological saline or water. for diluting imaging agent-1. For example imaging agent-1 may be packaged in a kit in a ready-to-inject formulation, or may require some reconstitution or dilution whereby a final composition/formulation for injection or infusion is prepared.

Instructions in a kit of the invention may also include instructions for administering the imaging agent to a subject and may include information on dosing, timing, stress induction, etc. For example, a kit may include an imaging agent or imaging agent precursor as described herein along with instructions describing the intended application and the proper administration of the agent to a subject. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD), internet, and/or web-based communications. The written instructions may be in a form prescribed by a governmental agency regulating the manufacture, use or sale of pharmaceuticals products, which instructions can also reflect approval by the agency of manufacture, use; or sale for human administration. In some cases, the instructions can include instructions for mixing a particular amount of the diluent with a particular amount of a concentrated solution of the imaging agent or a solid preparation of the imaging agent, whereby a final formulation for injection or infusion is prepared for example, such that the resulting solution is at a suitable concentration for administration to a subject (e.g., at a concentration as described herein). A kit may include a whole treatment regimen of the inventive compound.

The kit may contain any one or more of the components described herein in one or more containers. As an example, in one embodiment, the kit may include instructions for mixing one or more components of the kit and/or isolating and mixing a sample and applying to a subject. The kit may include a container housing an agent described herein (e.g., an imaging agent precursor or an imaging agent). The agent may be in the form of a liquid, gel, or solid (e.g., powder). The agent may be prepared sterilely, packaged in a syringe, and shipped refrigerated. Alternatively it may be housed in a vial or other container for storage. A second container may have other agents prepared sterilely. Alternatively, the kit may include an agent premixed and shipped in a syringe, vial, tube, or other container. The kit may have one or more or all of the components required to administer the agents to a subject, such as a syringe or i.v. needle tubing and bag.

It also will be understood that containers containing the components of a kit of the invention, whether the container is a bottle, a vial (e.g., with a septum), an ampoule, an infusion bag, or the like, can include additional indicia such as conventional markings that change color when the preparation has been autoclaved or otherwise sterilized. A kit of the invention may further include other components, such as syringes, labels, vials, tubing, catheters, needles, ports, and the like. In some aspect of the invention, a kit may include a single syringe containing the imaging agent of the invention (e.g., imaging agent-1) sufficient for administration and in some aspects of the invention a kit may include more than one syringe.

Buffers useful in the preparation of imaging agents and kits include, for example, phosphate, citrate, sulfosalicylate, and acetate buffers. A more complete list can be found in the United States Pharmacopoeia. Lyophilization aids useful in the preparation of imaging agents and kits include, for example, mannitol, lactose, sorbitol, dextran, FICOLL® polymer, and polyvinylpyrrolidine (PVP). Stabilization aids useful in the preparation of imaging agents and kits include, for example, ascorbic acid, cysteine, monothioglycerol, sodium bisulfite, sodium metabisulfite, gentisic acid, and inositol. Solubilization aids useful in the preparation of imaging agents and kits include, for example, ethanol, glycerin, polyethylene glycol, propylene glycol, polyoxyethylene sorbitan monooleate, sorbitan monoloeate, polysorbates, poly (oxyethylene)-poly(oxypropylene)-poly(oxyethylene) block copolymers (e.g., Pluronics®) and lecithin. In certain embodiments, the solubilizing aids are polyethylene glycol, cyclodextrins, and Pluronics. Bacteriostats useful in the preparation of imaging agents and kits include, for example, benzyl alcohol, benzalkonium chloride, chlorbutanol, and methyl, propyl, or butyl paraben.

DEFINITIONS

For convenience, certain terms employed in the specification, examples, and appended claims are listed here.

Definitions of specific functional groups and chemical terms are described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in "Organic Chemistry," Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclochexyl.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2 R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, poly(ethylene glycol), and alkyl-substituted amino The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CHF_2$; —$CH_2F$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substitutents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl) aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "heterocycle" is given its ordinary meaning in the art and refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms.

The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino," as used herein, refers to a primary (—NH$_2$), secondary (—NHR$_x$), tertiary (—NR$_x$R$_y$), or quaternary (—N$^+$R$_x$R$_y$R$_z$)amine, where R$_x$, R$_y$, and R$_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, methylethylamino, iso-propylamino, piperidino, trimethylamino, and propylamino.

The term "alkyne" is given its ordinary meaning in the art and refers to branched or unbranched unsaturated hydrocarbon groups containing at least one triple bond. Non-limiting examples of alkynes include acetylene, propyne, 1-butyne, 2-butyne, and the like. The alkyne group may be substituted and/or have one or more hydrogen atoms replaced with a functional group, such as a hydroxyl, halogen, alkoxy, and/or aryl group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, t-butoxy, neopentoxy and n-hexoxy. Examples of thioalkyl include, but are not limited to, methylthio, ethylthio, propylthio, isopropylthio, n-butylthio, and the like.

The term "aryloxy" refers to the group, —O-aryl. The term "acyloxy" refers to the group, —O-acyl.

The term "alkoxyalkyl" refers to an alkyl group substituted with at least one alkoxy group (e.g., one, two, three, or more, alkoxy groups). For example, an alkoxyalkyl group may be —($C_{1-6}$-alkyl)-O—($C_{1-6}$-alkyl), optionally substituted. In some cases, the alkoxyalkyl group may be optionally substituted with another alkyoxyalkyl group (e.g., —($C_{1-6}$-alkyl)-O—($C_{1-6}$-alkyl)-O—($C_{1-6}$-alkyl), optionally substituted.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful for the formation of an imaging agent or an imaging agent precursor. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

As used herein, the term "determining" generally refers to the analysis of a species or signal, for example, quantitatively or qualitatively, and/or the detection of the presence or absence of the species or signals.

The term "diagnostic imaging," as used herein, refers to a procedure used to detect an imaging agent.

The term "diagnosis" as used herein encompasses identification, confirmation, and/or characterization of a condition, a disease, and/or a disorder.

A "diagnostic kit" or "kit" comprises a collection of components, termed the formulation, in one or more vials which are used by the practicing end user in a clinical or pharmacy setting to synthesize diagnostic radiopharmaceuticals. For example, the kit may be used by the practicing end user in a clinical or pharmacy setting to synthesize and/or use diagnostic radiopharmaceuticals. In some embodiments, the kit may provide all the requisite components to synthesize and use the diagnostic pharmaceutical except those that are commonly available to the practicing end user, such as water or saline for injection and/or the radioisotope (e.g., $^{18}F$). equipment for processing the kit during the synthesis and manipulation of the radiopharmaceutical, if required, equipment necessary for administering the radiopharmaceutical to the subject such as syringes, shielding, imaging equipment, and the like. In some embodiments, imaging agents may be provided to the end user in their final form in a formulation contained typically in one vial or syringe, as either a lyophilized solid or an aqueous solution.

As used herein, a "portion of a subject" refers to a particular region of a subject, location of the subject. For example, a portion of a subject may be the brain, heart, vasculature, cardiac vessels, etc., of a subject.

As used herein a "session" of testing may be a single testing protocol that a subject undergoes.

As used herein, the term "subject" refers to a human or non-human mammal or animal. Non-human mammals include livestock animals, companion animals, laboratory animals, and non-human primates. Non-human subjects also specifically include, without limitation, horses, cows, pigs, goats, dogs, cats, mice, rats, guinea pigs, gerbils, hamsters, mink, and rabbits. In some embodiments of the invention, a subject is referred to as a "patient." In some embodiments, a patient or subject may be under the care of a physician or other health care worker, including, but not limited to, someone who has consulted with, received advice from or received a prescription or other recommendation from a physician or other health care worker.

Any of the compounds described herein may be in a variety of forms, such as, but not limited to, salts, solvates, hydrates, tautomers, and isomers.

In certain embodiments, the imaging agent is a pharmaceutically acceptable salt of the imaging agent. The term "pharmaceutically acceptable salt" as used herein refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, loweralkyl sulfonate and aryl sulfonate.

In certain embodiments, the compound is in the form of a hydrate or solvate. The term "hydrate" as used herein refers to a compound non-covalently associated with one or more molecules of water. Likewise, the term "solvate" refers to a compound non-covalently associated with one or more molecules of an organic solvent.

In certain embodiments, the compound described herein may exist in various tautomeric forms. The term "tautomer" as used herein includes two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

In certain embodiments, the compounds described herein may exist in various isomeric forms. The term "isomer" as used herein includes any and all geometric isomers and stereoisomers (e.g., enantiomers, diastereomers, etc.). For example, "isomer" includes cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

These and other aspects of the present invention will be further appreciated upon consideration of the following Examples, which are intended to illustrate certain particular embodiments of the invention but are not intended to limit its scope, as defined by the claims.

EXAMPLES

Example 1

Synthesis of 3-(4-((1,2-Bis(tert-butoxycarbonyl) guanidino)methyl)-2-bromophenoxy)propyl 4-methylbenzenesulfonate

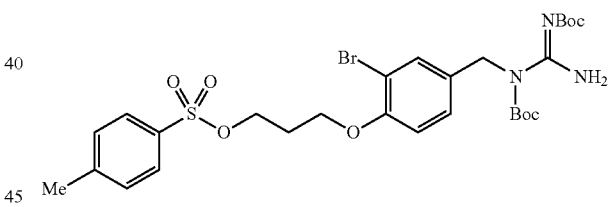

Example 1A

Synthesis of 1,2-bis(tert-butoxycarbonyl)-1-[3-bromo-4-(3-hydroxypropoxy)benzyl]-guanidine

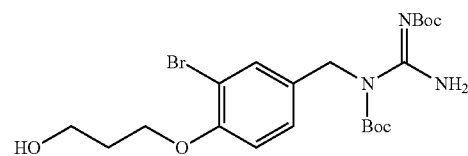

To a solution of 1,2-bis(tert-butoxycarbonyl)-1-[3-bromo-4-hydroxybenzyl]-guanidine (for synthesis, see, for example, Purohit et al., International PCT Patent Publication No. WO2008/083056, incorporated herein by reference) (2.0 g, 4.51 mmol) dissolved in anhydrous DMF (45 mL) was added $K_2CO_3$ (1.12 g, 8.13 mmol), and 3-bromopropanol (816 mg, 5.87 mmol) and the reaction mixture warmed to 50° C. using an oil bath. After 2 h, the reaction mixture was diluted with water (30 mL), and the aqueous layer separated then extracted with EtOAc (3×100 mL). The combined organic layers were dried over MgSO$_4$, filtered and concentrated to a solid. The crude material was purified using silica gel chromatography (4:1 to 3:2 hexanes:EtOAc) to yield a white solid product (2.00 g, 88% yield). $^1$H NMR (CDCl$_3$, 600 MHz): δ 9.42 (brs, 1H), 9.27 (brs, 1H), 7.54 (d, J=1.8 Hz, 1H), 7.26 (m, 1H), 6.85 (d, J=2.4 Hz, 1H), 5.08 (brs, 2H), 4.19 (t, J=5.4 Hz, 2H), 3.92 (m, 2H), 2.16 (m, 1H), 2.18 (m, 2H), 1.51 (s, 9H), 1.43 (s, 9H); $^{13}$C NMR (CDCl$_3$, 150 MHz): δ 163.8, 160.8, 155.0, 154.3, 144.8, 133.1, 132.6, 127.9, 113.0, 111.7, 84.7, 79.2, 67.8, 60.6, 46.7, 31.9, 28.5, 28.3.

Example 1B

Synthesis of 3-(4-((1,2-bis(tert-butoxycarbonyl) guanidino)methyl)-2-bromophenoxy)propyl 4-methylbenzenesulfonate

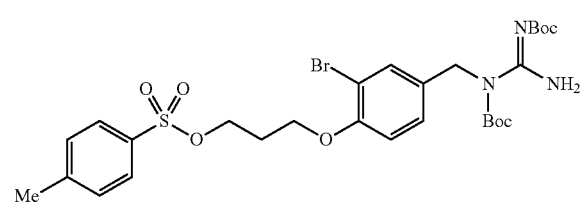

To a solution of the product of Example 1A (339 mg, 0.676 mmol) dissolved in anhydrous CH$_2$Cl$_2$ (6.76 mL) was added TsCl (155 mg, 0.812 mmol), DMAP (99 mg, 0.812 mmol) and Et$_3$N (0.141 mL, 1.01 mmol). The reaction mixture was stirred at room temperature for 1.5 h then concentrated to a yellow oil. The crude material was directly purified using silica gel chromatography (4:1 hexanes:EtOAc) to yield a colorless oil (384.3 mg, 87% yield). $^1$H NMR (CDCl$_3$, 600 MHz): δ 7.74 (d, J=8.4 Hz, 2H), 7.50 (d, J=1.8 Hz, 1H), 7.21 (m, 3H), 6.70 (d, J=8.4 Hz, 1H), 5.08 (brs, 2H), 4.30 (t, J=6.0 Hz, 2H), 4.00 (t, J=6.0 Hz, 2H), 2.37 (s, 3H), 2.16 (m, 2H), 1.51 (s, 9H), 1.43 (s, 9H); $^{13}$C NMR (CDCl$_3$, 150 MHz): δ 160.6, 154.9, 154.0, 145.0, 133.0, 132.9, 132.7, 130.0, 128.0, 112.9, 111.9, 84.7, 79.0, 67.0, 64.1, 46.4, 29.0, 28.5, 28.2, 21.8.

Example 2

Synthesis of 3-(4-((1,2-Bis(tert-butoxycarbonyl) guanidino)methyl)-2-bromophenoxy)propyl 4-bromobenzenesulfonate

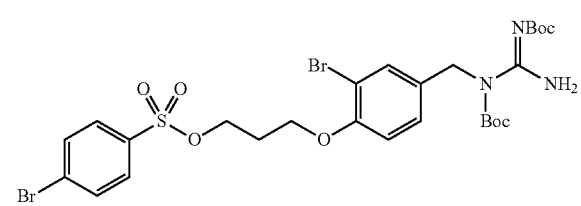

To a solution of the product of Example 1A (300 mg, 0.598 mmol) dissolved in anhydrous CH$_2$Cl$_2$ (6.0 mL) was added BsCl (183.3 mg, 0.718 mmol), DMAP (87.7 mg, 0.718 mmol) and Et$_3$N (0.125 mL, 0.897 mmol). The reaction mixture was stirred at room temperature for 2.5 h then concentrated to an oil. The crude material was directly purified using silica gel chromatography (4:1 hexanes:EtOAc) to yield a colorless oil (395.6 mg, 92% yield). $^1$H NMR (CDCl$_3$, 300 MHz): δ 9.40 (brs, 2H), 7.72-7.67 (m, 2H), 7.55-7.50 (m, 3H), 7.24 (dd, J=3, 9 Hz, 1H), 6.69 (d, J=9 Hz, 1H), 5.11 (brs, 2H), 4.35 (t, J=6.0 Hz, 2H), 3.97 (t, J=6.0 Hz, 2H), 2.18 (m, 2H), 1.47 (s, 9H), 1.39 (s, 9H); $^{13}$C NMR (4:1, CDCl$_3$: DMSO-d$_6$, 150 MHz): δ 160.7, 160.5, 157.1, 153.5, 134.0, 132.0, 131.6, 130.3, 130.2, 128.6, 128.3, 127.2, 127.2, 112.4, 111.3, 84.5, 79.0, 66.8, 63.4, 42.3, 27.4.

Example 3

Synthesis of 3-(4-((1,2-Bis(tert-butoxycarbonyl) guanidino)methyl)-2-bromophenoxy)propyl methanesulfonate

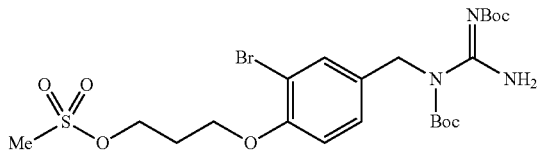

To a solution of the product of Example 1A (300 mg, 0.598 mmol) dissolved in anhydrous CH$_2$Cl$_2$ (6.0 mL) was added MsCl (55.8 μL, 0.718 mmol), DMAP (87.7 mg, 0.718 mmol) and Et$_3$N (0.125 mL, 0.897 mmol). The reaction mixture was stirred at room temperature for 45 min then concentrated to yield an oil. The crude material was directly purified using silica gel chromatography (4:1 hexanes:EtOAc) to yield a colorless oil (245.6 mg, 71% yield). $^1$H NMR (CDCl$_3$, 300 MHz): δ 9.35 (brs, 2H), 7.56 (d, J=3.0 Hz, 1H), 7.26 (m, 1H). 6.84 (d, J=9.0 Hz, 1H), 5.09 (brs, 2H), 4.53 (t, J=6.0 Hz, 2H), 4.15 (t, J=6.0 Hz, 2H), 3.01 (s, 3H), 2.29 (m, 2H), 1.52 (s, 9H), 1.43 (s, 9H); $^{13}$C(CDCl$_3$, 150 MHz): δ 160.7, 154.9, 154.1, 133.3, 133.1, 128.0, 132.2, 113.2, 110.7, 128.3, 84.7, 80.5, 66.9, 64.6, 46.7, 29.9, 28.5, 28.2.

Example 4

Synthesis of 3-(4-((1,2-Bis(tert-butoxycarbonyl) guanidino)methyl)-2-bromophenoxy)propyl trifluoromethanesulfonate

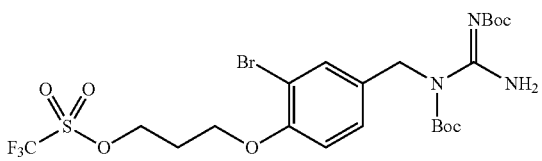

To a solution of the product of Example 1A (300 mg, 0.598 mmol) dissolved in anhydrous CH$_2$Cl$_2$ (6.0 mL) was added Tf$_2$O (203 mg, 0.718 mmol), DMAP (87.7 mg, 0.718 mmol) and Et$_3$N (0.125 mL, 0.897 mmol). The reaction mixture was stirred at room temperature for 1.5 h then concentrated to yield an oil. The crude material was directly purified using silica gel chromatography (4:1 to 1:1 hexanes:EtOAc) to yield a colorless oil (312 mg, 82% yield). $^1$H NMR (CDCl$_3$, 300 MHz): δ 9.39 (brs, 2H), 7.54 (d, J=3.0 Hz, 1H), 7.26 (m, 1H), 6.84 (d, J=9.0 Hz, 1H), 5.08 (brs, 2H), 4.16 (t, J=6.0 Hz, 2H), 3.81 (t, J=6.0 Hz, 2H), 2.27 (m, 2H), 1.50 (s, 9H), 1.39 (s, 9H); $^{13}$C NMR (CDCl$_3$, 150 MHz): δ 160.7, 154.9, 154.3, 133.2, 132.8, 128.1, 113.2, 112.0, 84.7, 79.3, 65.8, 46.7, 40.7, 32.4, 28.5, 28.2; $^{19}$F NMR (CDCl$_3$, 282 MHz): δ-75.5 (s).

Example 5

The following Example describes the synthesis of compounds of Formula (II), including but not limited to imaging agent precursor-1. The Example more specifically provides the synthesis of the trifluoroacetic acid salt of imaging agent precursor-1, according to the scheme shown in FIG. 6.

Example 5A

Synthesis of
3-bromo-4-(3-hydroxypropoxy)benzonitrile
(Compound 1)

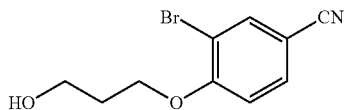 [SMILES: N#Cc1ccc(OCCCO)c(Br)c1]

3-Bromo-4-hydroxy benzonitrile (10.0 g, 50.5 mmol) was dissolved in acetone and successively treated with 1-bromo-3-propanol (19.0 g, 138 mmol) and K$_2$CO$_3$ (20.9 g, 151 mmol) at ambient temperature. The resulting suspension was warmed to 50° C. and maintained 3 d. After cooling to ambient temperature, the solids were removed by filtration, exhaustively was with acetone and the filtrate concentrated. Purification by chromatography on SiO$_2$ (A: hexanes; B: EtOAc; 0-100% B over 35.4 min; 200 mL/min; 330 g column) afforded a solid. Further purification by recrystallization from hot MTBE (131 mL) and pentane (130 mL), with cooling at −20° C. (12 h) to induce precipitation, afforded a solid (7.2 g, 58%). $^1$H NMR (300 MHz, CDCl$_3$) δ 7.78 (s, 1H), 7.56 (d, J=9 Hz, 1H), 6.94 (d, J=6 Hz, 1H), 4.23 (t, J=6 Hz, 2H), 3.88 (t, J=6 Hz, 2H), 2.08 (m, J=6 Hz, 2H).

Example 5A-1

The following Example describes the synthesis of Compound 1, using an alternate synthetic method to Example 5A. 3-Bromo-4-hydroxybenzonitrile (0.100 kg, 0.505 mol) was added to a reaction vessel followed by 2-butanone (1.00 L), 3-chloro-1-propanol (50 mL, 0.598 mol), Na$_2$CO$_3$ (80.6 g, 0.760 mol), and NaI (15.0 g, 0.100 mol). The reaction mixture was then shielded from light using aluminum foil, heated to reflux and stirred overnight. After 23 h, unreacted starting material remained. Additional 3-chloro-1-propanol (8.7 mL, 0.10 mol) was then added, and the mixture returned to reflux. After 34 h total reflux time, the heat was removed, and the vessel cooled slowly over 19 h to 22.8° C. before addition of MTBE (1.00 L). The resulting solution was stirred 44 min then filtered through a class C sintered glass funnel containing a 5 cm Celite bed. The reaction vessel and Celite bed were rinsed with several small portions of MTBE, and the combined filtrates concentrated in vacuo.

The crude solid was dissolved in refluxing MTBE (410 mL) then treated with heptane (410 mL) over 14 min to form an oil. Upon completion of the addition, the heating mantle was removed and the biphase cooled to 29.9° C. After 1 h, the resulting suspension was diluted with heptane (1.18 L), stirred 66 min then filtered through a class C sintered glass funnel. The solids were washed with 9:1 heptane:MTBE (398 mL) then transferred to a drying pan and placed in a vacuum oven. After drying at 35±5° C. for 36 h, 118.4 g of the solid was obtained (0.462 mol; 91.5%).

Example 5B

Synthesis of
3-bromo-4-(3-hydroxypropoxy)benzylamine
hydrochloride (Compound 2)

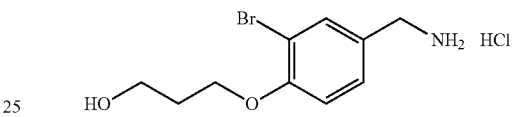

Compound 1 (5.0 g, 19.5 mmol) was suspended in THF then stirred at ambient temperature until complete dissolution was observed. BH$_3$.THF (42.9 mmol; 42.9 mL of a 1.0 M solution in THF) was then added dropwise and the resulting mixture heated to reflux. After 5 h, the mixture was cooled to 4° C. then carefully treated with MeOH (50 mL). HCl(g) was bubbled through the solution for 30 min then all volatiles removed in vacuo. The white solid thus obtained was dissolved in MeOH (17.8 mL) then successively treated with MTBE (36 mL) and hexanes (40 mL). The resulting suspension was stirred 30 min, the white solids collected then dried to constant weight (4.7 g, 81%). This material was used directly in the subsequent step without further purification.

Example 5B-1

The following Example describes the synthesis of Compound 2, using an alternate synthetic method to Example 5B. Compound 1 (118.4 g, 0.462 mol) was transferred, under nitrogen, to a reaction vessel along with anhydrous THF (1.16 L). The mixture was stirred until complete dissolution was observed then slowly treated with BH$_3$.THF (1.02 mol; 1.02 L of a 1.0 M solution in THF) over 20 min Following complete addition, the reaction vessel was heated to reflux and maintained overnight. The resulting suspension was then cooled to 29.9° C. before an ice water bath was applied to further reduce the internal temperature to 4.9° C. Hydrochloric acid (1.25 mol; 1.00 L of 1.25 M solution in MeOH) was then added dropwise over 94 min; a measured value of pH 3 confirmed complete hydrolysis of the intermediate boronate species. The resulting mixture was then concentrated to dryness in vacuo (<35° C.) to yield a solid (172.1 g).

The crude product was transferred to a new, clean reaction vessel along with MeOH (279 mL). After stirring 20 min, the resulting suspension was treated with MTBE (550 mL), stirred 16 min then diluted with heptane (1.10 L). After 2.5 h, the solids were isolated by filtration through a class C sintered glass funnel then washed with 1:1 heptane:MTBE (410 mL)

Example 5C

Synthesis of 1,3-bis(tert-butoxycarbonyl)-[3-bromo-4-(3-hydroxypropoxy)benzyl]-guanidine (Compound 3)

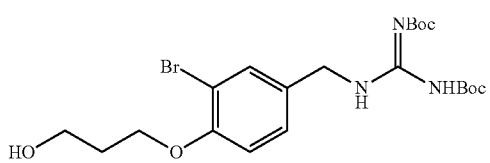

Compound 2 (0.438 g, 1.48 mmol) was dissolved in MeOH (7.00 mL), and successively treated with N,N'-bis-tert-butoxycarbonyl-1H-pyrazole carboxamidine (0.412 g, 1.33 mmol) and i-Pr₂NEt (0.380 g, 2.95 mmol) at ambient temperature. The resulting mixture was stirred 3 h then concentrated and purified by chromatography on SiO₂ (A: hexanes; B: EtOAc; 0-100% B over 19.2 min; 40 mL/min; 40 g column) to obtain the product as a white foam (0.61 g, 82%). ¹H NMR (300 MHz, CDCl₃) δ 8.5 (t, 1H), 7.5 (d, 1H), 7.2 (dd, 1H), 6.85 (d, 1H), 4.52 (d, 2H), 4.18 (t, 2H), 3.9 (t, 2H), 2.1 (m, 2H), 1.52 (s, 9H), 1.47 s (s, 9H).

Example 5C-1

The following Example describes the synthesis of Compound 3, using an alternate synthetic method to Example 5C. Compound 2 (119.1 g, 0.401 mol) was transferred to a reaction vessel with MeOH (1.13 L), N,N'-bis-tert-butoxycarbonyl-1H-pyrazole carboxamidine (126.4 g, 0.408 mol), and i-Pr₂NEt (82.0 ml, 0.461 mol). The resulting mixture was stirred at ambient temperature for 13 h then treated with EtOAc (150 mL) and concentrated to dryness in vacuo (305.7 g). The crude oil thus obtained was transferred to a separatory funnel using 1.31 L of EtOAc then washed with deionized water (417 mL). The aqueous layer was further washed with EtOAc (600 mL), and the combined organic layers successively washed with 307 mL 0.5 M NaHSO₄.H₂O, 300 mL deionized water and 300 mL 0.5 M NaHCO₃ then dried over excess Na₂SO₄. The drying agent was removed by filtration through a class C sintered glass funnel then washed with EtOAc (190 mL). The combined filtrates were concentrated in vacuo to yield a light brown, viscous oil (213 g).

Example 5D

Synthesis of 3-(4-((2,3-bis(tert-butoxycarbonyl)guanidino)methyl)-2-bromophenoxy)propyl 4-bromobenzenesulfonate (Compound 4)

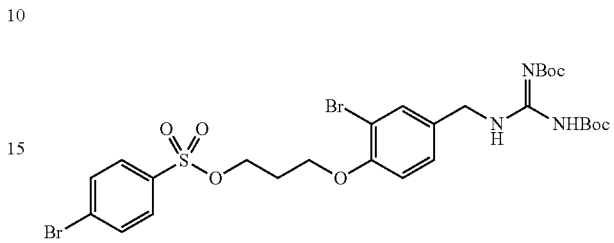

Compound 3 (0.2 g, 0.4 mmol) was successively treated with 4-bromobenzenesulfonyl chloride (173 mg, 0.677 mmol), Et₃N (80.62 mg, 0.796 mmol), DMAP (4.86 mg, 3.98 µmol and CH₂Cl₂ (8 mL) at ambient temperature. The resulting solution was stirred 24 h then all volatiles removed in vacuo. The residue was triturated with hexanes:EtOAc (10 mL; 9:1 v/v) to obtain a white solid which was collected by filtration. Purification by chromatography on SiO₂ (A: hexanes; B: EtOAc; 0-100% B over 15.4 min; 35 ml/min; 24 g column) afforded the product as a sticky white solid (174 mg, 60%). ¹H NMR (300 MHz, CDCl₃) δ 8.53 (t, 1H), 7.66 (m, 2H), 7.5 (m, 3H), 7.17 (m, 1H), 6.67 (d, J=8.4 Hz, 1H), 4.53 (d, J=5 Hz, 2H), 4.33 (t, J=6 Hz, 2H), 3.93 (t, J=6 Hz, 2H), 2.16 (m, 2H), 1.53 (s, 9H), 1.47 (s, 9H).

Example 5D-1

The following Example describes the synthesis of Compound 4, using an alternate synthetic method relative to Example 5D. Compound 3 (212.9 g, 0.424) was transferred to a reaction vessel, under nitrogen, using anhydrous CH₂Cl₂ (2.00 L) then stirred 15 min until complete dissolution occurred. The resulting solution was successively treated with 4-bromobenzenesulfonyl chloride (125.5 g, 0.491 mol), Et₃N (80.0 mL, 0.573 mol) and DMAP (2.06 g, 0.017 mol) then vigorously stirred 16 h at ambient temperature. NOTE: the process was relatively exothermic as the internal temperature reached 33.9° C. following addition of the DMAP. Additional 4-bromobenzenesulfonyl chloride (10.5 g, 0.041 mol) was then added and the resulting mixture stirred 19 h. This process was repeated once again using additional 4-bromobenzenesulfonyl chloride (20.9 g, 0.082 mol) and Et₃N (11.3 mL, 0.081 mol) followed by 8 h of vigorous stirring at ambient temperature. The resulting solution was then treated with deionized water (600 mL) with transfer to a separatory funnel. The layers were then separated and the aqueous layer was washed with CH₂Cl₂ (290 mL). The combined organic layers were further washed with 5% aqueous NaHCO₃ (380 mL), dried over an excess of Na₂SO₄, then filtered and concentrated in vacuo. The crude product was partially purified by silica gel chromatography (~20 g SiO₂/g of crude product) using 10-20% EtOAc/heptane; like fractions were combined and concentrated to a solid in vacuo. The crude material thus obtained was further purified through trituration from MTBE (804 mL) and heptane (1580 mL) then isolated by filtration through a class C sintered glass funnel. The filter cake was washed with 9:1 heptane/MTBE (467 mL) then transferred to a vacuum oven and dried 15 h at ambient temperature (149.4 g, 0.207 mol; 48.9%).

Example 5E

Synthesis of 3-(2-Bromo-4-(guanidinomethyl)phenoxy)propyl 4-bromobenzenesulfonate, trifluoroacetate salt (TFA salt of Imaging Agent Precursor-1)

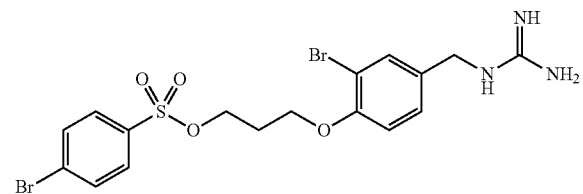

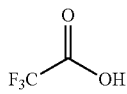

A 25 mL round bottom flask was charged with Compound 4 (3.00 g, 4.15 mmol) then CH$_2$Cl$_2$ (6 mL), and the resulting suspension stirred until complete dissolution was observed. Trifluoroacetic acid (6 mL, 78.3 mmol) was then added and the mixture stirred an additional 4 h. All volatiles were then removed, and the residue treated with EtOAc (20 mL). The resulting mixture was stirred at room temperature for 3 h, during which time a white solid precipitated. The solids were collected on a sintered glass funnel of medium porosity then exhaustively washed with EtOAc (20 mL) and dried to constant weight (2.5 g, 95%). $^1$H NMR (400 MHz, DMSO-d$_6$) δ 7.54 (m, 4H), 7.4 (d, 1H), 7.15 (m, 1H), 6.9 (d, 1H), 4.15 (m, 4H), 3.86 (m, 2H), 1.92 (m, 2H).

Example 5E-1

The following Example describes the synthesis of the TFA salt of imaging agent precursor-1, using an alternate synthetic method relative to Example 5E. Compound 4 (149.4 g, 0.207 mol) was dissolved in CH$_2$Cl$_2$ (1.20 L) then treated with TFA (300 mL) in one portion at ambient temperature. After 14 h, all volatiles were removed in vacuo and the crude oil directly treated with EtOAc (1.32 L). After 3 h, the resulting suspension was filtered through a class C sintered glass funnel and the solids washed with EtOAc (2×140 mL). The filter cake was then transferred to a glass drying pan and placed in a vacuum oven for 12 h at ambient temperature.

Example 6

Synthesis of 3-(2-Bromo-4-(guanidinomethyl)phenoxy)propyl 4-bromobenzenesulfonate, hydrochloric acid salt

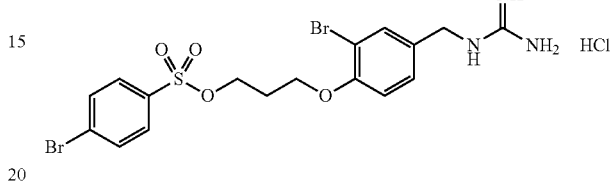

A 25 mL round bottom flask was charged with Compound 4 (2.00 g, 2.77 mmol) then HCl (28.0 mmol; 7.00 mL of a 4.0 M solution in dioxane), and the resulting solution stirred 4 h. The white solid thus obtained was collected, exhaustively washed with MTBE (20 mL) then dried to constant weight (1.4 g, 2.51 mmol; 90.6%). $^1$H NMR (400 MHz, D$_2$O+ DMSO-d$_6$) δ 6.94 (d, 2H), 6.76 (d, 2H), 6.74 (s, 1H), 6.45 (m, 1H), 6.17 (d, 1H), 3.53 (m, 4H), 3.15 (t, 2H), 1.36 (m, 2H), 0.5 (s, 1H).

Example 7

Synthesis of 3-(2-Bromo-4-(guanidinomethyl)phenoxy)propyl 4-bromobenzenesulfonate, p-toluenesulfonic acid salt

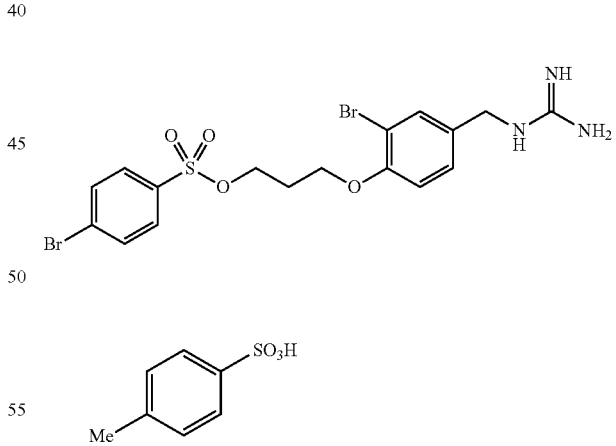

A 25 mL round bottom flask was charged with Compound 4 (0.50 g, 0.69 mmol), p-toluenesulfonic acid hydrate (1.32 g, 6.93 mmol) and THF (6 mL). The resulting solution was heated to reflux under a nitrogen atmosphere, maintained 6 h then slowly cooled to ambient temperature overnight. The white solid precipitate thus obtained was collected, exhaustively washed with Et$_2$O and dried to a constant weight (0.328 g, 0.473 mmol; 68.3%). $^1$H NMR (300 MHz, DMSO-d$_6$) δ 7.74 (m, 5H), 7.48 (d, 1H), 7.45 (m, 2H), 7.23 (dd, J=3 Hz, 1H), 7.08 (m, 3H), 6.99 (d, J=9 Hz, 1H), 4.25 (m, J=6 Hz, 3H), 3.97 (t, J=6 Hz, 2H), 2.26 (s, 3H), 2.04 (m, 2H).

Example 8

Synthesis of 3-(2-Bromo-4-(guanidinomethyl)phenoxy)propyl 4-bromobenzenesulfonate, acetic acid salt

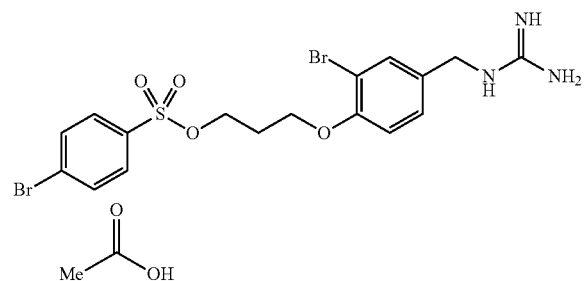

The product of Example 6 (200 mg, 0.359 mmol) was dissolved in THF/H$_2$O (2 mL; 1:1 v/v) then treated with AgOAc (3 mL of a 22 mg/mL solution in 1:4 MeCN/H$_2$O); immediate precipitation was observed. The slurry was stirred 20 min then filtered through a 0.45 μm PVDF filter disc, and the filtrate lyophilized. The amorphous salt thus obtained was dissolved in CH$_2$Cl$_2$ (1 mL), stirred 2 h ambient temperature then cooled to 5° C. and maintained 3 h. The resulting white crystalline solids were collected by filtration then air dried (0.100 g, 0.172 mmol; 48.0%). $^1$H NMR (400 MHz, DMSO-d$_6$) δ 9.6 (brs, 1H), 7.77 (m, 4H), 7.49 (d, 1H), 7.2 (m, 1H), 7.0 (d, 1H), 4.26 (m, 4H), 3.97 (t, 2H), 2.06 (m, 2H), 1.66 (s, 3H)

Example 9

Synthesis of 3-(2-Bromo-4-(guanidinomethyl)phenoxy)propyl 4-bromobenzenesulfonate, benzoic acid salt

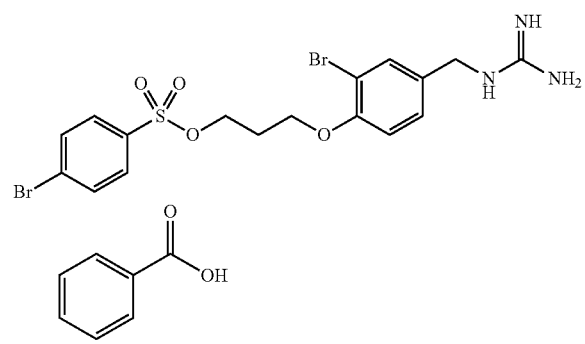

The product of Example 6 (415 mg, 0.744 mmol) was dissolved in THF/H$_2$O (4.2 mL; 1:1 v/v) then treated with AgOBz (10 mL of a 16 mg/mL solution in 1:4 MeCN/H$_2$O); immediate precipitation was observed. The slurry was stirred 20 min then filtered through a 0.45 μm PVDF filter disc and the filtrate lyophilized. The amorphous salt thus obtained was dissolved in EtOAc (10 mL), stirred 2 h ambient temperature then cooled to 5° C. and maintained 3 h. The resulting white crystalline solids were collected by filtration, washed with EtOAc (1 mL) then air dried (0.090 g, 0.140 mmol; 18.8%). $^1$H NMR (400 MHz, DMSO-d$_6$) δ 9.27 (brs, 1H), 7.88 (brs, 3H), 7.76 (m, 4H), 7.52 (d, 2H), 7.31 (m, 4H), 7.0 (d, 1H), 4.26 (m, 4H), 3.97 (m, 2H), 2.06 (m, 2H), 1.66 (s, 3H)

Example 10

Synthesis of 3-(2-Bromo-4-(guanidinomethyl)phenoxy)propyl 4-bromobenzenesulfonate, phosphoric acid salt

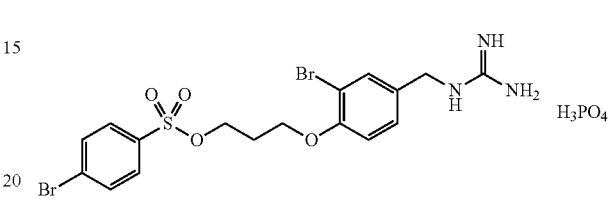

Compound 4 (0.200 g, 0.277 mmol) was dissolved in CH$_2$Cl$_2$/TFA (2 mL, 4:1 v/v) then stirred overnight at ambient temperature. All volatiles were then removed in vacuo, and the resulting thick oil further dried in a vacuum oven (2 h at 25° C. and 5 mbar). EtOAc (2 mL) and phosphoric acid (0.30 mmol; 62 μL of 5M solution in THF) were then added, and the resulting mixture refluxed 3-5 min After cooling to ambient temperature, MTBE (1 mL) was added. The resulting suspension was filtered through a scintered glass funnel, air dried then placed in a vacuum oven (48 h at 25° C. and 5 mbar; 0.164 g, 2.65 mmol; 96.2%). $^1$H NMR (400 MHz, D$_2$O+ DMSO-d$_6$) δ 7.92 (q, 4H), 7.55 (s, 1H), 7.35 (m, 1H), 7.05 (d, 1H), 4.33 (m, 4H), 4.03 (t, 2H), 2.13 (m, 2H), 1.25 (s, 1.5H).

Example 11

Synthesis of 3-(2-Bromo-4-(guanidinomethyl)phenoxy)propyl 4-bromobenzenesulfonate, methanesulfonic acid salt

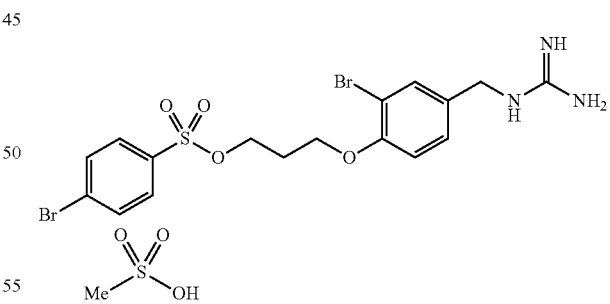

Compound 4 (1.00 g, 1.38 mmol) was dissolved in CH$_2$Cl$_2$ (8 mL) then treated with distilled TFA (2 mL) dropwise at ambient temperature and stirred overnight. All volatiles were removed and the residue successively treated with EtOAc (10 mL) and MsOH (1.52 mmol; 153 μL of a 10 M solution in THF). The resulting solution was heated to reflux, maintained 3-5 min then slowly cooled to ambient temperature in the oil bath. The solid product was isolated by filtration, air dried then placed in a vacuum oven (48 h at 25° C. and 5 mbar; 0.838 g, 1.36 mmol; 98.6%). $^1$H NMR (400 MHz, D$_2$O+

DMSO-$d_6$) δ 7.75 (d, 4H), 7.5 (s, 1H), 7.26 (d, 1H), 7.0 (d, 1H), 4.31 (m, 4H), 3.95 (t, 2H), 2.33 (s, 3H), 2.07 (m, 2H).

Example 12

Synthesis of 3-(2-Bromo-4-(guanidinomethyl)phenoxy)propyl 4-bromobenzenesulfonate, sulfuric acid salt

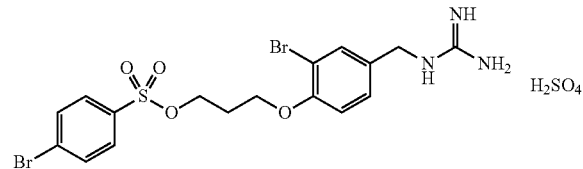

Compound 4 (0.100 g, 0.157 mmol) was suspended in dioxane (0.5 mL) then treated with sulfuric acid (0.158 mmol; 158 µL of 1 M solution in THF) at ambient temperature; additional dioxane (400 µL) was required for complete dissolution. The resulting solution was shaken several minutes then concentrated in vacuo (overnight at 25° C. and 5 mbar). The crude solid mass was triturated with hot EtOAc, briefly sonicated and cooled prior to filtration. The resulting solid material was further dried in vacuo to obtain the final product. $^1$H NMR (400 MHz, $D_2O$+DMSO-$d_6$) δ 9.8 (s, 1H), 8.1 (s, 1H), 7.75 (q, 4H), 7.5 (d, 1H), 7.25 (brs and m, 4H), 7.0 (d, 1H), 4.25 (m, 4H), 3.95 (t, 2H), 2.0 (m, 2H).

Example 13

Synthesis of 3-(2-Bromo-4-(guanidinomethyl)phenoxy)propyl 4-methylbenzenesulfonate, trifluoroacetate salt (TFA salt of Imaging Agent Precursor-2)

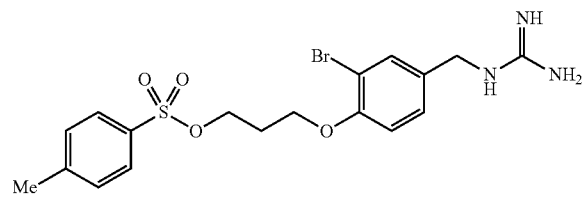

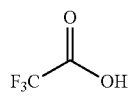

Example 13A

Synthesis of 3-(4-((2,3-bis(tert-butoxycarbonyl)guanidino)methyl)-2-bromophenoxy)propyl 4-methylbenzenesulfonate

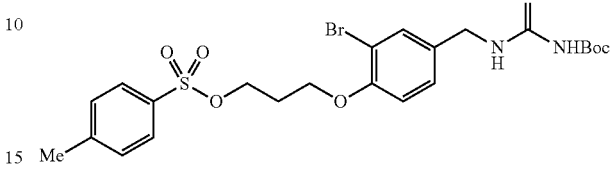

A round bottom flask was successively charged with Compound 3 (2.00 g, 3.98 mmol), 4-toluenesulfonyl chloride (0.987 g, 5.17 mmol), $Et_3N$ (0.604 g, 5.97 mmol), DMAP (0.139 g, 1.19 mmol), and $CH_2Cl_2$ (16 mL) at ambient temperature. After 5 h, the reaction mixture was poured into a separatory funnel, washed with water (10 mL) and brine (10 mL) then dried over $MgSO_4$, filtered, and concentrated to a foam. The solid was redissolved in $CH_2Cl_2$ (4 mL) then loaded onto a 40 g silica column (Redisep $R_f$) and purified using a Teledyne ISCO Combiflash instrument (A: hexanes; B: EtOAc; 0-100% B over 19.2 min; 40 mL/min) to obtain the product as a white solid (1.89 g, 72.3%). $^1$H NMR (300 MHz, $CDCl_3$) δ 11.54 (s, 1H), 8.56 (brt, 1H), 7.75 (d, 2H, J=4.5 Hz), 7.47 (d, 1H, J=3 Hz), 7.22 (m, 3H), 6.75 (d, 1H, J=4.5 Hz), 4.55 (d, 2H, J=6 Hz), 4.32 (t, 2H, J=6 Hz), 3.98 (t, 2H, J=6 Hz), 2.36 (s, 3H), 2.16 (m, 2H), 1.54 (s, 9H), 1.50 (s, 9H).

Example 13B

Synthesis of 3-(2-Bromo-4-(guanidinomethyl)phenoxy)propyl 4-bromobenzenesulfonate, trifluoroacetate salt (TFA salt of Imaging Agent Precursor-2)

A round bottom flask was charged with the product of Example 13A (1.50 g, 2.28 mmol) then treated with a solution of TFA in $CH_2Cl_2$ at ambient temperature (52 mmol: 1:1 v/v, 8 mL). After 3.5 h, the mixture was concentrated to a thick oil then treated with acetone (2 mL) and concentrated once again. The acetone evaporation process was repeated two additional times, and the residue thus obtained was dissolved in $CH_2Cl_2$ (4 mL). The $CH_2Cl_2$ was again removed in vacuo, and the process repeated two additional times to obtain the crude product as a pale yellow solid. The solid was finally washed with MTBE (2×10 mL) and EtOAc (5 mL) to yield the TFA salt of imaging agent precursor-2 as a free flowing white powder. $^1$H NMR (300 MHz, DMSO-$d_6$) δ 7.98 (t, 1H, J=6 Hz), 7.74 (d, 2H, J=9 Hz), 7.51 (d, 1H, J=3 Hz), 7.34 (d, 2H, J=9 Hz), 7.26 (dd, 1H, J=3, 9 Hz), 7.02 (d, 1H, J=9 Hz), 4.30 (d, 2H, J=6 Hz), 4.22 (t, 2H, J=6 Hz), 3.99 (t, 2H, J=6 Hz), 2.35 (s, 3H), 2.07 (m, 2H).

Example 14

Salt Stability Study

Figure 7:
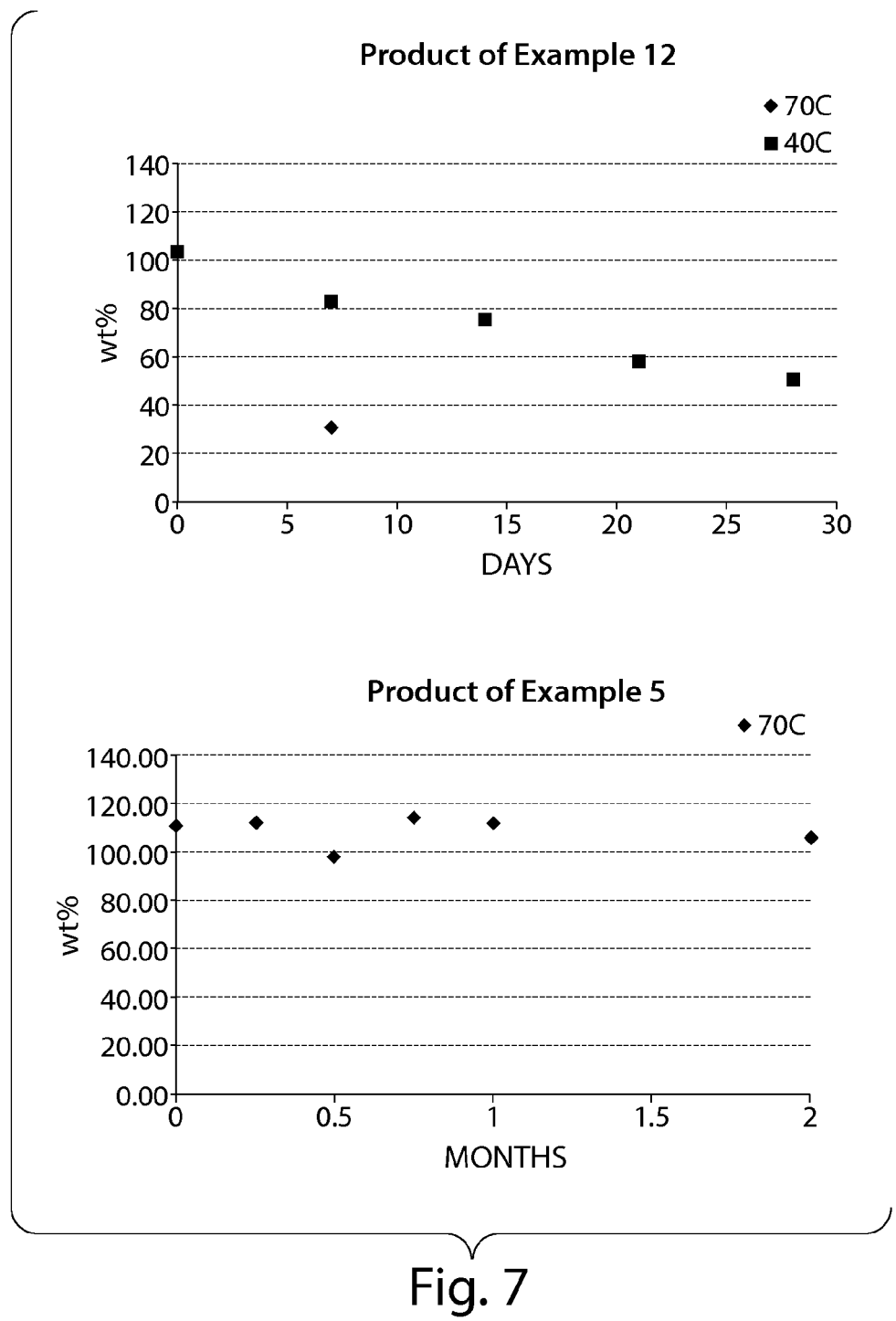
FIG. 7 show graphs of weight percent versus time for the sulfuric acid salt of imaging agent precursor-1 and the trifluoroacetic acid salt of imaging agent precursor-1.
Figure 8A:
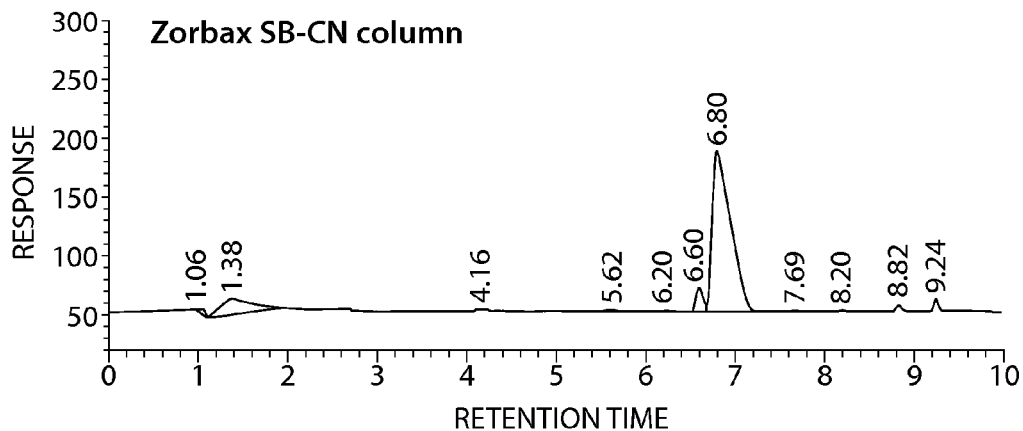
FIG. 8A-FIG. 8F show HPLC chromatograms for compounds synthesized according to methods described herein.
Figure 8B:
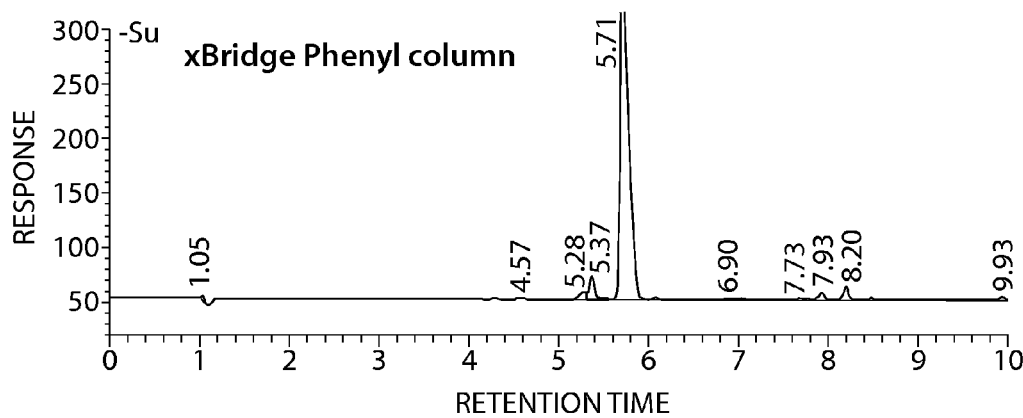
Figure 8C:
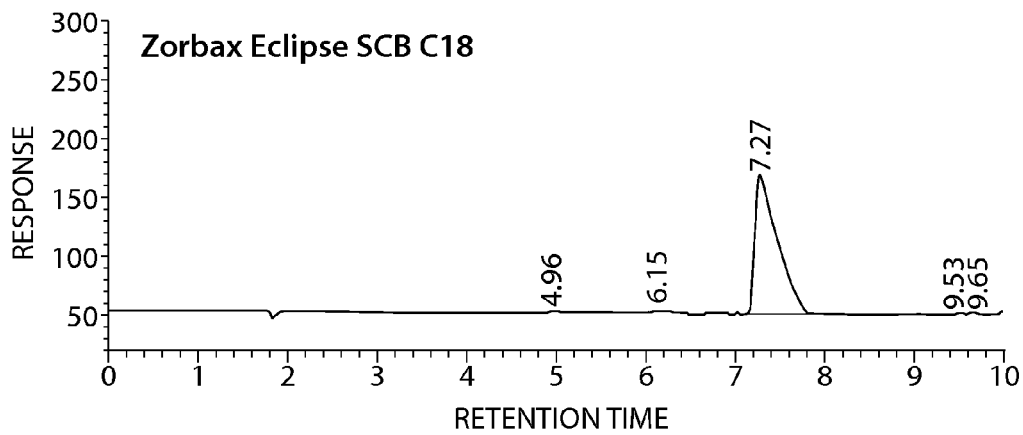
Figure 8D:
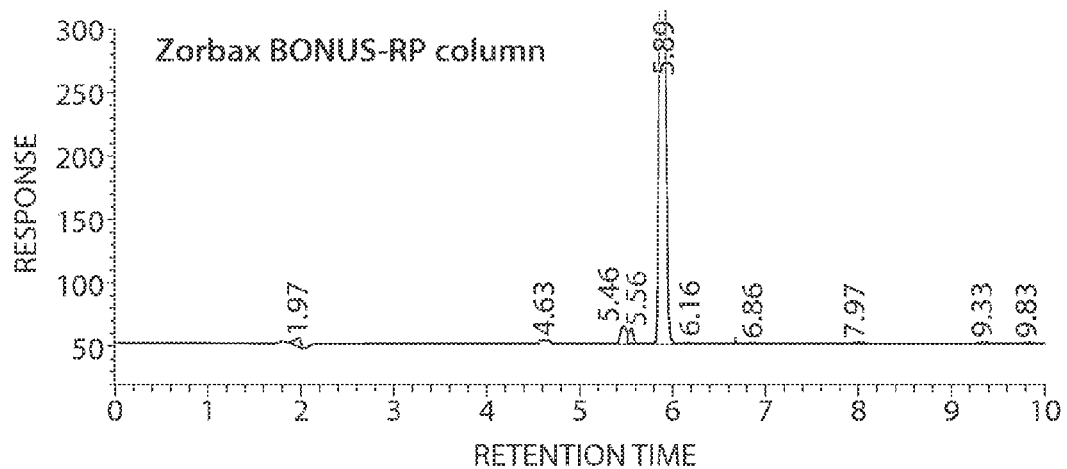
Figure 8E:
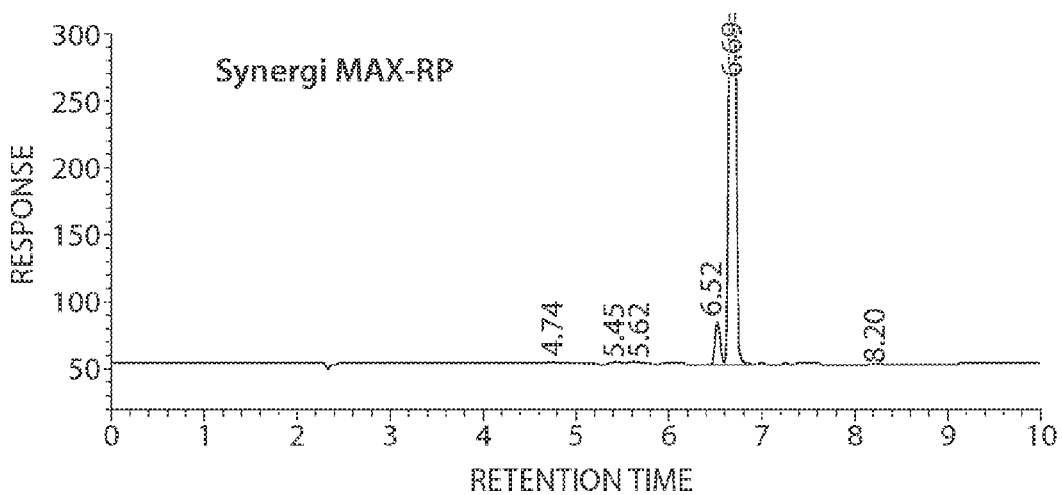
Figure 8F:
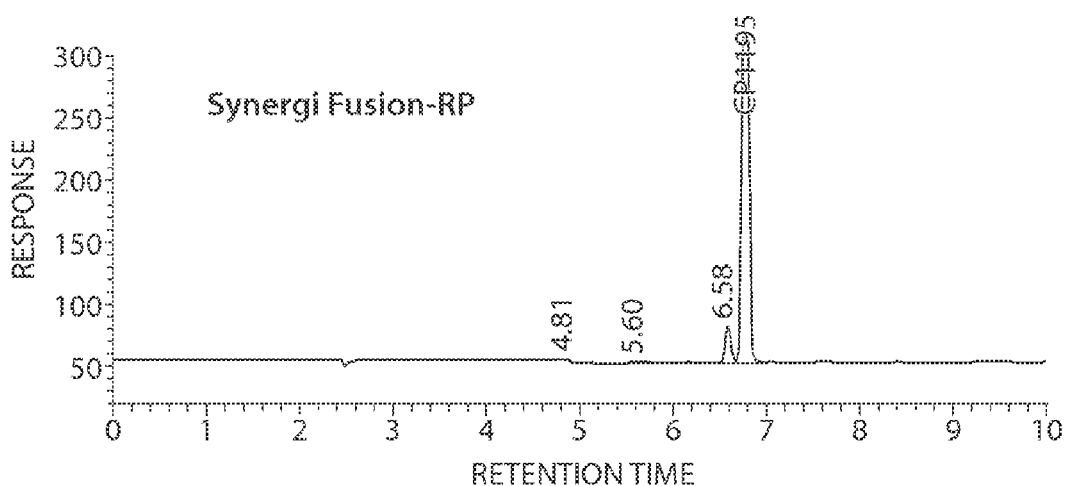

The long term chemical integrity of various salt forms of imaging agent precursor-1 were evaluated though monitoring the weight percent purity of solid samples aged under controlled storage conditions: 40 and 70° C. and 60% relative humidity. The data shown in FIG. 7 and tabulated in Table 1 detail some of the observed differences.

Example 15

Physical Properties of Selected Salt Forms

Selected physical properties of the salts of Examples 5-6 and 8-12, determined using established characterization methods, are tabulated below (Table 1).

Target volume, bombardment time and proton energy each may be adjusted to manage the quantity of [$^{18}$F]fluoride produced.

Example 17

Synthesis of 1-{3-Bromo-4-[3-[$^{18}$F]fluoropropoxy]benzyl}guanidine (Imaging Agent-1)

The product of Example 16 was transferred from cyclotron to the synthesis module, then filtered through an anion exchange column to remove unreacted [$^{18}$O]H$_2$O; [$^{18}$F]fluoride was retained within the cationic resin matrix. The column

TABLE 1

Summary of physical properties of salt forms

| | Hydrochloride | Mesylate | Phosphate | Sulfate | Acetate | Benzoate | Trifluoroacetate |
|---|---|---|---|---|---|---|---|
| Crystallinity | Crystalline | Crystalline | Crystalline | Crystalline | Crystalline | Crystalline | Crystalline |
| Stoichiometry | 1 equiv | 1 equiv | 1 equiv | 1 equiv | 1 equiv | 1 equiv | 1 equiv |
| Hygroscopicity | Indicates hydrate formation | Slight hygroscopicity | Slight hygroscopicity | Hygroscopic | -NA- | -NA- | Slight hygroscopicity |
| Stability to GVS and 40° C./75% RH | Stable | Stable | Stable | Mixture of phases | -NA- | -NA- | Stable |
| Thermal stability | First event at 117° C. | First event at 152° C. | First event at 155° C. | First event at 103° C. | -NA | -NA | First event at 142° C. |
| Solubility (Acetonitrile; mg/mL) | -NA- | 1.28 | 0.3 | -NA- | 0.4 | 1.5 | 4.68 |

The following Examples (16-20) detail development of the combination of steps used for the manufacture of imaging agent-1. A flow chart of the overall process is shown in FIG. 2.

Example 16

Preparation of [$^{18}$F]fluoride

[$^{18}$F]Fluoride was produced by proton bombardment of [$^{18}$O]H$_2$O in a cyclotron; the nuclear chemical transformation is shown below and may be summarized as $^{18}$O(p,n)$^{18}$F. For purposes of the bombardment, the chemical form of the $^{18}$O is H$_2$$^{18}$O. The chemical form of the resulting $^{18}$F is fluoride ion.

$^{18}$O+proton→$^{18}$F+neutron

According to established industry procedures, [$^{18}$O]H$_2$O (2-3 mL) housed within a tantalum target body using Havar® foil, was bombarded with 11 MeV protons (nominal energy); where the proton threshold energy for the reaction is 2.57 MeV and the energy of maximum cross section is 5 MeV.

was then washed with aqueous K$_2$CO$_3$ with transfer to the reaction vessel. The resulting solution was diluted with MeCN then concentrated to dryness using elevated temperature and reduced pressure. The anhydrous [$^{18}$F]KF thus obtained was individually treated with MeCN solutions of the products of Example 5E, 7 or 11 and Kryptofix® 222 then warmed to 110° C. and maintained 15 min.

Example 17A

Synthesis of 1-{3-Bromo-4-[3-[$^{18}$F]fluoropropoxy]benzyl}guanidine, formic acid salt (Formic Acid Salt of Imaging Agent-1)

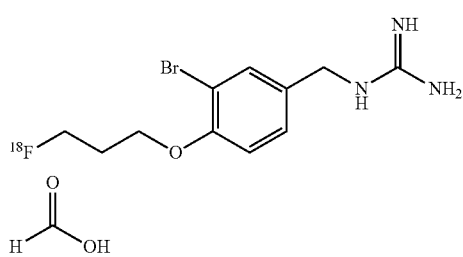

Example 17B

Development of Preparative HPLC Purification Method

Selection of parameters suitable for purification of the product of Example 17 was achieved through detailed study of the chromatographic behavior of the product of various salts of imaging agent precursor-1. Initial column screening was performed using a 9.5%/min gradient from 5-95% MeCN containing 0.1% $HCO_2H$ and 10% $H_2O$ at 1.00 mL/min, which revealed improved specificity over known impurities when using the Agilent Zorbax BONUS-RP (4.6× 150 mm) column; selected chromatograms are provided in FIG. 8A-FIG. 8F.

Following column selection, a detailed study of the optimal solvent modifier was conducted, where the counterion, concentration and ionic strength were adjusted to balance compound resolution and retention. A summary of the experimental parameters evaluated are tabulated below (Table 2).

TABLE 2

Summary of HPLC Purification - TFA salt of imaging agent precursor-1 using Agilent Zorbax BONUS-RP

| Modifier | Concentration (mM) | pH | ionic strength | Retention (min) | Tailing Factor |
|---|---|---|---|---|---|
| $HCO_2H$ | 22 | 2.81 | — | 6.88 | 0.91 |
| $HCO_2NH_4$ | 10 | 3.13 | 0.001 | 6.74 | 0.89 |
| $HCO_2NH_4$ | 10 | 3.97 | 0.006 | 7.45 | 1.08 |
| $HCO_2NH_4$ | 10 | 4.5 | 0.008 | 7.71 | 1.14 |
| $HCO_2NH_4$ | 5 | 4.5 | 0.004 | 7.76 | 1.18 |
| $HCO_2NH_4$ | 15 | 4.5 | 0.012 | 7.91 | 1.24 |
| $MeCO_2NH_4$ | 10 | 4.03 | 0.001 | 6.77 | 0.82 |
| $MeCO_2NH_4$ | 10 | 4.46 | 0.003 | 7.34 | 1.04 |
| $MeCO_2NH_4$ | 10 | 5.48 | 0.008 | 8.01 | 1.32 |

Example 17C

Synthesis of 1-{3-Bromo-4-[3-[$^{18}$F]fluoropropoxy]benzyl}guanidine, formic acid salt

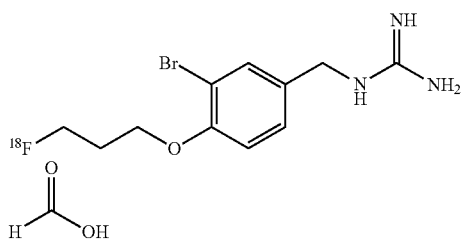

The product of Example 17 was cooled to ambient temperature and the solution concentrated. The crude product was diluted with $H_2O$/MeCN (1 mL, 4:1 v/v) then directly purified by HPLC on an Agilent Zorbax BONUS-RP column using a solution of $NH_4HCO_2$ in $H_2O$/MeCN. The main product peak was collected then assayed to determine radiochemical yield and purity.

TABLE 3

Summary of radiochemical yield and purity from various precursor salt forms

|  | Imaging agent precursor-1 | Example 7 | Example 11 |
|---|---|---|---|
| Radiochemical Yield | 60% | 35% | 15% |
| Radiochemical Purity | 99% | 100% | 99% |

Example 18

General Preparation of Imaging Agent-1

The following Example describes a general procedure for synthesizing imaging agent-1, using an automated synthesis module. Aqueous [$^{18}$F]fluoride, as prepared in Example 16, was transferred from the cyclotron to a synthesis module, then filtered through an anion exchange column to remove unreacted [$^{18}$O]$H_2O$; [$^{18}$F]fluoride was retained within the cationic resin matrix. The column was then washed with aqueous base with transfer to the reaction vessel. The resulting solution was optionally diluted with MeCN then concentrated to dryness using elevated temperature and reduced pressure. The mixture of anhydrous [$^{18}$F]fluoride and base thus obtained was treated with a solution of imaging agent precursor-1 (or a salt thereof), optionally an activating agent then warmed to 90-110° C. and maintained 5-15 min. After cooling, the solution was evaporated to dryness using elevated temperature and reduced pressure then reconstituted in $H_2O$/MeCN and directly purified by HPLC on an Agilent BONUS-RP column using a solution of $NH_4HCO_2$ in $H_2O$/MeCN. The main product peak was collected, diluted with ascorbic acid then transferred to the formulation module.

Example 18A-1

Preparation of Formic Acid Salt of Imaging Agent-1 Using the Eckert & Ziegler Modular-Lab Synthesis Module The product of Example 15 was transferred from a cyclotron to the synthesis module then filtered through an anion exchange column to remove unreacted [$^{18}$O]$H_2O$; [$^{18}$F]fluoride was retained within the cationic resin matrix. The column was then washed with $K_2CO_3$ (11.5 µmol; 0.500 mL of a 23.0 mM solution in $H_2O$) with transfer to the reaction vessel. The resulting solution was diluted with MeCN (0.500 mL) then concentrated to dryness using a two step procedure; heating to 135° C. for 5 min under vacuum and nitrogen flow (500 mL/min) then at 100° C. for 10 min under vacuum and nitrogen flow (500 mL/min). The mixture of anhydrous [$^{18}$F]KF and $K_2CO_3$ thus obtained was treated with a solution of the TFA salt of imaging agent precursor-1 5.00 mg, 7.87 µmol) and Kryptofix® 222 (22.5 mg, 59.7 µmol) in t-BuOH:MeCN (4:1 v/v; 1.5 mL) then warmed to 110° C. and maintained 15 min. The resulting solution was cooled to 95° C. then concentrated for 5 min under a flow of nitrogen. The mixture was then treated with $H_2O$/MeCN (4:1 v/v; 1.00 mL) and warmed to 100° C. for 5 min. After cooling for 60 sec, the resulting solution was directly purified by HPLC on an Agilent BONUS-RP (10 µm; 9.4×250 mm) column using a 82:18 $H_2O$/MeCN eluent containing $NH_4HCO_2$ (pH 3.8) at a flow rate of 5 mL/min. The main product peak eluting at 12-14 min was collected, diluted with ascorbic acid (10 mL of a 0.28 M solution in H$_2$O; pH 4) then transferred to the formulation module; 50% decay corrected radiochemical yield.

Example 18A-2

Preparation of Formic Acid Salt of Imaging Agent-1 Using the Eckert & Ziegler Modular-Lab Synthesis Module The product of Example 16 was transferred from cyclotron to the synthesis module then filtered through an anion exchange column to remove unreacted [$^{18}$O]H$_2$O; [$^{18}$F]fluoride was retained within the cationic resin matrix. The column was then washed with K$_2$CO$_3$ (2.01 µmol; 0.500 mL of a 4.02 mM solution in H$_2$O) with transfer to the reaction vessel. The resulting solution was diluted with MeCN (0.500 mL) then concentrated to dryness using a two step procedure; heating to 135° C. for 3 min under vacuum and nitrogen flow (500 mL/min) then at 100° C. for 9 min under vacuum and nitrogen flow (500 mL/min). The mixture of anhydrous [$^{18}$F]KF and K$_2$CO$_3$ thus obtained was treated with a solution of the product of Example 7 (1.00 mg, 1.44 µmol) and Kryptofix® 222 (4.11 mg, 11.0 µmol) in t-BuOH:MeCN (4:1 v/v; 1.5 mL) then warmed to 110° C. and maintained 15 min. The resulting solution was cooled to 95° C. then concentrated for 5 min under a flow of nitrogen. The mixture was then treated with H$_2$O/MeCN (4:1 v/v; 1.00 mL) and warmed to 100° C. for 5 min. After cooling for 60 sec, the resulting solution was directly purified by HPLC on an Agilent BONUS-RP (10 µm; 9.4×250 mm) column using a 82:18 H$_2$O/MeCN eluent containing NH$_4$HCO$_2$ (pH 3.8) at a flow rate of 5 mL/min. The main product peak eluting at 12-14 min was collected, diluted with ascorbic acid (10 mL of a 0.28 M solution in H$_2$O; pH 4) then transferred to the formulation module; 33% decay corrected radiochemical yield.

Example 18A-3

Preparation of Formic Acid Salt of Imaging Agent-1 Using the Eckert & Ziegler Modular-Lab Synthesis Module The product of Example 16 was transferred from cyclotron to the synthesis module then filtered through an anion exchange column to remove unreacted [$^{18}$O]H$_2$O; [$^{18}$F]fluoride was retained within the cationic resin matrix. The column was then washed with K$_2$CO$_3$ (2.01 µmol; 0.500 mL of a 4.02 mM solution in H$_2$O) with transfer to the reaction vessel. The resulting solution was diluted with MeCN (0.500 mL) then concentrated to dryness using a two step procedure; heating to 135° C. for 3 min under vacuum and nitrogen flow (500 mL/min) then at 100° C. for 9 min under vacuum and nitrogen flow (500 mL/min). The mixture of anhydrous [$^{18}$F]KF and K$_2$CO$_3$ thus obtained was treated with a solution of the product of Example 11 (0.88 mg, 1.44 µmol) and Kryptofix® 222 (4.11 mg, 11.0 µmol) in t-BuOH:MeCN (4:1 v/v; 1.5 mL) then warmed to 110° C. for 15 min. The resulting solution was cooled to 95° C. then concentrated for 5 min under a flow of nitrogen. The mixture was then treated with H$_2$O/MeCN (4:1 v/v; 1.00 mL) and warmed to 100° C. for 5 min. After cooling for 60 sec, the resulting solution was directly purified by HPLC on an Agilent BONUS-RP (10 µm; 9.4×250 mm) column using a 82:18 H$_2$O/MeCN eluent containing NH$_4$HCO$_2$ (pH 3.8) at a flow rate of 5 mL/min. The main product peak eluting at 12-14 min was collected, diluted with ascorbic acid (10 mL of a 0.28 M solution in H$_2$O; pH 4) then transferred to the formulation module; 15% decay corrected radiochemical yield.

Example 18A-4

Preparation of Formic Acid Salt of Imaging Agent-1 Using the Eckert & Ziegler Modular-Lab Synthesis Module The product of Example 16 was transferred from cyclotron to the synthesis module then filtered through an anion exchange column to remove unreacted [$^{18}$O]H$_2$O; [$^{18}$F]fluoride was retained within the cationic resin matrix. The column was then washed with Et$_4$NHCO$_3$ (39.4 µmol; 0.500 mL of a 78.8 mM solution in H$_2$O) with transfer to the reaction vessel. The resulting solution was diluted with MeCN (0.500 mL) then concentrated to dryness using a two step procedure; heating to 135° C. for 5 min under vacuum and nitrogen flow (500 mL/min) then at 100° C. for 10 min under vacuum and nitrogen flow (500 mL/min). The mixture of anhydrous [$^{18}$F]Et$_4$NF and Et$_4$NHCO$_3$ thus obtained was treated with a solution of imaging agent precursor-1 (5.00 mg, 7.87 µmol) in t-BuOH:MeCN (4:1 v/v; 1.0 mL) then warmed to 110° C. for 15 min. The resulting solution was cooled to 95° C. then concentrated for 5 min under a flow of nitrogen. The mixture was then treated with H$_2$O/MeCN (4:1 v/v; 1.00 mL) and warmed to 100° C. for 5 min. After cooling for 60 sec, the resulting solution was directly purified by HPLC on an Agilent BONUS-RP (10 µm; 9.4×250 mm) column using a 82:18 H$_2$O/MeCN eluent containing NH$_4$HCO$_2$ (pH 3.8) at a flow rate of 5 mL/min. The main product peak eluting at 12-14 min was collected, diluted with ascorbic acid (10 mL of a 0.28 M solution in H$_2$O; pH 4) then transferred to the formulation module; 46% decay corrected radiochemical yield.

Example 18A-5

Preparation of Formic Acid Salt of Imaging Agent-1 Using the Eckert & Ziegler Modular-Lab Synthesis Module The product of Example 16 was transferred from cyclotron to the synthesis module then filtered through an anion exchange column to remove unreacted [$^{18}$O]H$_2$O; [$^{18}$F]fluoride was retained within the cationic resin matrix. The column was then washed with Et$_4$NHCO$_3$ (31.5 µmol; 0.500 mL of a 63.0 mM solution in H$_2$O) with transfer to the reaction vessel. The resulting solution was diluted with MeCN (0.500 mL) then concentrated to dryness using a two step procedure; heating to 135° C. for 5 min under vacuum and nitrogen flow (500 mL/min) then at 100° C. for 10 min under vacuum and nitrogen flow (500 mL/min). The mixture of anhydrous [$^{18}$F]Et$_4$NF and Et$_4$NHCO$_3$ thus obtained was treated with a solution of the TFA salt of imaging agent precursor-1 (4.00 mg, 6.30 µmol) in MeCN (1.0 mL) then warmed to 110° C. for 15 min. The resulting solution was cooled to 95° C. then concentrated for 5 min under a flow of nitrogen. The mixture was then treated with H$_2$O/MeCN (4:1 v/v; 1.00 mL) and warmed to 100° C. for 5 min. After cooling for 60 sec, the resulting solution was directly purified by HPLC on an Agilent BONUS-RP (10 µm; 9.4×250 mm) column using a 82:18 H$_2$O/MeCN eluent containing NH$_4$HCO$_2$ (pH 3.8) at a flow rate of 5 mL/min. The main product peak eluting at 12-14 min was collected, diluted with ascorbic acid (10 mL of a 0.28 M solution in H$_2$O; pH 4) then transferred to the formulation module; 42% decay corrected radiochemical yield.

Example 18A-6

Preparation of Formic Acid Salt of Imaging Agent-1 Using the Eckert & Ziegler Modular-Lab Synthesis Module The product of Example 16 was transferred from cyclotron to the synthesis module then filtered through an anion exchange column to remove unreacted [$^{18}$O]H$_2$O; [$^{18}$F]fluoride was retained within the cationic resin matrix. The column was then washed with Et$_4$NHCO$_3$ (39.5 µmol; 0.500 mL of a 79.0 mM solution in H$_2$O) with transfer to the reaction vessel. The resulting solution was diluted with MeCN (0.500 mL) then concentrated to dryness using a two step procedure; heating to 135° C. for 5 min under vacuum and nitrogen flow (500 mL/min) then at 100° C. for 10 min under vacuum and nitrogen flow (500 mL/min). The mixture of anhydrous [$^{18}$F] Et$_4$NF and Et$_4$NHCO$_3$ thus obtained was treated with a solution of the TFA salt of imaging agent precursor-2 (4.50 mg, 7.87 µmol) in MeCN (1.0 mL) then warmed to 110° C. and maintained 15 min. The resulting solution was cooled to 95° C. then concentrated for 5 min under a flow of nitrogen. The mixture was then treated with H$_2$O/MeCN (4:1 v/v; 1.00 mL), warmed to 100° C. and maintained 5 min. After cooling 60 sec, the resulting solution was directly purified by HPLC on an Agilent BONUS-RP (10 µm; 9.4×250 mm) column using a 82:18 H$_2$O/MeCN eluent containing NH$_4$HCO$_2$ (pH 3.8) at a flow rate of 5 mL/min. The main product peak eluting at 12-14 min was collected, diluted with ascorbic acid (10 mL of a 0.28 M solution in H$_2$O; pH 4) then transferred to the formulation module; 46% decay corrected radiochemical yield.

Example 18B-1

Preparation of Formic Acid Salt of Imaging Agent-1 Using the GE TRACERLab MX Synthesis Module The product of Example 16 was transferred from cyclotron to the synthesis module then filtered through an anion exchange column to remove unreacted [$^{18}$O]H$_2$O; [$^{18}$F]fluoride was retained within the cationic resin matrix. The column was then washed with K$_2$CO$_3$ (11.5 µmol; 0.800 mL of a 14.4 mM solution in H$_2$O) with transfer to the reaction vessel. The resulting solution was then concentrated to dryness using a two step procedure; heating to 95° C. for 3 min under vacuum and nitrogen flow then at 115° C. for 7 min under vacuum and nitrogen flow. The mixture of anhydrous [$^{18}$F]KF and K$_2$CO$_3$ thus obtained was treated with a solution of the TFA salt of imaging agent precursor-1 (5.00 mg, 7.87 µmol) and Kryptofix® 222 (22.5 mg, 59.7 µmol) in t-BuOH:MeCN (4:1 v/v; 1.5 mL) then warmed to 110° C. and maintained 15 min. The resulting solution was cooled to 95° C. then concentrated for 7 min under a flow of nitrogen. The mixture was then treated with H$_2$O/MeCN (4:1 v/v; 5.00 mL) and then warmed to 95° C. for 5 min. After cooling to 50° C., the resulting solution was directly purified by HPLC on an Agilent BONUS-RP (10 µm; 9.4×250 mm) column using a 82:18 H$_2$O/MeCN eluent containing NH$_4$HCO$_2$ (pH 3.8) at a flow rate of 5 mL/min. The main product peak eluting at 10-12 min was collected, diluted with ascorbic acid (10 mL of a 0.28 M solution in H$_2$O; pH 4), and then transferred to the formulation module; 20% decay corrected radiochemical yield. A flow diagram for the process outlined above is provided in FIG. 3.

Example 18B-2

Preparation of Formic Acid Salt of Imaging Agent-1 Using the GE TRACERLab MX Synthesis Module The product of Example 16 is transferred from cyclotron to the synthesis module then filtered through an anion exchange column to remove unreacted [$^{18}$O]H$_2$O; [$^{18}$F]fluoride is retained within the cationic resin matrix. The column is then washed with Et$_4$NHCO$_3$ (39.5 µmol; 0.500 mL of a 79.0 mM solution in H$_2$O) with transfer to the reaction vessel. The resulting solution is then concentrated to dryness using a two step procedure; heating to 95° C. for 3 min under vacuum and nitrogen flow then at 115° C. for 7 min under vacuum and nitrogen flow. The mixture of anhydrous [$^{18}$F]Et$_4$NF and Et$_4$NHCO$_3$ thus obtained is treated with a solution of the TFA salt of imaging agent precursor-2 (4.50 mg, 7.87 µmol) in MeCN (1.0 mL) then warmed to 90° C. and maintained 10 min. The resulting solution is cooled to 95° C. then concentrated for 7 min under a flow of nitrogen. The mixture is then treated with H$_2$O/MeCN (4:1 v/v; 2.00 mL), warmed to 90° C. and maintained 5 min. After cooling to 50° C., the resulting solution is directly purified by HPLC on an Agilent BONUS-RP (10 µm; 9.4×250 mm) column using a 82:18 H$_2$O/MeCN eluent containing NH$_4$HCO$_2$ (pH 3.8) at a flow rate of 5 mL/min. The main product peak eluting at 10-12 min is collected, diluted with ascorbic acid (10 mL of a 0.28 M solution in H$_2$O; pH 4) then transferred to the formulation module. A flow diagram for the process outlined above is provided in FIG. 4.

Example 18C

Preparation of Formic Acid Salt of Imaging Agent-1 Using the GE TRACERLab FX Synthesis Module The product of Example 16 was transferred from cyclotron to the synthesis module then filtered through an anion exchange column to remove unreacted [$^{18}$O]H$_2$O; [$^{18}$F]fluoride was retained within the cationic resin matrix. The column was then washed with K$_2$CO$_3$ (11.5 µmol; 0.800 mL of a 14.4 mM solution in H$_2$O) with transfer to the reaction vessel. The resulting solution was then concentrated to dryness using a two step procedure; heating to 68° C. for 3 min under vacuum and helium flow then at 95° C. for 4 min under vacuum and helium flow. The mixture of anhydrous [$^{18}$F]KF and K$_2$CO$_3$ thus obtained was cooled to 70° C., treated with a solution of the TFA salt of imaging agent precursor-1 (5.00 mg, 7.87 µmol) and Kryptofix® 222 (22.5 mg, 59.7 µmol) in t-BuOH: MeCN (4:1 v/v; 1.5 mL) then warmed to 95° C. and maintained 15 min. The resulting solution was cooled to 55° C. then concentrated for 7 min under a flow of helium. The mixture was further treated with H$_2$O (0.1 mL), maintained 2 min then cooled to 40° C. and diluted with H$_2$O/MeCN (4:1 v/v; 3.00 mL). The resulting solution was directly purified by HPLC on an Agilent BONUS-RP (10 µm; 9.4×250 mm) column using a 82:18 H$_2$O/MeCN eluent containing NH$_4$HCO$_2$ (pH 3.8) at a flow rate of 5 mL/min. The main product peak eluting at 9-11 min was collected, diluted with ascorbic acid (10 mL of a 0.28 M solution in H$_2$O; pH 4) then transferred to the formulation module; 40% decay corrected radiochemical yield.

Example 18D

Preparation of Formic Acid Salt of Imaging Agent-1 Using the Siemens Explora RN Synthesis Module The product of Example 16 was transferred from cyclotron to the synthesis module then filtered through an anion exchange column to remove unreacted [$^{18}$O]H$_2$O; [$^{18}$F]fluoride was retained within the cationic resin matrix. The column was then washed with K$_2$CO$_3$ (11.5 μmol; 0.800 mL of a 14.4 mM solution in H$_2$O) with transfer to the reaction vessel. The resulting solution was then concentrated to dryness using a two step procedure; heating to 95° C. for 2 min under vacuum and nitrogen flow then at 115° C. for 5 min under vacuum and nitrogen flow. The mixture of anhydrous [$^{18}$F]KF and K$_2$CO$_3$ thus obtained was successively treated with a solution of the TFA salt of imaging agent precursor-1 (4.00 mg, 6.30 μmol) in MeCN (1.00 mL) and Kryptofix® 222 (18.0 mg, 47.8 μmol) also in MeCN (0.50 mL) then warmed to 110° C. and maintained 15 min. The resulting solution was cooled to 95° C. then concentrated for 5 min under a flow of nitrogen. The mixture was then cooled to 55° C., treated with H$_2$O/MeCN (4:1 v/v; 1.00 mL) and directly purified by HPLC on an Agilent BONUS-RP (10 μm; 9.4×250 mm) column using a 82:18 H$_2$O/MeCN eluent containing NH$_4$HCO$_2$ (pH 3.8) at a flow rate of 5 mL/min. The main product peak eluting at 12-14 min was collected, diluted with ascorbic acid (10 mL of a 0.28 M solution in H$_2$O; pH 4) then transferred to the formulation module; 32% decay corrected radiochemical yield.

Example 18E

Preparation of Formic Acid Salt of Imaging Agent-1 Using the Explora GN Synthesis Module The product of Example 16 is transferred from cyclotron to the synthesis module then filtered through an anion exchange column to remove unreacted [$^{18}$O]H$_2$O; [$^{18}$F]fluoride was retained within the cationic resin matrix. The column is then washed with Et$_4$NHCO$_3$ (39.5 μmol; 1.00 mL of a 39.5 mM solution in H$_2$O) with transfer to the reaction vessel. The resulting solution is diluted with MeCN (1.00 mL) then concentrated to dryness; 110-115° C. Additional MeCN (1.50 mL) is then added and the solution concentrated to dryness once again. The mixture of anhydrous [$^{18}$F]Et$_4$NF and Et$_4$NHCO$_3$ thus obtained is treated with a solution of the TFA salt of imaging agent precursor-2 (4.50 mg, 7.87 μmol) in MeCN (1.0 mL) then warmed to 90° C. and maintained 10 min. The resulting solution is cooled to 60° C. then concentrated to dryness; 95° C. The mixture is then treated with H$_2$O/MeCN (4:1 v/v; 2.00 mL), warmed to 100° C. and maintained 5 min. After cooling to 60° C., the resulting solution is directly purified by HPLC on an Agilent BONUS-RP (10 μm; 9.4×250 mm) column using a 82:18 H$_2$O/MeCN eluent containing NH$_4$HCO$_2$ (pH 3.8) at a flow rate of 5 mL/min. The main product peak eluting at 12-14 min is collected, diluted with ascorbic acid (10 mL of a 0.28 M solution in H$_2$O; pH 4) then transferred to the formulation module. A flow diagram for the process outlined above is provided in FIG. 5.

Example 19

Solvent Exchange

Imaging agent-1 was transferred from purification to the formulation module then filtered through a tC18 Sep-Pak® cartridge to remove MeCN; imaging agent-1 was retained on the C18 matrix, and the filtrate was discarded. The cartridge was successively washed with ascorbic acid (10 mL of a 0.28 M solution in H$_2$O; pH 4), the filtrate discarded, then EtOH/H$_2$O (1.00 mL; 1:1 v/v), and the filtrate collected. The ethanol concentrate thus obtained was further diluted with ascorbic acid (9.0 mL of a 0.28 M solution in H$_2$O; pH 5.8) in preparation for final aseptic filtration.

Example 20

Aseptic Filtration Process

The final product vial assembly was constructed from the following pre-sterilized components: one 30 mL product vial, one Millipore Millex GV4 venting filter (0.22 μm×4 mm), one tuberculin syringe (1 mL) and one insulin syringe (0.5 mL). The product of Example 19 was then transferred from formulation to the final product vial assembly through a Millipore Millex GV PVDF sterilizing filter (0.22 μm×13 mm). Quality control samples are then removed, using the syringe assemblies, to complete all product release requirements.

Example 21

Figure 9A:
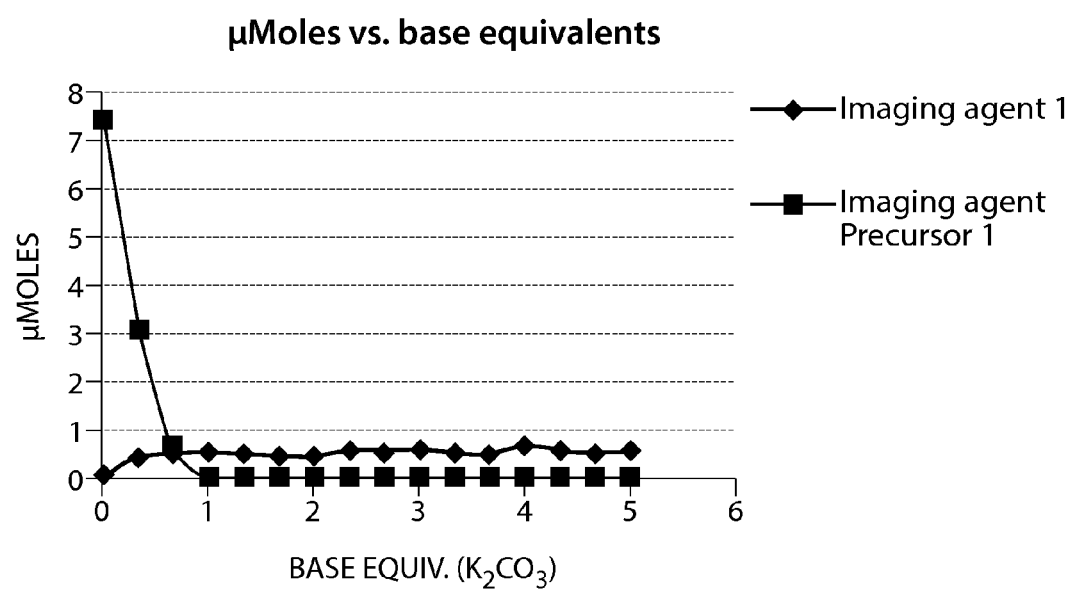
FIG. 9A shows a graph illustrating the changes in product distribution as a function of carbonate stoichiometry.

Evaluation of several experimental parameters in the nucleophilic fluorination of imaging agent precursor-1 using the K$_2$CO$_3$/Kryptofix® 222 reagent combination initially revealed that while overall reaction complexity increased with added K$_2$CO$_3$, fluorination efficiency remained unchanged above 0.66 molar equivalents (FIG. 9A). Elevated base (e.g., carbonate) levels were primarily correlated to unproductive consumption of starting material (e.g., imaging agent precursor-1), with hydrolysis to the derived alcohol as the primary decomposition pathway. Several alternate base combinations (Table 4), including modification of the potassium counterion as well as substitution of organic amine bases, proved less effective as promoters of the fluorination reaction (<10% conversion).

TABLE 4

Comparison of base identity and fluorination yield.

| Base | % yield |
| --- | --- |
| K$_2$CO$_3$ | 45-60 |
| KHSO$_4$ | <10 |
| K$_2$HPO$_4$ | <10 |
| KH$_2$PO$_4$ | <10 |
| i-Pr$_2$NEt | <10 |
| Tetramethylguanidine | <10 |
| Pyridine | <10 |

Lower fluorination yield was also observed in the absence of Kryptofix® 222, regardless of K$_2$CO$_3$ stoichiometry. However, the presence of Kryptofix® 222 markedly increased solution pH (10-12).

Figure 9B:
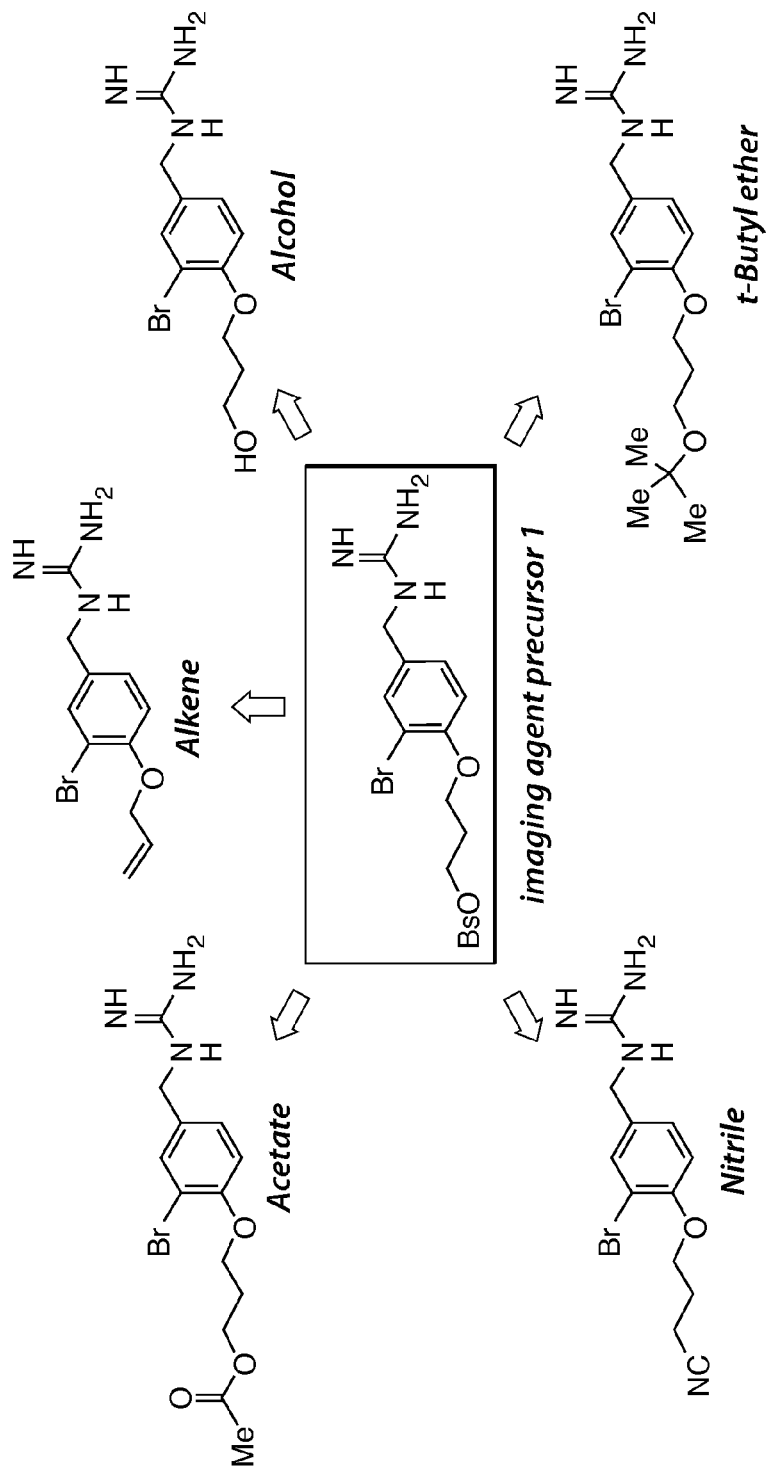
FIG. 9B shows various side products which may be formed during the synthesis of imaging agent-1 from imaging agent precursor-1.

The fluorination reaction was also evaluated in several solvent systems, including MeCN, t-BuOH, and mixtures thereof; DMF, DMSO, and THF alone. MeCN and t-BuOH:MeCN combinations proved the most effective. Analysis of crude reaction mixtures from each solvent combination revealed a specific impurity profile resulting from unproductive consumption of imaging agent precursor-1 (FIG. 9B). MeCN alone provided the best combination of fluorination efficiency and overall impurity profile.

Figure 9C:
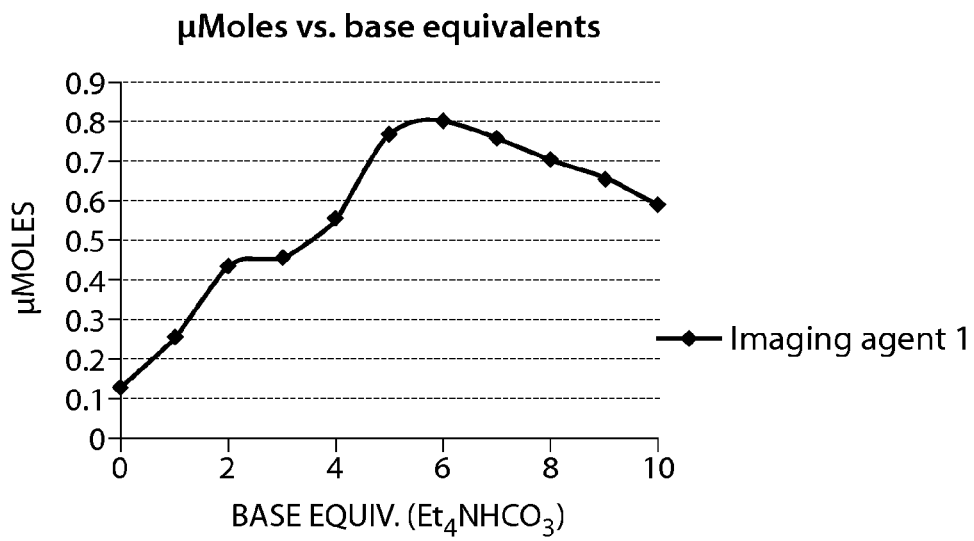
FIG. 9C shows a graph illustrating the changes in product distribution of imaging agent-1 as a function of $Et_4NHCO_3$ stoichiometry.

A subsequent series of studies revealed that both release of $^{18}$F from the anion exchange column and fluorination efficiency are markedly influenced by the identity, concentration, and composition of the basic solution utilized during transfer of $^{18}$F from the cyclotron to the reaction vessel. Specifically, we noted that regardless of cation identity (e.g., potassium or tetraalkylammonium such as tetraethylammonium or tetrabutylammonium), there exists a threshold concentration of the anionic solution component (HO$^-$, HCO$_3^-$, MsO$^-$, TsO$^-$, I$^-$), below which a decreased efficiency of $^{18}$F release occurred. Notably however, effective release of $^{18}$F was not necessarily associated with efficient fluorination. Within the tetrabutylammonium series alone (Table 5), we determined that while the bicarbonate anion was superior to other aniond, reaction efficiency was less than with the combination of K$_2$CO$_3$/Kryptofix® 222 described above (e.g., Tables 4-5). Increasing bicarbonate concentration improved overall fluorination efficiency. FIG. 9C shows the effect of concentration of tetraalkylammonium bicarbonate utilized for anion exchange on fluorination efficiency. The combination of five molar equivalents of Et$_4$NHCO$_3$ and either imaging agent precursor-1 or -2 provided equal fluorination efficiency as well as an improved overall impurity profile compared to the original K$_2$CO$_3$/Kryptofix® 222 system.

TABLE 5

Comparison of tetrabutylammonium salt form and fluorination yield.

| Salt form | % yield |
| --- | --- |
| Mesylate | <2 |
| Hydroxide | <5 |
| Tosylate | <10 |
| Iodide | 18.7 |
| Bicarbonate (8.8 mM) | 28.0 |
| Bicarbonate (34.7 mM) | 60.0 |

The non-radioactive experiments outlined above were adapted for the manufacture of imaging agent-1 on both the Siemens Explora RN and Eckert & Ziegler ModularLab remote synthesis modules. Multivariate screening studies (base, time and temperature) on the individual modules thus provided the unit-specific parameters required to maintain chemical fidelity across discrete instruments; specific parameters are described in Example 18.

Example 22

A human study was performed that determined the quantification of normal pattern of regional myocardial radioactivity concentration of imaging agent-1.

Methods:

Normal subjects (n=6) were injected with ~220 MBq of imaging agent-1 intravenously, and dynamic PET images were acquired over 80 min without patient movement. Attenuation corrected images were re-oriented into standard cardiac specific axes, and the maximal regional myocardial uptake was quantified on a sector-by-sector basis using WLCQ software. The hearts were divided into three short axis slices (Base-B; Mid-M; Apical-A) and four radial sectors (Anterior-A; Septal-S; Inferior-I; Lateral-L) and mean regional uptake for each sector was calculated. Activity was expressed as Bq/ml.

Results:

The radiotracer cleared quickly from the blood and demonstrated a favorable biodistribution for early cardiac imaging. Regional and global myocardial activity peaked within the first 10 min and reached a plateau at ~60 min post injection. There was no significant variation (p=0.69, ANOVA) in regional myocardial uptake at this time around the circumference of the heart (A: 11592±2474 Bq/ml; S: 11647±2829 Bq/ml; I: 11818±1991 Bq/ml; L:11424±2439 Bq/ml). There was also no significant (p=0.08, ANOVA) base-to-apex gradient in myocardial uptake (B:11284±2844 Bq/ml; M:11898±2047 Bq/ml; A:11678±2148 Bq/ml).

The myocardial radioactivity concentration of the imaging agent-1 was uniform throughout the heart in normal volunteers. This study established the normal pattern of quantitative regional myocardial radioactivity concentration. This type of regional myocardial analysis provides advantages over evaluation of heart-to-mediastinal ratios in future studies of patients with heart disease.

Example 23

Dosimetry in non-human primates of imaging agent-1 was examined. Imaging agent-1, which is labeled with $^{18}$F, is a novel norepinephrine transporter (NET) ligand and was a useful radiotracer for mapping the cardiac nerve terminal in vivo using positron emission tomography. A study was performed in four non-human primates to estimate human radiation dosimetry.

Methods:

In this study two male and two female cynomolgus monkeys were imaged using a Concord Focus 220 MicroPET scanner for whole body $^{18}$F distribution following 4 to 5 mCi (0.65 to 1.6 µg) single intravenous injection of imaging agent-1. Under isoflurane anesthesia, images of the animals from head to lower abdomen were acquired in 5 segments over four and half hours following injection. Radioactivity in identifiable organs and the remainder of the body was determined as a function of time using region-of-interest analysis. The total number of disintegrations per unit injected dose was determined by normalizing by the injected radioactivity and integrating over time the data for radioactivity versus time. Using the OLINDA/EXM software (Organ Level Internal Dose Assessment/EXponential Modeling Software, published by Vanderbilt University), the normalized number of $^{18}$F disintegrations for each organ was combined with the energy released by each disintegration, and using the MIRD schema, estimates were made of the fraction of the total released energy that was retained in each source organ and the contribution from each source organ to the energy deposited in surrounding target organs for an adult human. Dividing the total fractional energy deposited in each organ by the corresponding organ mass yielded the radiation dose for that organ per unit (mCi or MBq) injected dose.

Results:

From the radiation dose estimates, it was predicted that the human organ that would receive the highest dose was the urinary bladder wall with an average of 0.41±0.089 rem/mCi. The next five highest-dose organs and their respective mean dose estimates were the kidneys (0.15±0.088 rem/mCi), adrenals (0.14±0.027 rem/mCi), heart wall (0.085±0.014 rem/mCi), osteogenic cells (0.084±0.0048 rem/mCi), and red bone marrow (0.083±0.0099 rem/mCi). The mean whole body dose estimate was 0.044±0.00031 rem/mCi, and the mean effective dose as defined in ICRP 60 was 0.070±0.0059 rem/mCi. See Example 25 below for more information of effective dose.

Based on average values, the maximum dose of imaging agent-1 that may be administered to a human without exceeding 50 mSv (5 rem) to the urinary bladder was estimated to be 12 mCi. Similarly, the maximum administered dose that does not exceed 10 mSv effective dose was estimated to be 14 mCi.

Example 24

The follow Example describes the organ bio-distribution and dosimetry for imaging agent-1.

Whole organ bio-distribution and dosimetry for $^{18}$F-labeled imaging agent-1 were determined based on PET image data from twelve healthy subjects. Image quantification, kinetic modeling to determine residence times, and dosimetry analysis were performed.

Head to mid-thigh PET image data for twelve healthy subjects were obtained using $^{18}$F labeled imaging agent-1 at approximately 17, 31, 45, 117, 190, and 225 minutes post injection. Additionally, leg images were also obtained at approximately 66 and 274 minutes post injection. Image data were attenuation corrected at the imaging site, and were quantified based on the Medical Internal Radiation Dosimetry (MIRD) 16 methodology to determine kinetic data in all organs showing significant uptake of activity. Dosimetry estimates were created via kinetic modeling of the quantified image data to determine residence times, and the standard MIRD methodology using a method similar. Kinetic data, residence times, and the dosimetry estimates were reported for each subject and as summary statistics.

Results

No adverse events due to imaging agent-1 were observed. Approximately 1.6% of the injected dose (ID) was seen in the myocardium initially, remaining above 1.5% of ID (decay-corrected) through 4 hours after injection. The ratio of myocardial to liver radioactivity was approximately one initially increasing to more than two at 4 hours. Blood radioactivity cleared quickly, and lung activity was low throughout the study. On average, the organ that showed the largest peak uptake was the urinary bladder with approximately 18.3% of the injected activity. The next largest peak uptake occurred in the liver with approximately 15.5% of the injected activity.

Dosimetry Estimates:

On average, the organ receiving the largest absorbed dose was the urinary bladder wall at 0.38 rem/mCi (0.10 mSv/MBq) followed by the kidneys at 0.31 rem/mCi (0.083 mSv/MBq). The mean ED (effective dose) was 0.096 rem/mCi (0.026 mSv/MBq). Table 9 shows the absorbed dose summary statistics in rem/mCi for all subjects. Table 10 shows the absorbed dose summary statistics in mGy/MBq for all subjects.

Terms:

The following terms are used in connection with this Example.

Effective Dose (ED): Developed by the ICRP for occupational radiation protection, the ED enables the comparison of radiation detriment from a uniform external dose and a non-uniform internal dose. The risk for a 1 rem ED determined for a non-uniform internal dose is equal to the risk from a 1 rem uniform external exposure (total body dose). As defined in ICRP publication 60 [ICRP-60 1991].

Effective Dose Equivalent (EDE): Developed by the International Commission on Radiological Protection (ICRP) for occupational radiation protection, the EDE enables the comparison of radiation detriment from a uniform external dose and a non-uniform internal dose. The risk for a 1 rem EDE determined for a non-uniform internal dose is equal to the risk from a 1 rem uniform external exposure (total body dose). As defined in ICRP publication 30 [ICRP-30 1981].

TABLE 9

All Subjects - Absorbed Dose Estimates (rem/mCi) n = 12

|  | Mean | Standard Deviation | Min | Max |
|---|---|---|---|---|
| Adrenals | 0.051 | 0.003 | 0.045 | 0.056 |
| Brain | 0.019 | 0.003 | 0.017 | 0.026 |
| Breasts | 0.024 | 0.002 | 0.022 | 0.029 |
| Gallbladder Wall | 0.059 | 0.005 | 0.050 | 0.069 |
| LLI Wall | 0.047 | 0.003 | 0.041 | 0.051 |
| Small Intestine | 0.170 | 0.029 | 0.121 | 0.215 |
| Stomach Wall | 0.114 | 0.028 | 0.088 | 0.193 |
| ULI Wall | 0.059 | 0.005 | 0.051 | 0.066 |
| Heart Wall | 0.105 | 0.016 | 0.083 | 0.146 |
| Kidneys | 0.309 | 0.052 | 0.225 | 0.387 |
| Liver | 0.141 | 0.039 | 0.092 | 0.229 |
| Lungs | 0.108 | 0.019 | 0.075 | 0.146 |
| Muscle | 0.030 | 0.002 | 0.028 | 0.035 |
| Ovaries | 0.053 | 0.003 | 0.046 | 0.057 |
| Pancreas | 0.050 | 0.003 | 0.044 | 0.057 |
| Red Marrow | 0.072 | 0.009 | 0.056 | 0.090 |
| Osteogenic Cells | 0.060 | 0.005 | 0.049 | 0.069 |
| Salivary Glands | 0.127 | 0.053 | 0.075 | 0.280 |
| Skin | 0.020 | 0.002 | 0.019 | 0.025 |
| Spleen | 0.111 | 0.029 | 0.072 | 0.165 |
| Testes | 0.027 | 0.002 | 0.025 | 0.031 |
| Thymus | 0.029 | 0.003 | 0.027 | 0.036 |
| Thyroid | 0.243 | 0.039 | 0.172 | 0.294 |
| Urinary Bladder Wall | 0.376 | 0.073 | 0.179 | 0.463 |
| Uterus | 0.062 | 0.003 | 0.057 | 0.068 |
| Total Body | 0.038 | 0.002 | 0.036 | 0.043 |
| EDE | 0.115 | 0.006 | 0.103 | 0.121 |
| ED | 0.096 | 0.005 | 0.090 | 0.107 |

TABLE 10

All Subjects - Absorbed Dose Estimates (mSv/MBq) n = 12

|  | Mean | Standard Deviation | Min | Max |
|---|---|---|---|---|
| Adrenals | 0.0138 | 0.0009 | 0.0121 | 0.0152 |
| Brain | 0.0052 | 0.0007 | 0.0046 | 0.0069 |
| Breasts | 0.0065 | 0.0006 | 0.0060 | 0.0079 |
| Gallbladder Wall | 0.0159 | 0.0014 | 0.0136 | 0.0187 |
| LLI Wall | 0.0128 | 0.0007 | 0.0112 | 0.0137 |
| Small Intestine | 0.0460 | 0.0079 | 0.0327 | 0.0581 |
| Stomach Wall | 0.0308 | 0.0077 | 0.0238 | 0.0520 |
| ULI Wall | 0.0159 | 0.0013 | 0.0136 | 0.0178 |
| Heart Wall | 0.0285 | 0.0043 | 0.0223 | 0.0395 |
| Kidneys | 0.0834 | 0.0141 | 0.0608 | 0.1046 |
| Liver | 0.0382 | 0.0104 | 0.0249 | 0.0619 |
| Lungs | 0.0291 | 0.0053 | 0.0201 | 0.0395 |
| Muscle | 0.0081 | 0.0005 | 0.0077 | 0.0095 |
| Ovaries | 0.0143 | 0.0009 | 0.0123 | 0.0155 |
| Pancreas | 0.0136 | 0.0009 | 0.0120 | 0.0155 |
| Red Marrow | 0.0196 | 0.0023 | 0.0150 | 0.0242 |
| Osteogenic Cells | 0.0163 | 0.0015 | 0.0133 | 0.0187 |
| Salivary Glands | 0.0343 | 0.0144 | 0.0204 | 0.0758 |
| Skin | 0.0055 | 0.0005 | 0.0051 | 0.0068 |
| Spleen | 0.0300 | 0.0080 | 0.0195 | 0.0446 |
| Testes | 0.0074 | 0.0005 | 0.0067 | 0.0085 |
| Thymus | 0.0080 | 0.0007 | 0.0074 | 0.0098 |
| Thyroid | 0.0657 | 0.0106 | 0.0465 | 0.0795 |
| Urinary Bladder Wall | 0.1015 | 0.0197 | 0.0484 | 0.1251 |
| Uterus | 0.0169 | 0.0009 | 0.0155 | 0.0183 |
| Total Body | 0.0104 | 0.0004 | 0.0098 | 0.0115 |
| EDE | 0.0309 | 0.0015 | 0.0278 | 0.0327 |
| ED | 0.0260 | 0.0012 | 0.0244 | 0.0288 |

These data showed that imaging agent-1 was well tolerated and yielded a radiation dose comparable to that of other commonly-used PET radiopharmaceuticals. Myocardial uptake and adjacent organ activity showed that it was possible to acquire good images with acceptable patient radiation dose.

Example 25

Imaging agent-1 was designed as a substrate for the norepinephrine transporter (NET) to image the cardiac sympathetic nervous system. Competition experiments using cell membranes over-expressing the human NET indicated a $K_i$ value of 5.16±0.93 µM. In a human neuroblastoma cell line (SH-SY5Y), uptake of imaging agent-1 was inhibited by desipramine, a selective NET inhibitor, and the uptake kinetics was determined with $K_m$ and $V_{max}$ values of 6.78±1.94 µM and 5.18±1.23 pmol/min/million cells, respectively. These values were similar to that of MIBG (2.12±0.26 µM and 4.76±0.78 pmol/min/million cells). In animals, tissue biodistribution of imaging agent-1 was assessed by tissue sampling at 15- and 60-minute following administration. Heart uptake was 2.36±0.16 and 2.17±0.12% injected dose per g tissue (% ID/g) in rats and 0.25±0.03 and 0.28±0.03% ID/g in rabbits. In rabbits, desipramine (1 mg/kg) inhibited heart uptake of imaging agent-1 by 68% and $^{123}$I-MIBG uptake by 55% at 1 hour post dose. Furthermore, sympathetic denervation with 6-hydroxydopamine (6-OHDA, i.v.) also resulted in a marked decrease in imaging agent-1 uptake in the heart by 79%. Cardiac imaging with imaging agent-1 consistently showed clear myocardium with minimal background interference from blood, lung, or liver in rats, rabbits, and nonhuman primates (NHP). Consistent with biodistribution studies, imaging studies in rabbits, pretreatment with desipramine demonstrated reduced levels of radioactivity in the heart in a dose dependent manner. Similarly, 6-OHDA induced sympathetic denervation resulted in low cardiac image intensity with imaging agent-1 but normal perfusion images with the PET perfusion agent, (2-tert-butyl-4-chloro-5-[4-(2-[$^{18}$F]fluoroethoxymethyl)-benzyloxy]-2H-pyridazin-3-1 (see International PCT Publication No. WO2005/079391, published Sep. 1, 2005, incorporated herein by reference). Cardiac imaging with imaging agent-1 in NHPs pretreated with desipramine (0.5 mg/kg) showed a decreased radioactivity in the heart by 68%. Collectively, in vitro and in vivo findings indicate that imaging agent-1 may be used as a cardiac PET imaging agent transported into the heart via NET and may be used for assessment of cardiac neuronal function.

Example 26

The prognostic value of imaging agent-1 was evaluated in Dahl Salt Sensitive (DSS) rats, a rat model of heart failure (HF), and compared with $^{123}$I-meta-iodobenzylguanidine ($^{123}$I-MIBG). DSS rats were fed either a low salt (0.1% as control) or high salt diet (8%) for 5 or 9 weeks. To determine the progression of HF in these rats, plasma norepinephrine levels, and heart and lung weights were measured. Compared to low salt diet groups, DSS rats fed a high salt diet for 5 weeks had marked increases in norepinephrine levels (258±28 vs. 1242±184 pg/mL) and heart to body weight ratio (3.3±0.1 vs. 4.5±0.3 mg/g). By 9 weeks, the norepinephrine levels (656±219 vs. 1508±165 pg/mL) and heart to body weight ratio (3.2±0.1 vs. 6.1±0.3 mg/g) had increased further and the lung to body weight ratio had become elevated (3.9±0.1 vs. 14.0±1.4 mg/g). These rats fed a high salt diet were demonstrated to develop HF from early stage HF with myocardial hypertrophy (5-week) to late stage HF with sever lung congestion (9-week). Imaging agent-1 and MIBG heart uptake was examined in early and late stage HF rats by tissue sampling after intravenous administration. The uptake was measured using a gamma counter and expressed as differential absorption ratio (DAR). The imaging agent-1 heart uptake decreased following progression of HF from early to late stage HF (low salt group vs. high salt group: 6.9±0.6 vs. 5.1±0.6 and 8.1±0.2 vs. 3.1±0.2 DAR at 5 and 9 weeks respectively). These findings were comparable with the heart uptake of $^{123}$I-MIBG in these rats (7.3±0.1 vs. 3.8±0.5 and 7.9±0.5 vs. 2.3±0.3 DAR respectively). Cardiac PET imaging with imaging agent-1 in DSS rats fed a low salt diet showed clear myocardium with minimal background interference from blood, lung, and liver. Consistent with the findings in the tissue sampling, imaging in DSS rats fed a high salt diet showed progressively reduced radioactivity in the heart of these rats from 5 to 9 weeks. These results suggest that the profile of imaging agent-1 is similar to $^{123}$I-MIBG, and cardiac imaging with imaging agent-1 can be used to detect progression of HF in DSS rats.

Example 27

Imaging with $^{123}$I-meta-iodobenzylguanidine (MIBG) has been shown to predict heart failure progression, but the image quality is poor. Like MIBG, imaging agent-1 was designed as a substrate for norepinephrine transporter (NET), but labeled with $^{18}$F to take advantages of PET technology. This study evaluated cardiac image quality of imaging agent-1 and its affinity and selectivity to NET and uptake kinetics, in comparison with norepinephrine (NE).

Methods:

The affinity ($K_i$) was determined in a competition binding assay by incubating $^{19}$F-imaging agent-1, a cold analog of imaging agent-1, or NE with $^3$H-desmethylimipramine in cell membrane overexpressing human NET. The uptake selectivity was assessed by measuring imaging agent-1 or $^3$H-NE cell uptake with and without pretreatment of desipramine, a selective NET inhibitor, in SK-N-SH (human neuorblastoma) and PC-12 (rat pheochromocytoma) cells. In SK-NSH cells, the uptake kinetics ($K_m$ and $V_{max}$) were evaluated by measuring NET mediated uptake of imaging agent-1 or NE at various concentrations. Imaging agent-1 cardiac image quality was evaluated by PET imaging (~1.5 mCi, i.v.) in rabbits in the presence and absence of desipramine (1 mg/kg).

Results:

In competition binding assay, $K_i$ values for imaging agent-1 and NE were similar (5.2±1.1 and 3.4±1.3 µM). In cell studies, blockade of NET inhibited imaging agent-1 and NE uptake by 66±7 and 93±1% in PC-12 cells, and 91±1 and 97±1% in SK-N-SH cells. In SK-N-SH cells, $K_m$ and $V_{max}$ values for imaging agent-1 were 1.4±0.3 µM and 6.0±1.3 pMol/million cells/min similar to that of NE (2.0±0.4 µM and 6.2±0.7 pMol/million cells/min). Moreover, imaging agent-1 cell uptake was inhibited by imaging agent-1 or NE concentration-dependently. Imaging in rabbits with imaging agent-1 showed clear myocardium uptake with low liver activity. Cardiac uptake could be inhibited by desipramine.

The cell uptake profile of imaging agent-1 was similar to NE with high selectivity. Cardiac images of imaging agent-1 were clear, and the heart uptake was mediated by NET.

Example 28

Cardiac sympathetic denervation (CSD) assessed by $^{123}$I-metaiodobenzylguanidin (MIBG) imaging has been suggested to predict cardiac events including arrhythmia and death in heart failure patients (ADMIRE-HF trial). This study evaluated imaging with imaging agent-1 to identify CSD.

Methods:

Rabbit models of regional and systemic CSD were used. To develop regional CSD, a median sternotomy was performed and phenol (89% in liquid) was pained on the anterior and posterior walls of the left ventricle. To develop systemic denervation the neurotoxin, 6-hydroxydopamine (25 mg/kg on day 1, 2, 7 and 8), was administered intravenously. Two weeks following these procedures, rabbits were imaged with imaging agent-1 (~1.5 mCi, i.v.) using a microPET camera for 30 minutes. To ensure the denervation procedures did not result in perfusion changes rabbits were also imaged with the $^{18}$F perfusion imaging agent (2-tert-butyl-4-chloro-5-[4-(2-[$^{18}$F]fluoroethoxymethyl)-benzyloxy]-2H-pyridazin-3-1.

Results:

In sham-denervated rabbits, cardiac images of imaging agent-1 showed clear myocardium with uniform radioactivity distribution. The radioactivity was low in the lung and liver and cleared rapidly in blood. In rabbits with systemic denervation, image based quantification indicated an ~80% global reduction in heart uptake of imaging agent-1 compared to control animals. Similarly, regional denervation resulted in a marked reduction in imaging agent-1 in the treated regions. In contrast, cardiac imaging with (2-tert-butyl-4-chloro-5-[4-(2-[$^{18}$F]fluoroethoxymethyl)-benzyloxy]-2H-pyridazin-3-1 demonstrated well-perfused myocardium, and no differences were observed between control and denervated rabbits.

Reduced imaging agent-1 heart uptake in CSD rabbits was found to be due to impaired innervation, not to alterations in perfusion. Cardiac PET imaging with imaging agent-1 was used for detection of CSD, like $^{123}$I-MIBG, but with improved image quality and quantification.

Example 29

The following Example describes roles of cardiac norepinephrine uptake 1 and 2 in evaluation of imaging agent-1 in rats, rabbits, and non-human primates Objectives:

Norepinephrine (NE) released from cardiac sympathetic nerves is substantially cleared by neuronal uptake 1 (NE transporter) in rabbits, non-human primates, and humans, and by uptake 1 and 2 in rats. Imaging agent-1 is designed, in part, as a substrate for uptake 1 like NE and $^{123}$I-meta-iodobenzylguanidine (MIBG). This study examined species differences associated with cardiac uptake 1 and 2 for cardiac uptake of imaging agent-1.

Methods:

Desipramine, a selective uptake 1 inhibitor, was used to block cardiac uptake 1 in rats (10 mg/kg, ip), rabbits (1 mg/kg iv), and NHPs (0.5 mg/kg, iv). 6-hydroxydopamine, a neurotoxin, was injected to induce sympathetic denervation in rats (100 mg/kg ip for 7 days) and rabbits (25 mg/kg iv on day 1, 2, 7, and 8). Imaging agent-1 heart uptake in comparison with MIBG was assessed by tissue sampling at 60 minutes post imaging agent injection. Imaging was also performed with (2-tert-butyl-4-chloro-5-[4-(2-[$^{18}$F]fluoroethoxymethyl)-benzyloxy]-2H-pyridazin-3-1.

Results:

In rats, blockade of uptake 1 did not alter imaging agent-1 heart uptake compared to the control (1.41±0.07 vs. 1.47±0.22% injected dose per gram of tissue (% ID/g)). In contrast, imaging agent-1 heart uptake was reduced by 68% in uptake 1 blocked rabbits. In sympathetic denervated rats, imaging agent-1 heart uptake was comparable to the control group (2.18±0.39 vs. 2.58±0.76% ID/g). However, the uptake decreased markedly (79%) in sympathetic denervated rabbits. Similar results were found in MIBG heart uptake in rats and rabbits with uptake 1 blockade and sympathetic denervation. Consistently, (2-tert-butyl-4-chloro-5-[4-(2-[$^{18}$F]fluoroethoxymethyl)-benzyloxy]-2H-pyridazin-3-1 cardiac imaging showed comparable myocardial activity in sympathetic denervated rats to the control, but marked activity reduction in denervated rabbits and uptake 1 blocked rabbits and NHPs.

Conclusions:

In rabbits and non-human primates with uptake 1 as the main cardiac NE transporter, similar to humans, imaging agent-1 demonstrated high selectivity to neuronal uptake 1 and can be used in evaluation of cardiac sympathetic denervation. Due to high cardiac expression of uptake 2, in some embodiments, evaluation of uptake 1 substrate based neuronal imaging agents in rats should be done with caution.

Example 30

The following Example describes the assessment of heart failure medications on cardiac uptake of imaging agent-1.

Objectives:

This study investigated if commonly used HF medications affect NET mediated imaging agent-1 uptake.

Methods:

NET mediated uptake of imaging agent-1 was detected in SK-N-SH cells (human neuroblastoma known to express NET) by incubating 1 million cells with the ligand for 60 minutes in the presence or absence of desipramine (1 μM), a selective NET inhibitor. To assess drug impact on imaging agent-1 uptake, cells were pre-incubated (15 minutes) with vehicle or various concentrations (0.001 to 1000 μM) of propranolol (receptor blocker), captopril (ACE inhibitor), losartan (angiotensin II receptor inhibitor), or verapamil (calcium channel blocker) before addition of imaging agent-1 (1 μCi).

Results:

Imaging agent-1 cell uptake was 26±2% in SK-N-SH cells, and the majority (88%) was inhibited by desipramine. Substantial reduction of imaging agent-1 uptake was only observed by pre-incubation with propranolol at concentrations above 1 μM and with verapamil at concentrations above 10 μM. Losartan and captopril had no effect on imaging agent-1 uptake even at the highest concentrations tested (1000 μM) The concentrations of these HF medications producing inhibition of imaging agent-1 uptake were substantially above the steady state levels achieved for these drugs when used clinically.

Conclusions:

Based on these in vitro studies, several commonly used HF medications do not inhibit NET mediated imaging agent-1 uptake at clinically relevant concentrations.

Example 31

The following Example describes the evaluation of cardiac denervation, re-innervation and associated susceptibility to arrhythmia using imaging agent-1.

Objectives:

Regional cardiac sympathetic denervation (RCSD) may be associated with cardiac arrhythmia in heart failure patients. This study evaluated whether imaging agent-1 imaging could be used to measure RCSD subsequent re-innervation and potential association with arrhythmia susceptibility.

Methods:

Rabbit models of RCSD were developed by applying phenol directly on the surface of the left ventricular wall during a sternotomy. Two and twelve weeks following the procedure, imaging agent-1 cardiac PET imaging (~1.5 mCi, iv) were performed in these rabbits. The myocardial area with radioactivity≥50% maximum was quantified as innervated region for comparison. To evaluate susceptibility of arrhythmia in rabbits, dofetilide (10 and 40 μg/kg iv, a delayed $I_{Kr}$ inhibitor)

induced changes were assessed by measuring ECG including heart rate (HR), QTc interval (corrected by Fridericia method), and frequency of arrhythmia.

Results:

Cardiac images showed clear homogeneous myocardial uptake of imaging agent-1 in sham-denervated rabbits and reduced levels in phenol RCSD induced rabbits at 2 weeks post surgery (20702±2190 vs. 12245±905 voxels respectively). The denervated region was reduced by 12 weeks (16812±503 voxels) indicating re-innervation. Imaging with (2-tert-butyl-4-chloro-5-[4-(2-[$^{18}$F]fluoroethoxymethyl)-benzyloxy]-2H-pyridazin-3-1, a PET perfusion imaging agent, showed homogeneous myocardial distribution in all rabbits including those with RCSD regions indicating denervation did not alter blood flow. Dofetilide induced QTc prolongation, frequency of premature ventricular contraction, and torsades de pointes were more prominent in the RCSD group than in control. However, the changes in HR were comparable in the two groups.

Conclusions:

Imaging agent-1 cardiac imaging detected RCSD and re-innervation. The RCSD increased susceptibility of drug induced QTc prolongation and arrhythmia.

Example 32

The following Example describes evaluation of imaging agent-1 in tumor-bearing mice.

Example 32A

Preparation of Tumor Bearing Mouse Models

Xenograft Model:

Four to six week-old female Nude mice were anesthetized to immobilize them for subcutaneous inoculation with a range of $1.0 \times 10^6/0.1$ mL-$1.0 \times 10^8/0.1$ mL cells in sterile cell culture media then returned to their cages to recover. Cell lines were co-injected with a commercially available growth matrix (50/50 v/v) to facilitate tumor development (Matrigel®-BD Bioscience). Human cell lines included PC12 (pheochromocytoma), SH-SY-5Y and SK-N-SH (neuroblastoma).

Oncomouse Model:

Obtained through in-house breeding program.

Example 32B

Tissue Biodistribution

Figure 10:
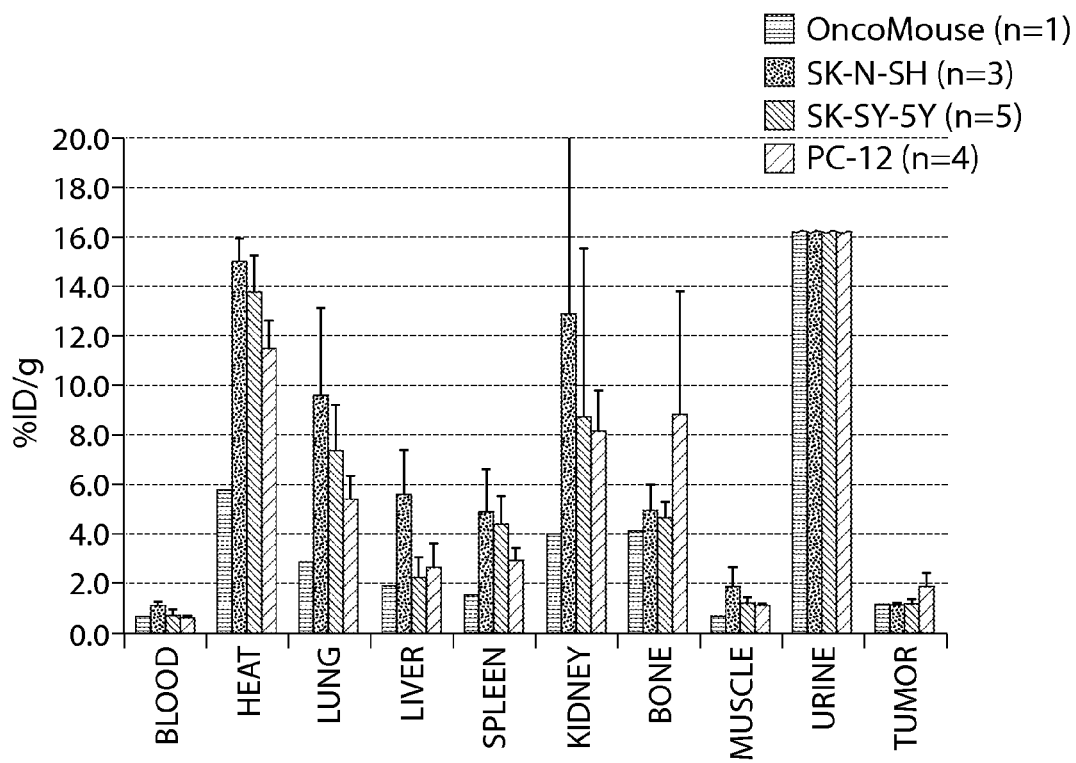
FIG. 10 shows a graph illustrating the tissue distribution of imaging agent-1 in tumor-bearing mice.

Tumor bearing mice (100-1500 mm$^3$ tumor size) were anesthetized intramuscularly with 0.1 mL of ketamine/acepromazine (1.8 mL saline, 1.0 mL ketamine, and 0.2 mL acepromazine) prior to dosing and tissue sampling. Individual mice were then injected via the tail vein with imaging agent-1 (0.5-2.0 mCi/kg in 0.1 mL). Mice were euthanized and biodistribution performed at 1 h post-injection. Selected tissues were removed, weighed, and counted on a gamma counter. Results are expressed as the percentage injected dose per gram of tissue (% ID/g; FIG. 10). Since the c-neu Oncomouse® spontaneously develops tumors in the mammary glands, most mice had more than one tumor. Each tumor was sampled and counted separately, and radioactive uptake for the tumors was averaged to obtain an overall representation of tumor uptake. Xenograft mice had only one tumor implanted and harvested at the time of tissue distribution analysis.

TERMS AND EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A composition comprising a compound comprising formula (II):

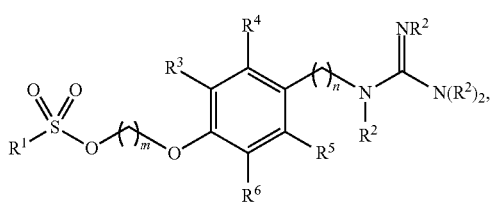

(II)

or a salt, free base, or combination thereof, wherein:
$R^1$ is alkyl, haloalkyl, alkynyl, alkenyl, heteroalkyl, cycloalkyl, aryl, heteroaryl, arylalkyl, heterocyclyl, or heteroarylalkyl, each optionally substituted;
each $R^2$ is hydrogen;
$R^3$, $R^4$, $R^5$, and $R^6$ can be the same or different and are individually hydrogen, $C_1$-$C_6$ alkyl, heteroalkyl, halide, —$OR^7$, —$SR^7$, —$N(R^7)_2$, or —$C(=O)R^8$, each optionally substituted;
each $R^7$ can be the same or different and is hydrogen, alkyl, heteroalkyl, cycloalkyl, heterocyclyl, haloalkyl, aryl, or heteroaryl, each optionally substituted;
each $R^8$ can be the same or different and is hydrogen, alkyl, heteroalkyl, cycloalkyl, haloalkyl, heterocyclyl, aryl, heteroaryl, —OH, alkoxy, —$NH_2$, alkylamino, —SH, or alkylthiol, each optionally substituted;
m is an integer between 1 and 12, inclusive; and
n is an integer between 1 and 4, inclusive.

2. A composition of claim 1, wherein the compound of formula (II) comprises the structure of formula (IV):

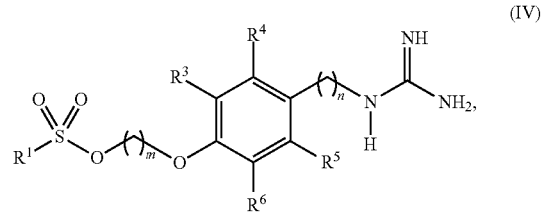

(IV)

or a salt, free base, or combination thereof.

3. The composition of claim 2, wherein the compound of formula (IV) comprises formula (III):

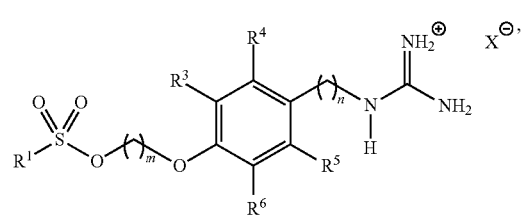

(III)

wherein $X^\ominus$ is a counter anion having a charge of (−1), (−2), or (−3).

4. The composition of claim 3, wherein $X^\ominus$ is halide, phosphate, sulfate, trifluoroacetate, tolunesulfonate, acetate, formate, citric, ascorbate, mesylate (methanesulfonate), or benzoate.

5. The composition of claim 1, wherein the compound of formula (II) comprises the formula:

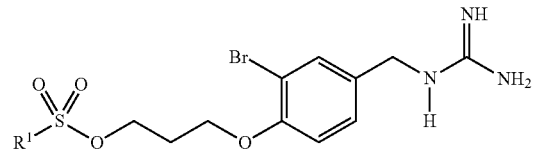

or a salt, free base, or combination thereof.

6. The composition of claim 1, wherein m is 3.
7. The composition of claim 1, wherein n is 1.
8. The composition of claim 1, wherein $R^1$ is
   (a) $C_1$-$C_6$ alkyl, haloalkyl, or aryl;
   (b) methyl, ethyl, n-propyl, i-propyl, n-butyl, i-butyl, t-butyl, pentyl, or hexyl;
   (c) haloalkyl;
   (d) $CF_3$;
   (e) phenyl, optionally substituted; or
   (f) 4-$CH_3$Ph, 2,4,6-$(CH_3)_3C_6H_2$, or $C_6H_4X$, wherein X is halide.
9. The composition of claim 1, wherein m is an integer between 1 and 10, inclusive; or between 1 and 8, inclusive; or between 1 and 6, inclusive.
10. The composition of claim 1, wherein $R^4$, $R^5$, and $R^6$ are hydrogen; and $R^3$ is halide or Br.
11. The composition of claim 1, wherein the composition comprises a salt of the compound of formula (II).
12. The composition of claim 11, wherein the salt is a pharmaceutically acceptable salt.
13. The composition of claim 1, wherein the compound of formula (II) comprises the structure:

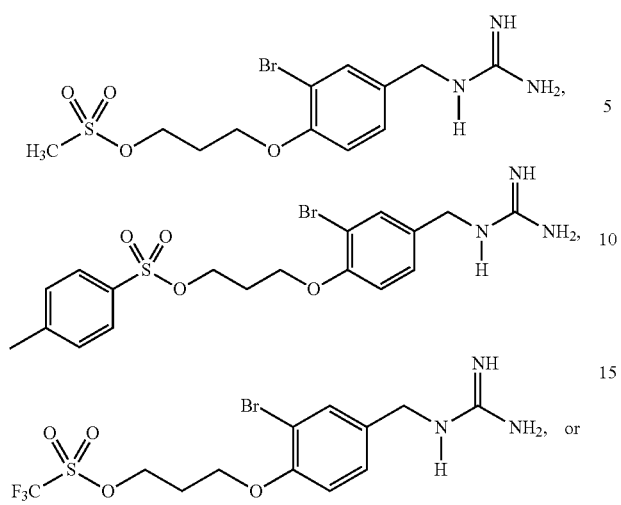
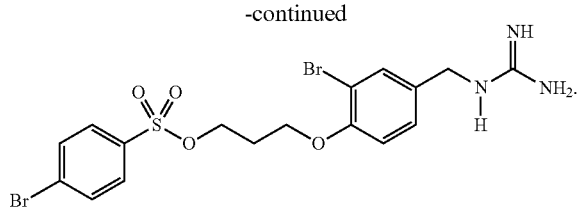
14. The composition of claim 4, wherein $X^{\ominus}$ is halide.
15. The composition of claim 3, wherein $X^{\ominus}$ is trifluoroacetate.
16. The composition of claim 3, wherein $X^{\ominus}$ is mesylate.
17. The composition of claim 3, wherein $X^{\ominus}$ is benzoate.
* * * * *